United States Patent
Ohkubo et al.

(10) Patent No.: US 6,812,235 B2
(45) Date of Patent: Nov. 2, 2004

(54) BETA-ALANINE DERIVATIVES AND THEIR USE AS RECEPTOR ANATGONISTS

(75) Inventors: Mitsuru Ohkubo, Osaka (JP); Satoru Kuroda, Osaka (JP); Hideko Nakamura, Osaka (JP); Masatoshi Minagawa, Osaka (JP); Toshiaki Aoki, Osaka (JP); Kayoko Harada, Osaka (JP); Jiro Seki, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/182,909

(22) PCT Filed: Feb. 13, 2001

(86) PCT No.: PCT/JP01/00997

§ 371 (c)(1),
(2), (4) Date: Aug. 2, 2002

(87) PCT Pub. No.: WO01/60813

PCT Pub. Date: Aug. 23, 2001

(65) Prior Publication Data

US 2003/0018193 A1 Jan. 23, 2003

(30) Foreign Application Priority Data

Feb. 17, 2000 (AU) .............................................. PQ5701

(51) Int. Cl.⁷ ..................... A61K 31/445; C07D 401/04
(52) U.S. Cl. ........................ 514/316; 514/318; 546/187; 546/188; 546/193
(58) Field of Search .......................... 514/318; 546/187, 546/188, 193

(56) References Cited

U.S. PATENT DOCUMENTS

| | | | |
|---|---|---|---|
| 5,707,994 A | * | 1/1998 | Ikeda et al. ............. 514/252.12 |
| 6,066,651 A | * | 5/2000 | Hoekstra ..................... 514/316 |
| 6,069,254 A | * | 5/2000 | Costanzo et al. ............ 546/189 |
| 6,380,215 B1 | * | 4/2002 | Ohkubo et al. ............. 514/316 |
| 6,384,028 B1 | * | 5/2002 | Ohkubo et al. ........ 514/210.21 |
| 6,538,007 B1 | * | 3/2003 | Ohkubo et al. ............. 514/316 |

FOREIGN PATENT DOCUMENTS

| | | |
|---|---|---|
| WO | 95 08536 | 3/1995 |
| WO | 95 25091 | 9/1995 |
| WO | 96 29309 | 9/1996 |
| WO | 97 33869 | 9/1997 |
| WO | 97 41102 | 11/1997 |
| WO | 99 21832 | 5/1999 |
| WO | 00 21932 | 4/2000 |

OTHER PUBLICATIONS

Hoekstra et al. "Design and evaluation of nonpeptide fibrinogen . . . " CA 123:56546 (1995).*

Hoekstra et al.: "Potent, orally active GPllb/llla antagonists containing a nipecotic acid subunit. Structure–activity studies leading to the discovery of RWJ–53308" Journal of Medicinal Chemistry, American Chemical Society, vol. 42, No. 25, pp. 5254–5265 1999.

W. Hoekstra et al.: "Design and evaluation of nonpeptide fibrinogen gamma–chain based GPllB/lllA antagonists", Journal of Medicinal Chemistry, American Chemical Society, vol. 38, No. 10, pp. 1582–1592 1995.

* cited by examiner

*Primary Examiner*—Celia Chang
(74) *Attorney, Agent, or Firm*—Oblon, Spivak, McClelland, Maier & Neustadt, P.C.

(57) ABSTRACT

A beta-alanine derivative of the formula (I) wherein $R^1$ is hydrogen atom or an amino protective group; A is a lower alkylene group or a lower alkenylene group; $R^2$ is hydrogen atom or an amino group which may be substituted with an acyl group; $R^3$ is hydrogen atom or an aryl or aralkyl group which may be substituted with one or more of hydroxy and/or lower alkoxy, a moiety represented by the formula (II), which is a bivalent N-containing 6- to 8-membered heterocyclic group, or a pharmaceutically acceptable salt thereof.

6 Claims, No Drawings

BETA-ALANINE DERIVATIVES AND THEIR USE AS RECEPTOR ANATGONISTS

TECHNICAL FIELD

The present invention relates to β-alanine derivatives and their use as receptor antagonists. More particularly, it relates to 2-acylamino-β-alanine derivatives and a pharmaceutically acceptable salt thereof and their use as fibrinogen receptor antagonists.

BACKGROUND ART

European Patent Application No. 512,831 A1 discloses fibrinogen receptor antagonists. European Patent Application No. 445,796 A2 discloses inhibitors of blood platelets aggregation. International Patent Publication Nos. WO95/08536, WO96/29309 and WO97/33869 disclose N-(3-piperidylcarbonyl)-β-alanine derivatives as platelet-activating factor (PAF) antagonists.

DISCLOSURE OF INVENTION

The present invention relates to β-alanine derivatives and their use as fibrinogen receptor antagonists.

The β-alanine derivatives of the present invention can be represented by the following formula (I):

$$\text{(I)}$$

wherein
  $R^1$ is hydrogen atom or an amino protective group;
  A is a lower allylene group or a lower alkenylene group;
  $R^2$ is hydrogen atom or an amino group which may be substituted with an acyl group selected from the group consisting of
    a lower alkanoyl group which may be substituted with amino, lower alkanoylamino, ar(lower)alkoxycarbonylamino, aryl, aroylamino, carboxy, lower alkoxycarbonylamino, ar(lower)alkoxy, lower alkoxycarbonyl, lower alkanoyloxy, lower alkoxy or hydroxy group, among which the aryl and aroylamino may further be substituted with carboxy, lower alkoxy or lower alkoxycarbonyl,
    a lower alkoxycarbonyl group which may be substituted with lower alkoxy, aryl or cyclo(lower)alkyl,
    a lower alkenyloxylcarbonyl group,
    a di(lower)alkylaminosulfonyl group,
    a cycloalkanoyl group which may be substituted with lower alkoxy,
    an aroyl group which may be substituted with ($C_3$–$C_6$) alkoxy, carbamoyl(lower)alkoxy, N-(lower)alkylcarbamoyl(lower)alkoxy, N,N-di(lower))alkylcarbamoyl(lower)alkoxy, lower alkoxycarbonyl, nitro, cyano, carboxy, carboxy(lower)alkoxy, ar(lower)alkoxy, lower alkoxycarbonyl(lower)alkoxy, cyclo(lower)alkoxy, lower alkoxycarbonylamino, cyclo(lower)alkyl(lower)alkoxy, lower alkanoylamino or lower alkylcarbamoyl,
    an aryloxycarbonyl group,
    a heterocyclylcarbonyl group,
    a protected carboxycarbonyl group and
    a heterocyclyloxycarbonyl group;
  $R^3$ is hydrogen atom or an aryl or aralkyl group which may be substituted with one or more of hydroxy and/or lower alkoxy; a moiety represented by the formula:

is a bivalent N-containing 6- to 8-membered heterocyclic group;

provided that (1) when $R^2$ is hydrogen atom, then the moiety of is a bivalent N-containing 7- or 8-membered heterocyclic group and A, $R^1$ and $R^3$ are as defined above, or $R^3$ is hydroxy- or isobutoxy-substituted phenyl group and A, $R^1$ and the moiety of are as defined above, (2) when $R^2$ is unsubstituted amino group, then the amino protective group for $R^1$ is a lower alkoxycarbonyl group and A, $R^3$ and the moiety of are as defined above, or A is a lower alkenylene group and $R^1$, $R^3$ and the moiety of are as defined above, (3) when $R^2$ is amino group substituted with an actyl group, then the moiety of

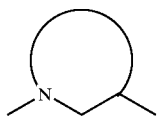

is a bivalent N-containing 7-membered heterocyclic group and A, $R^1$ and $R^3$ are as defined above, and (4) when $R^2$ is an amino group substituted with a cycloalkanoyl group which may be substituted with lower alkoxy, then $R^1$ is hydrogen atom and A, $R^3$ and the moiety of

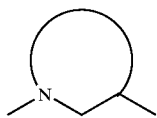

are as defined above.

In the above and subsequent descriptions of the present specification, suitable examples and illustrations of the various definitions which the present invention includes within the scope are explained in detail in the following.

The term "lower" is intended to mean a group having 1 to 7 carbon atom(s), unless otherwise indicated.

Suitable lower alkyl moieties in the terms of the lower alkanoyl, lower alkanoylamino, ar(lower)alkoxycarbonylamino, lower alkoxycarbonylanino, ar(lower)alkoxy, lower alkoxycarbonyl, lower alkanoyloxy, lower alkoxy, di(lower)alkylaminosulfonyl, carbamoyl (lower)alkoxy, N-(lower)alkylcarbamoyl(lower)alkoxy, N,N-di(lower)alkylcarbamoyl(lower)alkoxy, carboxy (lower)alkoxy, lower alkoxycarbonyl(lower)alkoxy, cyclo (lower)alkyl(lower)alkoxy and lower alkylcarbamoyl groups may be straight or branched ones having 1 to 6 carbon atoms, such as methyl, ethyl, propyl, isopropyl, butyl, isobutyl, sec-butyl, tert-butyl, pentyl, isopentyl, hexyl or the like, more suitably the ones having 1 to 4 carbon atoms such as methyl, ethyl, propyl, isopropyl, butyl, isobutyl, sec-butyl or tert-butyl.

Suitable examples of the lower alkenyl moieties in the term of lower alkenyloxylcarbonyl groups include straight or branched ones having 2 to 6 carbon atoms, such as vinyl, propenyl (i.e., allyl or 1-propenyl), butenyl, isobutenyl, pentenyl or hexenyl.

Suitable cycloalkyl moieties in the term of cyclo(lower) alkyl, cycloalkanoyl, cyclo(lower)alkoxy and cyclo(lower) alkyl(lower)alkoxy groups include the ones having 3 to 7 carbon atoms such as cyclopropyl, cyclobutyl, cyclopentyl, cyclohexyl or cycloheptyl.

Suitable aryl groups and aryl moieties in the terms of the ar(lower)alkoxycarbonylamino, aroylamino, aroyl, ar(lower)alkoxy, aryloxycarbonyl and aralkyl groups may be aromatic hydrocarbon residues having 6 to 12 carbon atoms. Suitable examples are phenyl and naphthyl.

Suitable heterocyclic groups in the term of the heterocyclylcarbonyl and heterocyclyloxycarbonyl groups may include mono- or poly-cyclic groups containing at least one hetero atom selected from nitrogen, sulfur and oxygen atoms, such as (1) unsaturated 3 to 7-membered, preferably 5 or 6-membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl or 2H-1,2,3-triazolyl], tetrazolyl [e.g., 1H-tetrazolyl or 2H-tetrazolyl] or the like.;

(2) unsaturated 3 to 7-membered, preferably 5 or 6-membered heteromonocyclic groups containing an oxygen atom, for example, furyl, pyranyl or the like;

(3) unsaturated 3 to 7-membered, preferably 5 or 6-membered heteromonocyclic groups containing 1 to 2 sulfur atoms, for example, thienyl, thiopyranyl or the like;

(4) unsaturated 3 to 7-membered, preferably 5 or 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl or 1,2,5-oxadiazolyl] or the like;

(5) unsaturated 3 to 7-membered, preferably 5 or 6-membered heteromonocyclic groups containing 1 to 2 sulfur atoms and 1 to 3 nitrogen atoms, for example, thiazolyl, thiadiazolyl [e.g., 1,2,3-thiadiazolyl, 1,2,4-thiadiazolyl, 1,3,4-thiadiazolyl or 1,2,5-thiadiazolyl] or the like;

(6) unsaturated condensed heterocyclic groups containing 1 to 2 nitrogen atoms, for example, indolyl, indazolyl, quinolyl, isoquinolyl, quinazolinyl, quinoxalinyl, benzimidazolyl or the like;

(7) unsaturated condensed heterocyclic groups containing 1 to 2 oxygen atoms, for example, benzofuryl, benzopyranyl or the like;

(8) unsaturated condensed heterocyclic groups containing 1 to 2 sulfur atoms, for example, benzo[b]thienyl or the like;

(9) unsaturated condensed heterocyclic groups containing 1 to 2 oxygen atoms and 1 to 3 nitrogen atoms, for example, benzoxazolyl, benzoxadiazolyl, phenoxazinyl or the like;

(10) unsaturated condensed heterocyclic groups containing 1 to 2 sulfur atoms and 1 to 3 nitrogen atoms, for example, benzothiazolyl, benzoisothiazolyl, phenothiazinyl or the like.

Suitable amino protective groups may include conventional amino protecting groups such as lower alkanoyls (e.g., acetyl or propionyl) and aroyls (e.g., benzoyl or naphthoyl) as explained below, ar(lower)alkyls which may have 1 to 3 suitable substituents (e.g., benzyl, 4-nitrobenzyl, phenethyl, 1-phenethyl, benzhydryl or trityl), lower alkoxy carbonyls (e.g., tert-butoxycarbonyl), ar(lower)alkoxy carbonyls (e.g., benzyloxycarbonyl or fluorenylmethoxycarbonyl).

Suitable carboxy protective groups in the term of protected carboxycarbonyl group may include conventional ones such as lower alkyl groups (e.g., methyl, ethyl, propyl, isopropyl, butyl, isobutyl, tert-butyl, pentyl, hexyl or 1-cyclopropylethyl), halo(lower)allyl groups (e.g., 2-iodomethyl or 2,2,2-trichloroethyl), ar(lower)alxyl groups (e.g., benzyl, trityl, 4-methoxybenzyl, 4-nitrobenzyl, phenethyl, bis(methoxyphenyl)methyl, 3,4-dimethoxybenzyl or 4-hydroxy-3,5-di-tert-butylbenzyl), aryl groups (e.g., phenyl, naphthyl, tolyl or xylyl). Among the above, more suitable ones are lower alkyl groups such as methyl, ethyl or tert-butyl and ar(lower)alkyl groups such as benzyl.

Suitable examples of each group are illustrated in the following in more detail.

Suitable lower alkylene groups may include straight or branched ones having 1 to 6 carbon atoms, such as methylene, methylmethylene, ethylene, methylethylene, trimethylene, tetramethylene, 2-methyltrimethylene, pentamethylene, hexamethylene and the like, more suitably the ones having 1 to 3 carbon atoms such as methylene, ethylene and trimethylene.

Suitable lower alkenylene groups may include straight or branched ones having 2 to 6 carbon atoms, such as vinylene, propenylene, butenylene, pentenylene, hexenylene and the like.

Suitable lower alkanoyl groups may include formyl, acetyl, propionyl, butyryl, iso-butyryl, valeryl, isovaleryl, n-heptanoyl, oxalyl, succinyl and pivaloyl.

Suitable lower alkanoylamino groups may include formylamino, acetylamino, propionylamino, butyrylamino, isobutyrylamino, valerylamino, isovalerylamino, 4-methypentanoylamino, isopentanoylamino, n-heptanoylaznino, oxalylamino, succinylamino and pivaloylamino.

Suitable ar(lower)alkoxycarbonylamino groups may include phenyl($C_1$–$C_6$)alkoxycarbonylamino (e.g., benzyloxycarbonylamino or phenethyloxycarbonylamino) and naphthyl($C_1$–$C_6$)alkoxycarbonylamino (e.g., naphthylmethoxycarbonylamino or naphthylethoxycarbonylamino).

Suitable lower alkoxy groups may include methoxy, ethoxy, propoxy, butoxy, isopropoxy, isobutoxy, secbutoxy and tert-butoxy.

Suitable lower alkoxycarbonyl groups may include methoxycarbonyl, ethoxycarbonyl, propoxycarbonyl, i-propoxycarbonyl, butoxycarbonyl, t-butoxycarbonyl, i-butoxycarbonyl, pentyloxycarbonyl, isopentyloxycarbonyl, heptyloxycarbonyl and hexyloxycarbonyl.

Suitable aroylamino groups may include benzoylamino and naphthoylamino.

Suitable lower alkoxycarbonylamino groups may include methoxycarbonylamino, ethoxycarbonylamino, propoxycarbonylamino, butoxycarbonylamino, isopropoxycarbonylamino, isobutoxycarbonylamino, sec-butoxycarbonylamino and tert-butoxycarbonylamino.

Suitable ar(lower)alkoxy groups may include benzyloxy, phenethyloxy, phenylpropoxy, phenylbutoxy, phenyl-isopropoxy, phenyl-iso-butoxy, phenyl-sec-butoxy and phenyl-tert-butoxy.

Suitable lower alkanoyloxy groups may include formyloxy, acetyloxy, propionyloxy, butyryloxy, isobutyryloxy, valeryloxy, isovaleryloxy, n-heptanoyloxy, oxalyloxy, succinyloxy and pivaloyloxy.

Suitable cyclo(lower)alkyl groups may include cyclopropyl, cyclobutyl, cyclopentyl, cyclohexyl and cycloheptyl.

Suitable lower alkenyloxylcarbonyl groups may include vinyloxycarbonyl, allyloxycarbonyl and the like.

Suitable di(lower)alkylaminosulfonyl groups may include dimethylaminosulfonyl and diethylaminosulfonyl.

Suitable cycloalkanoyl groups may include cyclopropanecarbonyl, cyclobutanecarbonyl, cyclopentanecarbonyl and cyclohexanecarbonyl.

Suitable aroyl groups may include benzoyl and naphthoyl.

Suitable carbamoyl(lower)alkoxy groups may include carbamoylmethoxy, carbamoylethoxy, carbamoylpropoxy, carbamoylbutoxy, carbamoylpentyloxy adn carbamoylhexyloxy.

Suitable N-(lower)alkylcarbamoyl(lower)alkoxy groups may include N-methylcarbamoylmethoxy, N-ethylcarbamoylmethoxy, N-methylcarbamoylpropoxy, N-methylcarbamoylbutoxy, N-methylcarbamoylpentyloxy, N-methylcarbamoylhexyloxy and N-hexylcarbamoylmethoxy.

Suitable N,N-di(lower)alkylcarbamoyl(lower)alkoxy groups may include N,N-dimethylcarbamoylmethoxy, N,N-diethylcarbamoylmethoxy, N,N-dipropylcarbamoylmethoxy, N,N-di-iso-propylcarbamoylmethoxy and N,N-dibutylcarbamoylmethoxy.

Suitable carboxy(lower)alkoxy groups may include carboxypropoxy, carboxybutoxy, carboxypentyloxy, carboxyhexyloxy and carboxyheptyloxy.

Suitable lower alkoxycarbonyl(lower)alkoxy groups may include methoxycarbonylmethoxy, ethoxycarbonylmethoxy, propoxycarbonylmethoxy, butoxycarbonylmethoxy, isopropoxycarbonylmethoxy, isobutoxycarbonylmethoxy, sec-butoxycarbonylmethoxy tert-butoxycarbonylmethoxy and methoxycarbonylethoxy.

Suitable cyclo(lower)alkoxy groups may include cyclopropoxy, cyclobutoxy, cyclopentyloxy and cyclohexyloxy.

Suitable cyclo(lower)alkyl(lower)alkoxy groups may include cyclopropylmethoxy, cyclobutylmethoxy, cyclopentylmethoxy, cyclohexylmethoxy, cycloheptylmethoxy and cyclohexylethoxy.

Suitable lower alkylcarbamoyl groups may include methylcarbamoyl, ethylcarbamoyl, propylcarbamoyl, isopropylcarbamoyl, butylcarbamoyl, isobutylcarbamoyl, sec-butylcarbamoyl, tert-butylcarbamoyl, pentylcarbamoyl, isopentylcarbamoyl and hexylcarbamoyl.

Suitable aryloxycarbonyl groups may include phenoxycarbonyl, naphthoxycarbonyl, tolyloxycarbonyl and mesityloxycarbonyl.

Suitable heterocyclylcarbonyl groups may include nicotinoyl, thenoyl, furoyl and isoxazolylcarbonyl.

Suitable protected carboxycarbonyl groups may include methoxyoxalyl and ethoxyoxalyl.

Suitable heterocyclicoxycarbonyl groups may include furyloxycarbonyl, thienoyloxycarbonyl, isoxazolyloxycarbonyl, 1,2,3-thiadiazolyloxycarbonyl, pyrrolyloxycarbonyl and pyridyloxycarbonyl.

Suitable bivalent N-containing 6- to 8-membered heterocyclic groups may include piperidine-1,3-diyl, 1H-2,3,4,5,6,7-hexahydroazepin-1,3-diyl, 1H-2,5,6,7-tetrahydroazepin-1,3-diyl, 1,2,3,4,5,6,7,8-octahydroazocin-1,3-diyl, 1,2,3,6,7,8-hexahydroazocin-1,3-diyl and the like.

Specific examples of each group having substituent(s) are further illustrated in the following.

The lower alkanoyl groups substituted with amino may be 2-aminoacetyl, 3-aminopropionyl, 4-aminobutyryl, 6-aminohexanoyl, 2-amino-2-methylpropionyl and 2-propionylacetyl.

The lower alkanoyl groups substituted with lower alkanoylamino may be 2-acetylaminoacetyl, 3-acetylaminopropionyl, 4-acetylaminobutyryl and 2-propionylacetyl.

The lower alkanoyl groups substituted with ar(lower)alkoxycarbonylamino may be 2-(benzyloxycarbonylamino)-acetyl and 3-(benzyloxycarbonylamino)propionyl.

The lower alkanoyl groups substituted with aryl which may further be substituted with carboxy, lower alkoxy or lower alkoxycarbonyl may be 4-carboxyphenylacetyl, 4-methoxyphenylacetyl, 4-methoxyphenylpropionyl and 4-methoxycarbonylphenylacetyl.

The lower alkanoyl groups substituted with aroylamino which may further be substituted with carboxy, lower alkoxy or lower alkoxycarbonyl may be 2-((4-carboxybenzoyl)amino)acetyl, 2-((4-methoxycarbonybenzoyl)amino)acetyl, 3-((4-carboxybenzoyl)-amino)propionyl and 3-((4-methoxycarbonylbenzoyl)amino)-propionyl.

The lower alkanoyl groups substituted with carboxy may be carboxyacetyl, carboxypropionyl, carboxybutyryl, carboxy-iso-butyryl and carboxy-n-heptanoyl.

The lower alkanoyl groups substituted with lower alkoxycarbonylamino may be methoxycarbonylaminoacetyl, ethoxycarbonylaminoacetyl, isobutoxycarbonylaminoacetyl, isobutoxycarbonylaminopropionyl, propoxycarbonylaminoacetyl and butoxycarbonylaminopropionyl.

The lower alkanoyl groups substituted with ar(lower)alkoxy may be benzyloxyacetyl, benzyloxypropionyl, naphthylmethoxyacetyl and naphthylmethoxypropionyl.

The lower alkanoyl groups substituted with lower alkoxycarbonyl may be methoxycarbonylacetyl, methoxycarbonylpropionyl, ethoxycarbonylacetyl and propoxycarbonylpropionyl.

The lower alkanoyl groups substituted with lower alkanoyloxy may be acetyloxyacetyl, acetyloxypropionyl, propionyloxyacetyl and propionyloxypropionyl.

The lower alkanoyl groups substituted with lower alkoxy may be methoxyacetyl, methoxypropionyl, ethoxyacetyl and ethoxypropionyl.

The lower alkanoyl group substituted with hydroxy may be hydroxyacetyl, hydroxypropionyl, hydroxybutyryl and hydroxyhexanoyl.

The lower alkoxycarbonyl groups substituted with lower alkoxy may be methoxymethoxycarbonyl and 2-methoxyethoxycarbonyl.

The lower alkoxycarbonyl groups substituted with aryl may be benzyloxycarbonyl and phenethyloxycarbonyl.

The lower alkoxycarbonyl groups substituted with cyclo(lower)alkyl may be cyclopropylmethoxycarbonyl, cyclobutylmethoxycarbonyl, cyclopentylmethoxycarbonyl, cyclohexylmethoxycarbonyl, cyclopropylethoxycarbonyl, cyclobutylethoxycarbonyl, cyclopentylethoxycarbonyl and cyclohexylethoxycarbonyl.

The cycloalkanoyl groups substituted with lower alkoxy may be methoxycyclopropylcarbonyl, methoxycyclobutylcarbonyl, methoxycyclopentylcarbonyl and methoxycyclohexylcarbonyl.

The aroyl groups substituted with $C_3$–$C_6$ alkoxy may be 4-propoxybenzoyl, 4-isopropoxybenzoyl, 4-isobutoxybenzoyl, isopentyloxybenzoyl, isohexyloxybenzoyl and neopentyloxybenzoyl.

The aroyl groups substituted with carbamoyl(lower)alkoxy may be 4-carbamoylmethoxybenzoyl and 4-carbamoylethyloxybenzoyl.

The aroyl groups substituted with N-(lower)alkylcarbamoyl(lower)alkoxy may be 4-(N-methylcarbamoylmethoxy)benzoyl, 4-(N-ethylcarbamoylmethoxy)benzoyl, 4-(N-isopropylcarbamoylmethoxy)benzoyl, 4-(N-n-butylcarbamoylmethoxy)benzoyl, 3-(isobutylcarbamoylmaethoxy)benzoyl and 4-(isobutylcarbamoylmethoxy)benzoyl.

The aroyl groups substituted with N,N-di(lower)alkylcarbamoyl(lower)alkoxy may be 4-(N,N-dimethylcarbamoylmethoxy)benzoyl, 4-(N,N-diethylcarbamoylmethoxy)benzoyl, 4-(N,N-dipropylcarbamoylmethoxy)benzoyl, 4-(N,N-di-isopropylcarbamoylmethoxy)benzoyl and 4-(N,N-dibutylcarbamoylmethoxy)benzoyl.

The aroyl groups substituted with lower alkoxycarbonyl may be methoxycarbonylbenzoyl, ethoxycarbonylbenzoyl, propoxycarbonylbenzoyl, iso-propoxycarbonylbenzoyl, butoxycarbonylbenzoyl, tert-butoxycarbonylbenzoyl and methoxycarbonylnaphthoyl.

The aroyl groups substituted with nitro may be nitrobenzoyl and nitronaphthoyl.

The aroyl groups substituted with cyano may be cycanobenzoyl and cycanonaphthoyl.

The aroyl groups substituted with carboxy may be carboxybenzoyl and carboxynaphthoyl.

The aroyl groups substituted with carboxy(lower)alkoxy may be carboxypropoxybenzoyl, carboxybutoxybenzoyl, carboxypentoxybenzoyl and carboxyhexyloxybenzoyl.

The aroyl groups substituted with ar(lower)alkoxy may be benzyloxybenzoyl, phenethyloxybenzoyl, phenylpropoxybenzoyl, phenylbutoxybenzoyl and phenylisopropoxybenzoyl.

The aroyl groups substituted with lower alkoxycarbonyl(lower)alkoxy may be methoxycarbonylmethoxybenzoyl, ethoxycarbonylmethoxybenzoyl, propoxycarbonylmethoxybenzoyl and butoxycarbonylmethoxybenzoyl.

The aroyl groups substituted with cyclo(lower)alkoxy may be cyclopropoxybenzoyl, cyclobutoxybenzoyl and cyclopentoxybenzoyl.

The aroyl groups substituted with lower alkoxycarbonylamino may be methoxycarbonylaminobenzoyl and ethoxycarbonylaminobenzoyl.

The aroyl groups substituted with cyclo(lower)alkyl(lower)-alkoxy may be cyclopropylmethoxybenzoyl, cyclobutylmethoxybenzoyl and cyclopentylmethoxybenzoyl.

The aroyl groups substituted with lower alkanoylamino may be formylaminobenzoyl, acetylaminobenzoyl, propionylaminobenzoyl and butyrylaminobenzoyl.

The aroyl groups substituted with lower alkylcarbamoyl may be methylcarbamoylbenzoyl, ethylcarbamoylbenzoyl and propylcarbamoylbenzoyl.

The aryl groups substituted with hydroxy may be 3-hydroxyphenyl, 4-hydroxyphenyl and 3,4-dihydroxyphenyl.

The aryl groups substituted with lower alkoxy may be 2-methoxyphenyl, 3-methoxyohenyl, 4-methoxyphenyl, 3,4-dimethoxyphenyl, 4-(2,2-dimethyl)propoxyphenyl, 3-isobutoxyphenyl, 4-isobutoxyphenyl and 4-(2-methyl)pentoxyphenyl.

The aralkyl groups substituted with hydroxy may be 4-hydroxybenzyl, 3,4-dihydroxybenzyl and 4-hydrozyphenethyl.

The aralkyl groups substituted with lower alkoxy may be 4-methoxybenzyl, 3,4-dimethoxybenzyl, 4-methoxyphenethyl and 3,4-dimethoxyphenethyl.

Preferred embodiment of the object compounds are derivatives of the formula (I), wherein $R^1$ is hydrogen, A is a lower alkylene group, $R^2$ is an amino group which is substituted with an aroyl group substituted with lower alkylcarbamoyl, $R^3$ is hydrogen atom and the moiety represented by the formula:

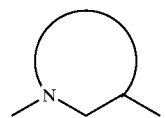

is piperidine-1,3-diyl.

More preferred embodiment of the object compounds are derivatives of the formula (I), wherein $R^1$ is hydrogen, A is ethylene group, $R^2$ is an amino group which is substituted with a benzoyl group substituted with lower alkylcarbamoyl, $R^3$ is hydrogen atom and the moiety represented by the formula:

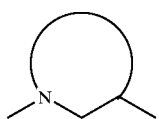

is piperidine-1,3-diyl.

Suitable salts of the compounds (I) are conventional non-toxic pharmaceutically acceptable salts and may be salts with inorganic bases, for example, an alkali metal (e.g. sodium or potassium), an alkaline earth metal (e.g. calcium or magnesium), ammonium; a salt with an organic base, for example, an organic amine (e.g. triethylamine, pyridine, picoline, ethanolamine, triethanolamine, dicyclohexylamine, or N,N'-dibenzylethylenediamine); an inorganic acid addition salt (e.g. hydrochloride, hydrobromide, hydroiodide, sulfate or phosphate); an organic carboxylic or sulfonic acid addition salt (e.g. formate, acetate, trifluoroacetate, maleate, tartrate, methanesulfonate, benzenesulfonate or p-toluenesulfonate); a salt with a basic or acidic amino acid (e.g. arginine, aspartate or glutamate); and the like, and preferable examples thereof are the acid addition salts.

The compounds (I) may contain one or more asymmetric centers and thus they can exist as enantiomers or diastereoisomers.

The compounds (I) may also exist in tautomeric forms, and accordingly the present invention includes both of mixtures and separated individual tautomers.

It is further to be noted that isomerization or rearrangement of the compounds (I) may occur by the effect of light, acid, base or the like, and the compounds obtained as the result of said isomerization or rearrangement are also included within the scope of the present invention.

The compounds (I) and their salts can be in a form of a solvate, which is included within the scope of the present invention. The solvate preferably include a hydrate and an ethanolate.

Also included in the scope of the invention are radiolabelled derivatives of the compounds (I) which are suitable for biological studies.

An compound (I) or a salt thereof can be prepared by the following processes.

Process 1

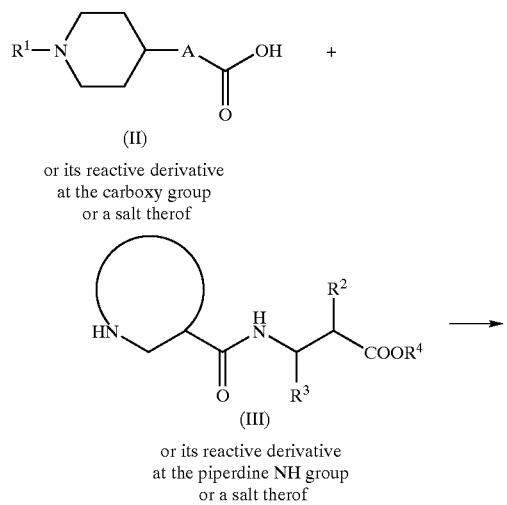

Process 2

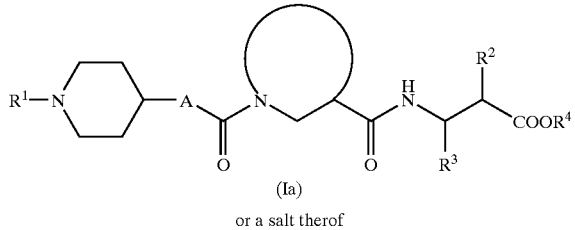

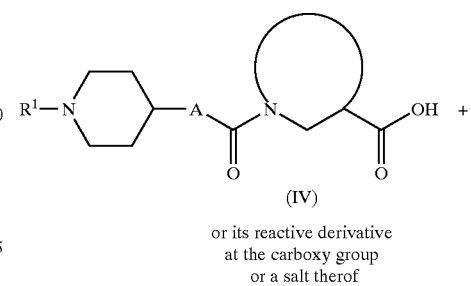

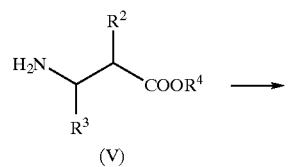

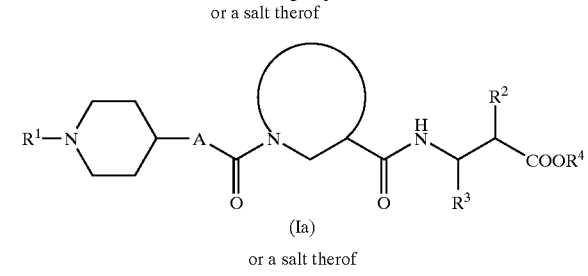

Process 3

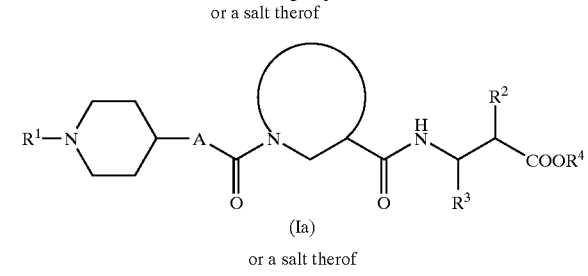

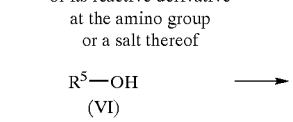

or its reactive derivative
at the carboxy group
or a salt thereof

-continued

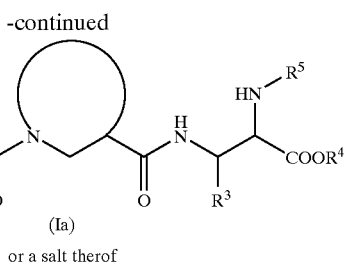

(Ia)

or a salt therof

Process 4

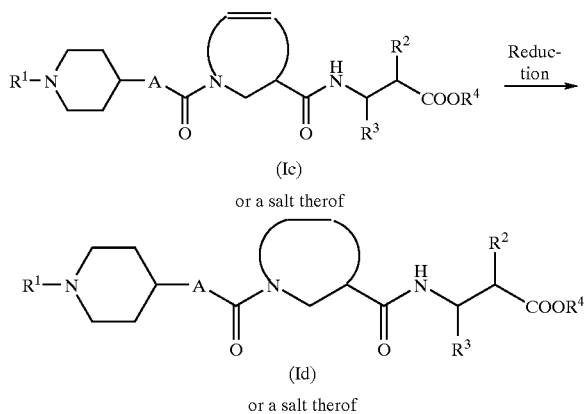

wherein $R^1$, $R^2$, $R^3$ and A are each as defined above,
$R^4$ is hydrogen atom or a carboxy protective group,
$R^5$ is an acyl group as defined above, the moiety of

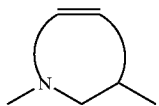

is a bivalent N-containing 6- to 8-membered heterocyclic group containing one double bond and
the moiety of

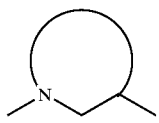

is a bivalent N-containing 6- to 8-membered saturated heterocyclic group.

The processes for preparing the object compound (I) of the present invention are explained in detail in the following.

Process 1

The compound (Ia) or a salt thereof can be prepared by reacting the compound (II) or its reactive derivative at the carboxy group or a salt thereof with the compound (III) or its reactive derivative at the piperidine NH group or a salt thereof.

Suitable reactive derivative at the carboxy group of the compound (II) may include an acid halide, an acid anhydride, an activated amide, an activated ester and the like. Examples of the suitable reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid or halogenated phosphoric acid], dialkylphospohrous acid, sulfurous acid, thiosulfuric acid, sulfuric acid, sulfonic acid [e.g., methanesulfonic acid], aliphatic carboxylic acid [e.g., acetic acid, propionic acid, butyric acid, isobutyric acid, pivalic acid, pentanoic acid, isopentanoic acid, 2-ethylbutyric acid or trichloroacetic acid] or aromatic carboxylic acid [e.g., benzoic acid]; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [$(CH_3)_2N^+$=C—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester or 8-quinolyl thioester], or an ester with a N-hydroxy compound [e.g., N,N-dimethylhydroxylamine, 1-hydroxy-2-(1H)-pyridone, N-hydroxysuccinimide, N-hydroxyphthalimide or 1-hydroxy-1H-benzotriazole] and the like. A reactive derivative can be optionally selected from the above according to the kind of the compound (II) to be used.

Suitable salts of the compound (II) or its reactive derivative can be referred to those as exemplified for the compound (I).

Suitable reactive derivative at the piperidine NH group of the compound (III) may include Shiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by the reaction of the compound (III) with phosphorus trichloride or phosgene, and the like.

Suitable salts of the compound (III) or its reactive derivative can be referred to those as exemplified for the compound (I).

The reaction is usually carried out in a conventional solvent such as water, alcohol [e.g., methanol or ethanol], acetone, dioxane, acetonitrile, chloroform, methylene chloride, ethylene chloride, tetrahydrofuran, ethyl acetate, N,N-dimethylformamide, pyridine or any other organic solvent which dose not adversely affect the reaction. These conventional solvents may also be used in a mixture with water.

In this reaction, when the compound (II) is used in a free acid form or its salt form, the reaction is preferable carried out in the presence of a conventional condensing agent such as N,N'-dicyclohexyl-carbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkylphosphite; ethyl polyphosphate; isopropyl polyphosphate; phosphorous oxychloride (phosphoryl chloride); phosphorous trichloride; thionyl chloride; oxalyl chloride; lower alkyl haloformate [e.g., ethyl chloroformate or isopropyl chloroformate]; triphenylphosphine; 2-ethyl-7-hydroxybenzisoxazolium salt; 2-ethyl-5-(m-sulfophenyl) isoxazolium hydroxide intramolecular salt; 1-(p-chlorobenzensulfonyloxy)-6-chloro-1H-benzotriazole;

so-called Vilsmeier reagent prepared by the reaction of N,N-dimethylformamide with thionyl chloride, phosgene, trichloromethyl chloroformate, phosphorous oxychloride, methanesulfonyl chloride, etc; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower))alkylbenzylamine or the like.

The reaction is usually carried out under cooling to warming, although the reaction temperature is not critical.

Process 2

The compound (Ia) or a salt thereof can be prepared by reacting the compound (IV) or its reactive derivative at the carboxy group or a salt thereof with the compound (V) or its reactive derivative at the amino group or a salt thereof.

The reaction can be carried out in a similar manner to that of Process 1 mentioned in the above, and therefore the reaction mode and reaction conditions [e.g., reactive derivative, solvent or reaction temperature] of this reaction are to be referred to those as explained in the above Process 1.

Process 3

The compound (Ia) or a salt thereof can be prepared by reacting the compound (Ib) or its reactive derivative at the amino group or a salt thereof with the compound (VI) or its reactive derivative at the carboxy group or a salt thereof.

This reaction is carried out according to a conventional manner such as the ones described in the above Process 1 or similar manners thereto.

Process 4

The compound (Id) or a salt thereof can be prepared by subjecting a compound (Ic) or a salt thereof to reduction, i.e., chemical reduction or catalytic reduction.

Suitable reducing agents to be used in chemical reduction may be a combination of metal [e.g., tin, zinc or iron] or metallic compound [e.g., chromium chloride or chromium acetate] and an organic or inorganic acid [e.g.; formic acid, acetic acid, propionic acid, trifluoroacetic acid, p-toluenesulfonic acid, hydrochloric acid or hydrobromic acid].

Suitable catalysts to be used in catalytic reduction may be conventional ones such as a platinum catalyst [e.g., platinum plate, spongy platinum, platinum black, colloidal platinum, platinum oxide or platinum wire], a palladium catalyst [e.g., spongy palladium, palladium black, palladium oxide, palladium on carbon, colloidal palladium, palladium on black, palladium on sulfate or palladium on barium carbonate], a nickel catalyst [e.g., reduced nickel, nickel oxide or Raney nickel], a cobalt catalyst [e.g., reduced cobalt or Raney cobalt], an iron catalyst [e.g., reduced iron or Raney iron], a copper catalyst [e.g., reduced copper, Raney copper or Ullman copper] and the like.

A suitable solvent to be used in the chemical reduction may be a conventional solvent which does not adversely affect the reaction such as water, methanol, ethanol, propanol, N,N-dimethylformamide or a mixture thereof.

Further, a suitable solvent to be used in the catalytic reduction may be the above-mentioned solvent, and other conventional solvent such as diethyl ether, dioxane, tetrahydrofuran or a mixture thereof.

The reaction is usually carried out under cooling to warming, although the reaction temperature is not critical.

If desired, the amino protective group of $R^1$ and/or carboxy protective group of $R^2$ and/or $R^4$ may be removed by a conventional manner known in the art. The removal of each protective group can be conducted separately or all at once.

The removal methods of the protective group can be selected in accordance with the kinds of the protective groups and the typical methods are hydrolysis with an acid or base or reduction such as catalytic reduction and chemical reduction.

The hydrolysis is preferably carried out in the presence of a base or an acid including Lewis acid.

Suitable base may include an inorganic base and an organic base such as an alkali metal [e.g., sodium or potassium], an alkaline earth metal (e.g., calcium or magnesium), an alkali metal hydroxide [e.g., sodium hydroxide or potassium hydroxide], an alkali metal hydrogen carbonate [(e.g., sodium hydrogencarbonate or potassium hydrogen carbonate], an alkali metal carbonate [e.g., sodium carbonate], an alkali earth metal carbonate [e.g., calcium carbonate], triallylamine [e.g., trimethylamine, triethylamine, N,N-diisopropylethylamine or dibenzylethylenediamine], picoline, 1,5-dizazbicyclo[4.3.0] non-5-ene, 1,4-diazabicyclo[2.2.2]octane, 1,8-diazabicyclo [5.4.0]undec-7-ene or the like.

Suitable acid may include an organic acid [e.g., formic acid, acetic acid, propionic acid, trichloroacetic acid or trifluoroacetic acid] and an inorganic acid [e.g., hydrochloric acid, hydrobromic acid, sulfuric acid, hydrogen chloride or hydrogen bromide].

The removal reaction of the protective group using Lewis acid such as trihaloacetic acid [e.g., trichloroacetic acid or trifluoroacetic acid] or the like is preferably carried out in the presence of a cation trapping agent [e.g., anisole or phenol].

The removal reaction is usually carried out in a solvent such as water, an alcohol [e.g., methanol or ethanol], methylene chloride, tetrahydrofuran, a mixture thereof or any other solvent which does not adversely affect the reaction. A liquid base or acid can be also used as a solvent. The reaction temperature is not critical and the reaction is usually carried out under cooling to warming.

The reduction method applicable for the removal reaction may include chemical reduction and catalytic reduction as described above.

The compounds (I) of the present invention can be isolated and purified in a conventional manner, for example, extraction, precipitation, fractional crystallization, recrystallization, chromatography or the like.

A pharmaceutically acceptable salt of the compound (I) can be prepared by treating a compound (I) with an appropriate base or acid in accordance with the conventional method.

The compounds (I) and salts thereof may be solvates (e.g., hydrate or ethanolate) or inclusion compounds which can be prepared by using a conventional host compound such as β-cyclodextrin.

The starting compounds (II), (III), (IV), (V) and (VI) can be obtained by purchasing commercial products or preparing them according to the methods disclosed is WO96/29309 or the method described in the following Examples or similar method thereto.

In order to exhibit the utility of the compound (I) of the present invention, their activities are shown in the following.
Test: Effect on Platelet Aggregation Induced by Adenosine Diphosphate (ADP)
Test Compound
  The Compound of Example 25
Test Method
  Platelet rich plasma (PRP) which contains $3\times10^8$ platelets/ml was prepared from human blood. To the 225 µl of PRP, 25 µl of the solution of the test compound in water was added, and then stirred for 2 minutes at 37° C. To the solution 5 μl of ADP (final 2.5 μM) was added as an aggregation inducer. Aggregation was measured by using an aggregometor (NBS HEMA-TRACER 801). Activity of inducer (test compound) was expressed as $IC_{50}$ value, i.e., dose required for complete inhibition of platelet aggregation.

TABLE 1

| Test compound | $IC_{50}(\mu M)$ |
|---|---|
| Example 25 | 0.085 |

As shown in the above table 1, the compound (I) of the present invention has inhibitory activity against platelet aggregation.

As shown in the above, the compounds (I) of the present invention may exhibit pharmacological activities as a fibrinogen receptor antagonist. Therefore, the compounds (I) of the invention are useful as a glycoprotein IIb/IIIa antagonist and an inhibitor of platelet aggregation, especially as:

a drug for prevention and/or treatment of diseases caused by thrombus formation such as arterial thrombosis, arterial sclerosis, ischemic heart diseases [e.g., angina pectoris (e.g., stable angina pectoris or unstable angina pectoris including imminent infraction), myocardial infarction (e.g., acute myocardial infarction) or coronary thrombosis], ischemic brain diseases [e.g., cerebral infarction {e.g., cerebral thrombosis (e.g., acute cerebral thrombosis) or cerebral embolism}, transient cerebral ischemia (e.g., transient ischemic attack) or cerebrovascular spasm after cerebral hemorrhage (e.g., cerebrovascular spasm after subarachnoid hemorrhage)], pulmonary vascular diseases (e.g., pulmonary thrombosis or pulmonary embolism), peripheral circulatory disorder [e.g., arteriosclerosis obliterans, thromboangiitis obliterans (i.e., Bürger's disease), Raynaud's disease, complication of diabetes mellitus (e.g., diabetic angiopathy or diabetic neuropathy) or phlebothrombosis (e.g., deep vein thrombosis)], a drug for prevention and/or treatment of diseases such as conjunctive diseases [e.g., conjunctivitis (e.g., allergic conjunctivitis, vernal conjunctiviti, keratoconjunctivitis sicca, viral conjunctivitis and bactterial conjunctivitis)], uveal diseases [e.g., unveitis (e.g., Behcet disease, haradadisease, sympathetic opthalmia, sarcoidosis and diabetic iritis)], scieral diseases [e.g., scleritis], corneal deseases [e.g., corneal neocascularization, keratitis, corneal edema, corneal opacity, corneal dystrophy, keratoconus and neuroparalytic keratitis], retinal or vitreous diseases [e.g., diabetic retinopathy, retinal artery occlusion, retinal vein occlusion, central setous chorioretinopathy, central hemorrhagic chorioretinitis, macular degeneration, retinal detachment, retinal pigmentary degeneration, macular neovascularization, macular hole, proliferative vitreoretinopathy, vitreous hemorrhage and vitreous opacity], lens disease [e.g., cataract (e.g., senile cataract, traumatic cataract, diabetic cataract and atopic cataract)], glaucoma [e.g., primary open-angle glaucoma, primary angle-closure galucoma, normal tension glaucoma and neovascular galucoma], ocular hypertension, vision disorders [e.g., amblyopia, color vision defect and night blindeness], referactive errors [e.g., astigmatism, hyperopia, myopia and presbyopia], lacrimal apparatus diseases [e.g., dry eye syndromes, lacrimal duct obstraction and dacryocystitis] or the like;

a drug for prevention and/or treatment of restenosis and/or reocclusion such as restenosis and/or reocclusion after percutaneous transluminal coronary angioplasty (PTCA), restenosis and/or recclusion after the administration of thrombolytic drug (e.g., tissue plasminogen activator (TPA)) or the like;

a drug for adjuvant therapy with thrombolytic drug (e.g., TPA) or anticoagulant (e.g., heparin);

a drug for prevention and/or treatment of the thrombus formation in case of vascular surgery, valve replacement, extracorporeal circulation [e.g., surgery (e.g., open heart surgery or pump-oxygenator) or hemodialysis], transplantation or the like;

a drug for prevention and/or treatment of disseminated intravascular coagulation (DIC), thrombotic thrombocytopenia, essential thrombocytosis, inflammation (e.g., nephritis), immune diseases or the like;

a drug for inhibiting metastasis; or the like.

The present invention also provides a pharmaceutical composition which comprises, as an active ingredient, a compound (I) of the present invention or a pharmaceutically acceptable salt thereof in admixture with a pharmaceutically acceptable carrier.

The pharmaceutical composition of the present invention can be used for prevention and/or treatment of a disease caused by thrombus formation; restenosis or reocclusion; thrombus formation in the case of vascular surgery, valve replacement, extracorporeal circulation or transplantation; disseminated intravascular coagulation; thrombotic thrombocytopenic; essential thrombocytosis; inflammation; immune disease; or metastasis;

or for adjuvant therapy with a thrombolytic drug or anticoagulant.

The pharmaceutical composition of the present invention may be in solid, semisolid or liquid form, which contains a compound (I), as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. Examples of organic or inorganic carrier or excipient are the usual non-toxic, pharmaceutically acceptable ones for tablets, pellets, troches, capsules, suppositories, creams, ointments, aerosols, powders for insufflation, solutions, emulsions, suspensions and any other form suitable for use. And, if necessary, in addition, auxiliary, stabilizing, thickening and coloring agents and perfumes may be used.

The pharmaceutical composition of the present invention can be manufactured by a conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, pulmonary, or oral administration, or insufflation including aerosols from metered dose inhalator, nebulizer or drug powder inhalator.

While the dosage of therapeutically effective amount of the compound (I) varies from and also depends upon the age and condition of each individual patient to be treated, in the case of intravenous administration, a daily dose of 0.001–10 mg of the compound (I) per kg weight of a human being or an animal, in the case of intramuscular administration, a daily dose of 0.001–100 mg of the compound(I) per kg weight of a human being or an animal, in case of oral administration, a daily dose of 0.001–200 mg of the compound(I) per kg weight of a human being or an animal in generally given for the prevention and/or treatment of aforementioned diseases in a human being or an animal.

The pharmaceutical composition comprises the derivative (I) in an amount sufficient to produce the desired effect upon the process or condition of the diseases.

According to the present invention, the compound (I) of the invention or pharmaceutically acceptable salt thereof can be used as a medicament for the manufacture of a medicament having an activity of fibrinogen receptor antagonist.

The present invention further provide a method for prevention of a disease caused by thrombus formation; restenosis or reocclusion; thrombus formation in the case of vascular surgery, valve replacement, extracorporeal circulation or transplantation; disseminated intravascular coagulation; thrombotic thrombocytopenic; essential thrombocytosis; inflammation; immune disease; or metastasis; which comprises administering the derivative of the formula (I) or a pharmaceutically acceptable salt thereof to a human being or an animal.

The present invention still further provide a method for treatment of a disease caused by thrombus formation; restenosis or reocclusion; thrombus formation in the case of vascular surgery, valve replacement, extracorporeal circulation or transplantation; disseminated intravascular coagulation; thrombotic thrombocytopenic; essential thrombocytosis; inflammation; immune disease; or metastasis; which comprises administering the derivative of the formula (I) or a pharmaceutically acceptable salt thereof to a human being or an animal suffering any of the above disease.

The present still further provide a method for adjuvant therapy with a thrombolytic drug or anticoagulant; which comprises administering the derivative of the formula (I) or a pharmaceutically acceptable salt thereof to a human being or an animal suffering a disease to be treated with the thrombolytic drug or anticoagulant.

The following Examples are given for illustrating the present invention in more detail, but it is to be noted that the scope of the present invention is not limited by these Examples.

BEST MODE FOR CARRYING OUT THE INVENTION

The following Examples are given only for the purpose of illustrating the present invention in more detail.

Preparation 1

To a solution of 2-tert-butoxycarbonylamino-2-methylpropionic acid (2.03 g) and 1-hydroxybenzotriazole (1.35 g) in N,N-dimethylfolmamide (20 mL) was added 1-ethyl-3-(3-dimethylaminopropyl)carbodiimide hydrochloride (1.91 g) and the mixture was stirred overnight. The reaction mixture was partitioned between a mixture of ethyl acetate and n-hexane and water. The separated organic layer was washed in turn with water, a saturated sodium hydrogencarbonate in water and brine and dried over magnesium sulfate. The organic layer was evaporated under reduced pressure to give benzotriazol-1-yl 2-tert-butoxycarbonylamino-2-methylpropionate (2.94 g, 91.9%) as a solid.

IR (KBr) 3398, 2989, 1803, 1691, 1510 cm$^{-1}$;

$^1$H-NMR (DMSO-d$_6$, δ): 1.48 (9H, s), 1.610 (6H, s), 7.50–7.60 (1H, m), 7.65–7.85 (2H, m), 8.05–8.20 (2H, m).

Preparation 2

The following compounds described in (1) and (2) were obtained in a manner similar to Preparation 1.

(1) Benzotriazol-1-yl 2-(benzyloxycarbonylamino) acetate

IR (KBr) 3431, 1751, 1720, 1517 cm$^{-1}$;

$^1$H-NMR (DMSO-d$_6$, δ): 3.10–3.20 (2H, m), 3.40–3.55 (2H, m), 5.07 (2H, s), 7.20–8.40 (10H, m).

(2) Benzotriazol-1-yl 3-(benzyloxycarbonylamino) propionate

IR (KBr) 3336, 1731, 1664, 1547 cm$^{-1}$;

$^1$H-NMR (DMSO-d$_6$, δ): 4.45–4.60 (2H, m), 5.10–5.15 (2H, m), 7.20–8.40 (10H, m).

Preparation 3

To a mixture of methyl 4-hydroxybenzoate (15.2 g) and potassium carbonate (15.2 g) in N,N-dimethylformamide (150 mL) was added dropwise benzyl bromoacetate (15.6 mL) at ambient temperature, and the mixture was stirred overnight. The reaction mixture was partitioned between a mixture of ethyl acetate and n-hexane and water. The separated organic layer was washed in turn with 20% aqueous potassium carbonate solution and brine, dried over magnesium sulfate and evaporated to give benzyl (4-methoxycarbonyl)phenoxyacetate (29 g, 98.6%) as an oil.

IR (KBr) 1757, 1707, 1608, 1510 cm$^{-1}$;

$^1$H-NMR (CDCl$_3$, δ): 3.88 (3H, s), 4.71 (2H, s), 5.24 (2H, s), 6.85–6.95 (2H, m), 7.30 (5H, s), 7.90–8.05 (2H, m);

(+)-APCI/MS (m/z): 301 (M+H)$^+$.

Preparation 4

Benzyl (4-methoxycarbonyl)phenoxyacetate (28.5 g) was hydrogenated over 10% palladium on carbon (50% wet, 5.7 g) in methanol (400 mL) under an atmospheric pressure of hydrogen at ambient temperature. After 3 hours, the catalyst was removed by filtration and the filtrate was evaporated to give (4-methoxycarbonyl)phenoxyacetic acid (19.78 g, 99.2%) as a white solid.

IR (KBr) 1736, 1711, 1604, 1512 cm$^{-1}$;

$^1$H-NMR (CDCl$_3$, δ): 3.90 (3H, s), 4.75 (2H, s), 6.95 (2H, d, J=8.9 Hz), 8.02 (2H, d, J=8.9 Hz);

(+)-APCI/MS (m/z): 211 (M+H)$^+$.

Preparation 5

A mixture of (4-methoxycarbonyl)phenoxyacetic acid (2.1 g), 1-hydroxybenzotriazole (1.49 g) and ammonium chloride (590 mg) in N,N-diamethylformamide (40 mL) was added 1-ethyl-3-(3-dimethylaminopropyl)carbodiimide (2 mL) at ambient temperature, and the mixture was stirred ovenight. After 3 days, the reaction mixture was partitioned between a mixture of ethyl acetate and n-hexane and water. The separated organic layer was washed in turn with water, a saturated sodium hydrogencarbonate in water, brine, 0.1 N-aqueous hydrochloric acid, brine, a saturated sodium hydrogencarbonate in water and brine. The organic layer was dried over magnesium sulfate and evaporated to give methyl 4-(carbamoylmethoxy)benzoate (760 mg, 36.4%) as a white solid.

IR (KBr) 1711, 1672, 1599, 1512 cm$^{-1}$;

$^1$H-NMR (DMSO-d$_6$, δ): 3.33 (3H, s), 4.53 (2H, s), 7.00–7.10 (2H, m), 7.42 (1H, brs), 7.59 (1H, brs), 7.85–7.95 (2H, m);

(+)-APCI/MS (m/z): 210 (M+H)$^+$.

Preparation 6

Methyl (4-N-methylcarbamoylmethoxy)benzoate was obtained in a manner similar to Preparation 5.

IR (KBr) 1712, 1653, 1604, 1554, 1508 cm$^{-1}$;

$^1$H-NMR (DMSO-d$_6$, δ): 2.26 (3H, d, J=4.7 Hz), 3.33 (3H, s), 4.56 (2H, s), 7.00–7.10 (2H, m), 7.88–7.98 (2H, m), 8.10 (1H, brs);

(+)-APCI/MS (m/z): 224 (M+H)$^+$.

Preparation 7

A mixture of methyl (4-carbamoylmethoxy)benzoate (740 mg) and 1 N-aqueous sodium hydroxide solution (14.2 mL) in methanol (20 mL) was stirred overnight at ambient temperature. After evaporation of the solvent, the residue was dissolved in water. The solution was washed with ethyl acetate and acidified with 20% aqueous potassium hydrogensulfate solution. The resulting insoluble solid was collected by filtration, washed with water and dried to give (4-carbamoylmethoxy)benzoic acid (630 mg, 91.2%) as a white solid.

IR (KBr) 1738, 1712, 1678, 1606, 1579, 1512 cm$^{-1}$;
$^1$H-NMR (DMSO-d$_6$, δ): 4.77 (2H, s), 6.95–7.05 (2H, m), 7.84–7.92 (2H, m), 12.87 (1H, brs);
(+)–APCI/MS (m/z): 196 (M+H)$^+$.

Preparation 8

(4-N-Methylcarbamoylmethoxy)benzoic acid was obtained in a manner similar to Preparation 7.

IR (KBr) 1676, 1660, 1606, 1581, 1549, 1512 cm$^{-1}$;
$^1$H-NMR (DMSO-d$_6$, δ): 2.66 (3H, d, J=4.6 Hz), 4.55 (2H, s), 6.95–7.10 (2H, m), 7.85–7.95 (2H, m), 8.08 (1H, brs), 12.71 (1H, brs);
(+)–APCI/MS (m/z): 210 (M+H)$^+$.

Preparation 9

Allyl amine (0.83 mL, 11.1 mmol) was added to a solution of ethyl acrylate (1.0 mL, 9.23 mmol) in ethanol (10 mL). The mixture was stirred overnight at room temperature, then evaporated in vacuo. The residue was dissolved in dichloromethane (10 mL), and di-tert-butyl dicarbonate (DIBOC) (2.55 mL, 11.1 mmol) was added thereto. The mixture was stirred overnight at room temperature, then evaporated in vacuo. The residue was purified by a silica gel column chromatography eluting with a mixture of ethyl acetate and n-hexane (1:20) to give ethyl N-(tert-butoxycarbonyl)-3-(2-propenylamino)propionate (1.87 g, 7.27 mmol, 78.7%) as a colourless oil.

IR (film) 2979, 1735, 1698, 1463, 1409 cm$^{-1}$;
$^1$H-NMR (CDCl$_3$, δ): 1.26 (3H, t, J=7.0 Hz), 1.45 (9H, s), 2.51–2.59 (2H, m), 3.43–3.50 (2H, m), 3.83–3.85 (2H, m), 4.12 (2H, q, J=7.0 Hz), 5.09–5.15 (2H, m), 5.67–5.84 (1H, m);
MASS (m/z): 280 [M+Na]$^+$ Preparation 10

To a solution of ethyl N-(tert-butoxycarbonyl)-3-(2-propenylamino)propionate (1.12 g, 4.86 mmol) was added 1N solution of lithium bis(trimethylsilyl)amide in tetrahydrofuran (THF) (5.8 mL) and allyl bromide (1.46 mL, 17.0 mmol) successively at −78° C. The mixture was stirred at 0° C. for an hour, then quenched by a saturated aqueous NH$_4$Cl solution and extracted with ethyl acetate. The extract was washed with water and brine, dried over Na$_2$SO$_4$, and evaporated in vacuo. The residue was purified by a silica gel column chromatography eluting with a mixture of ethyl acetate and n-hexane (1:20) to give ethyl N-(tert-butoxycarbonyl)-2-(2-propenyl)-3-(2-propenylamino) propionate (0.7 g, 2.35 mmol, 48.4%) as a colourless oil.

IR (film) 2979, 1733, 1699, 1462, 1405 cm$^{-1}$;
$^1$H-NMR(CDCl$_3$, δ): 1.28 (3H, t, J=7.1 Hz), 1.45 (9H, s), 2.09–2.41 (2H, m), 2.84 (1H, br), 3.23–3.34 (2H, m), 3.46–4.02 (2H, m), 4.13 (2H, q, J=7.1 Hz), 5.00–5.14 (4H, m), 5.64–5.84 (2H, m);
$^{13}$C-NMR(CDCl$_3$, δ): 14.26, 28.05, 34.47, 44.50, 48.31, 50.80, 60.53, 79.9, 117.12, 133.90, 134.77, 155.45, 174.34;
MASS (m/z): 297 [M]$^+$.

Preparation 11

The following compounds (1) to (3) were obtained in a manner similar to Preparation 10.

(1) Ethyl N-(tert-butoxycarbonyl)-2-(2-propenyl)-3-(4-butenylamino)propionate

IR (film) 2978, 1734, 1698, 1643, 1473, 1413 cm$^{-1}$;
$^1$H-NMR(CDCl$_3$, δ): 1.25 (3H, t, J=7.1 Hz), 1.46 (9H, s), 2.23–2.37 (4H, m), 2.83 (1H, br), 3.04–3.33 (4H, m), 4.13 (2H, q, J=7.1 Hz), 5.00–5.11 (4H, m), 5.64–5.85 (2H, m);
$^{13}$C-NMR(CDCl$_3$, δ): 14.27, 28.41, 32.51, 33.23, 34.46, 44.52, 45.00, 48.03, 49.29, 60.53, 79.67, 116.63, 117.11, 134.78, 135.40, 155.41, 174.43;
MASS (m/z): 212 [M−Boc+1]$^+$ (2) Ethyl N-(tert-butoxycarbonyl)-2-(2-propenyl)-3-(4-pentenylamino)propionate IR (film) 2977, 2933, 1734, 1699, 1648, 1588 cm$^{-1}$;
$^1$H-NMR(CDCl$_3$, δ): 1.25 (3H, t, J=7.1 Hz), 1.45 (9H, s), 1.55–1.66 (2H, m), 1.96–2.07 (2H, m), 2.23–2.41 (2H, m), 2.83–3.33 (5H, m), 4.13 (2H, q, J=7.1 Hz), 4.94–5.11 (4H, m), 5.64–5.90 (2H, m);
MASS (m/z): 226 [M−Boc+1]$^+$.

(3) (−)-1-[N-(tert-butoxycarbonyl)-2(R)-(2-propenyl)-3-(2-propenylamino)propionyl]-4(R)-isopropyl-2-oxazolidinone $[α]_{28}^D$=−84.3° (c=0.6, CHCl$_3$);
IR (film) 2973, 2933, 1783, 1697, 1643, 1463 cm$^{-1}$;
$^1$H-NMR(CDCl$_3$, δ): 0.85 (3H, d, J=7.0 Hz), 0.90 (3H, d, J=7.1 Hz), 1.45 (9H, s), 2.29–2.36 (3H, m), 3.41–3.43 (2H, m), 3.76–4.45 (6H, m), 5.01–5.13 (4H, m), 5.66–5.87 (2H, m);
MASS (m/z): 281 [M−Boc+1]$^+$.

Preparation 12

To a solution of ethyl N-(tert-butoxycarbonyl)-2-(2-propenyl)-3-(2-propenylamino)propionate (0.39 g, 1.31 mmol) in dichloromethane (50 mL) was added benzylidene-bis(tricyclohexylphosphine)dichlororuthenium (100 mg). The mixture was refluxed under nitrogen atmosphere for 2 hours, then evaporated in vacuo. The residue was purified by a silica gel chromatography eluting with a mixture of ethyl acetate and n-hexane(1:10) to give ethyl N-(tert-butoxycarbonyl)-1H-2,5,6,7-tetrahydroazepine-3-carboxylate (0.31 g, 1.18 mmol, 90.1%) as a colourless oil.

IR (film) 2977, 1733, 1699, 1458, 1394 cm$^{-1}$;
$^1$H-NMR(CDCl$_3$, δ): 1.22–1.30 (3H, m), 1.46 (9H, s), 2.45 (2H, br), 2.91 (1H, br), 3.45–3.57 (1H, m), 3.77–4.26 (5H, m), 5.67–5.69 (2H, m);
$^{13}$C-NMR(CDCl$_3$, δ): 14.21, 26.98, 27.55, 28.41, 43.17, 43.83, 47.28, 48;91, 60.63, 79.74, 79.95, 127.24, 128.43, 129.03, 129.40, 155.22, 155.42, 173.75.;
$^{13}$C-NMR (CDCl$_3$, 318K, δ): 14.23, 27.56, 28.48, 43.97, 47.41, 48.37, 60.60, 79.74, 79.87, 127.42, 129.25, 155.32, 173.69;
MASS (m/z): 170 [M−Boc+1]$^+$.

Preparation 13

The following compounds (1) to (3) were obtained in a manner similar to Preparation 12.

(1) Ethyl N-(tert-butoxycarbonyl)-1,2,3,6,7,8-hexahydroazocine-7-carboxylate

IR (film) 2978, 2935, 1733, 1650, 1467, 1415 cm$^{-1}$;
$^1$H-NMR (CDCl$_3$, δ): 1.21–1.30 (3H, m), 1.46 and 1.47 (total 9H, s), 2.28–2.42 (4H, m), 2.95–3.16 (2H, m), 3.28–3.40 (1H, m), 3.75–3.84 (2H, m), 4.07–4.20 (3H, m), 5.63–5.71 (1H, m), 5.79–5.90 (1H, m);
$^{13}$C-NMR (CDCl$_3$, δ): 5.07, 19.32, 31.09, 31.20, 32.21, 32.51, 33.58, 47.81, 49.29, 53.44, 53.83, 54.69, 55.59, 65.42, 65.54, 84.64, 84.82, 132.98, 133.67, 135.57, 136.14, 160.23, 160.53, 178.64, 178.85;
MASS (m/z): 184 [M−Boc+1]$^+$.

(2) Ethyl N-(tert-butoxycarbonyl)-1H-2,3,4,7,8,9-hexahydroazonine-8-carboxylate

IR (film) 2975, 2927, 1729, 1697, 1481, 1413 cm$^{-1}$;
$^1$H-NMR (CDCl$_3$, δ): 1.20–1.31 (3H, m), 1.47 (9H, s), 1.50–1.61 (2H, m), 2.04–2.89 (6H, m), 3.17–3.83 (3H, m), 4.08–4.18 (2H, m), 5.52–5.55 (2H, m);
$^{13}$C-NMR (CDCl$_3$, δ): 14.25, 22.58, 22.81, 25.04, 25.41, 26.51, 28.53, 29.71, 41.75, 42.96, 52.11, 52.88, 53.02, 53.69, 60.34, 126.29, 127.00, 130.99, 131.61;

MASS (m/z): 198 [M−Boc+1]⁺.

(3) (−)-1-[1-(tert-butoxycarbonyl)-1H-2,5,6,7-tetrahydroazepine-6(R)-carbonyl]-4(R)-isopropyl-2-oxazolidinone $[\alpha]_{28}^{D}$=−56.2° (c=0.6, CHCl₃);

IR (film) 2969, 2933, 1779, 1693, 1619, 1459 cm⁻¹;

¹H-NMR (CDCl₃, δ): 0.86–0.93 (6H, m), 1.43 and 1.47 (total 9H, s each), 2.34–2.46 (3H, m), 3.65–4.43 (8H, m), 5.68–5.75 (2H, m);

MASS (m/z): 353 [M−Boc+1]⁺.

Preparation 14

To a solution of ethyl N-(tert-butoxycarbonyl)-2H-1,3,4,7-terahydroazepine -3-carboxylate (0.31 g, 1.18 mmol, 90.1%) in ethyl acetate (5 mL) was added 4N solution of HCl in ethyl acetate (2.5 mL). After the mixture was stirred for 3 hours, the solvent was removed by decantation. The residue was dried in vacuo, then dissolved with dimethylformamide (DMF) (5 mL). To the solution was added 1-(tert-butoxycarbonyl)-piperidine-4-carboxylic acid (270 mg, 1.04 mmol), 1-hydroxybenztriazole (145 mg, 1.07 mmol) and 1-ethyl-3-(3-dimethylaminopropyl)carbodiimide (0.36 mL, 1.97 mmol). The mixture was stirred for 2 hours, quenched by an aqueous saturated NaHCO₃ solution, then extracted with ethyl acetate. The extract was washed with water and brine, dried over Na₂SO₄, and evaporated in vacuo. The residue was purified by a silica gel column chromatography eluting with a mixture of ethyl acetate and n-hexane (1:10) to give ethyl N-{3-[1-(tert-butoxycarbonyl)-4-piperidinyl)propionyl]-1H-2,5,6,7-terahydroazepine-3-carboxylate (0.29 g, 0.71 mmol, 68.3%) as a colourless oil.

¹H-NMR (CDCl₃, δ): 1.07–1.13 (2H, m), 1.22–1.32 (3H, m), 1.45 (9H, s), 1.53–1.70 (6H, m), 2.32–2.49 (4H, m), 2.60–2.72 (2H, m), 2.82–3.06 (1H, m), 3.66–4.20 (7H, m), 5.63–5.83 (2H, m);

MASS (m/z): 309 [M−Boc+1]⁺.

Preparation 15

To a solution of ethyl N-{3-[1-(tert-butoxycarbonyl)4-piperidinyl)propionyl}-2H-1,3,4,7-terahydroazepine-3-carboxylate (272 mg, 0.67 mmol) in methanol (5 mL) was added 1N aqueous LiOH (2.3 mL) solution. After stiring for an hour, the mixture was acidified to pH 2.5 with 20% aqueous KHSO₄ solution, and extracted with ethyl acetate. The extract was dried over Na₂SO₄, and evaporated in vacuo. The residue was dissolved in DMF (5 mL). To the solution was added β-alanine methyl ester hydrochloride (87 mg, 1.04 mmol), 1-hydroxybenztriazole (102 mg, 0.75 mmol) and 1-ethyl-3-(3-dimethylaminopropyl)carbodiimide (0.14 mL, 0.75 mmol). The mixture was stirred for 2 hours, quenched by a saturated aqueous NaHCO₃ solution, then extracted with ethyl acetate. The extract was washed with water and brine, dried over Na₂SO₄, and evaporated in vacuo. The residue was purified by a silica gel column chromatography eluting with a mixture of ethyl acetate and n-hexane (1:10) to give N-{1-[3-[1-(tert-butoxycarbonyl)-4-piperidinyl)propionyl]-1H-2,5,6,7-terahydroazepine-3-carbonyl}-β-alanine methyl ester (0.29 g, 0.71 mmol, 68.3%) as a colourless oil.

¹H-NMR (CDCl₃, δ): 1.00–1.28 (2H, m), 1.45 (9H, s), 1.54–1.70 (3H, m), 2.14–2.39 (4H, m), 2.51–2.83 (4H, m), 3.33–3.56 (2H, m), 3.71–3.82 (1H, m), 4.04–4.23 (3H, m), 5.64–5.72 (1H, m), 5.79–5.87 (1H, m), 7.36 (1H, m);

MASS (m/z): 366 [M−Boc+1]⁺.

Preparation 16

3-Hydroxypropylamine (1.48 mL, 19.4 mmol) was added to a solution of ethyl acrylate (2.0 mL, 18.5 mmol) in ethanol (20 mL). The mixture was stirred overnight at room temperature, then evaporated in vacuo. The residue was dissolved in dichloromethane (20 mL), and DIBOC (5.08 mL, 22.2 mmol) was added at 0° C. The mixture was stirred overnight at room temperature, then evaporated in vacuo. The residue was purified by a silica gel column chromatography eluting with a mixture of ethyl acetate and n-hexane (1:20) to give ethyl N-(tert-butoxycarbonyl)-3-(3-hydroxypropylamino)propionate (3.6 g, 13.1 mmol, 70.8%) as a colourless oil.

IR (film) 3451, 2978, 1735, 1693, 1675, 1479, 1417 cm⁻¹;

¹H-NMR (CDCl₃, δ): 1.26 (3H, t, J=7.1 Hz), 1.47 (9H, s), 1.68–1.79 (2H, m), 2.53–2.60 (2H, m), 3.40–3.66 (7H, m), 4.14 (2H, q, J=7.1 Hz);

MASS (m/z): 176 [M−Boc+1]⁺.

Preparation 17

Ethyl N-(tert-butoxycarbonyl)-3-(3-hydroxybutylamino)propionate was obtained in a manner similar to Preparation 16.

IR (film) 3446, 2979, 1735, 1714, 1689, 1652, 1456 cm⁻¹;

¹H-NMR (CDCl₃, δ): 1.26 (3H, t, J=7.1 Hz), 1.46 (9H, s), 1.55–1.57 (4H, m), 2.52–2.60 (2H, m), 3.20–3.24 (2H, m), 3.43–3.50 (2H, m), 3.65–3.71 (2H, m), 4.13 (2H, q, J=7.1 Hz);

MASS (m/z): 190 [M−Boc+1]⁺.

Preparation 18

To a solution of dimethylsulfoxide (DMSO) (1.11 mL, 5.81 mmol) in dichloromethane (DCM)(15 mL) was added dropwise a solution of oxalyl chloride (1.01 mL, 11.62 mmol) in DCM (5 mL) at −78° C. To the mixture was added a solution of ethyl N-(tert-butoxycarbonyl)-3-(3-hydroxypropylamino)propionate (1.6 g, 5.81 mmol) in DCM (10 mL) after 30 minutes. The mixture was stirred for 30 minutes at −78° C., then triethylamine (5.91 mL) was added. After stirring for 30 minutes at room temperature, the mixture was quenched by a saturated aqueous NH₄Cl solution, and extracted with DCM. The organic layer was washed with water and brine, dried over Na₂SO₄, and evaporated in vacuo. The residue was dissolved in THF (20 mL), then a Wittig reagent, which was prepared from methyltriphenylphosphonium bromide (2.49 g, 22.2 mmol) and 1N tert-BuOK THF solution (6.97 mL) in THF (10 mL), was added to the solution at 0° C. The mixture was stirred for an hour at room temperature, then quenched by a saturated aqueous NH₄Cl solution, and extracted with ethyl acetate. The organic layer was washed with water and brine, dried over Na₂SO₄, and evaporated in vacuo. The residue was purified by a silica gel column chromatography eluting with a mixture of ethyl acetate and n-hexane (1:10) to give ethyl N-(tert-butoxycarbonyl)-3-(3-butenylamino)propionate (1.2 g, 0.44 mmol, 76.1%) as a colourless oil.

IR (film) 2978, 1735, 1697, 1475 cm⁻¹;

¹H-NMR (CDCl₃, δ): 1.25 (3H, t, J=7.1 Hz), 1.46 (9H, s), 2.22–2.32 (2H, m), 2.52–2.60 (2H, m), 3.23–3.26 (2H, m), 3.43–3.50 (2H, m), 4.13 (2H, q, J=7.1 Hz), 5.00–5.11 (2H, m), 5.66–5.87 (1H, m);

MASS (m/z): 172 [M−Boc+1]⁺.

Preparation 19

To a solution of ethyl N-(tert-butoxycarbonyl)-1,2,3,6,7,8-hexahydroazocine-7-carboxylate (167 mg, 0.59 mmol) in ethyl acetate (4 mL) was added 4N solution of HCl in ethyl acetate (2 mL). After the mixture was stirred for 3 hours, the solvent was evaporated in vacuo. The residue was dissolved in a mixture of water and ethyl acetate, then the mixture was adjusted to pH 9 with a saturated aqueous K₂CO₃ solution. The organic layer was separated and dried over Na₂SO₄, and evaporated in vacuo to give ethyl 1,2,3,6,7,8-hexahydroazocine-7-carboxylate (81 mg, 0.44 mmol, 74.6%) as a colourless oil.

IR (film) 2935, 1725, 1648 cm$^{-1}$;
$^1$H-NMR (CDCl$_3$, δ): 1.23–1.30 (3H, m), 2.27–2.32 (2H, m), 2.48–3.15 (7H, m), 3.89 (2H, br), 4.09–4.20 (2H, m), 5.68–5.89 (2H, m);
$^{13}$C-NMR (CDCl$_3$, δ): 14.24, 26.32, 28.22, 46.21, 48.13, 49.55, 60.57, 129.04, 130.69, 174.22;
MASS (m/z): 184 [M+1]$^+$.

Preparation 20

A mixture of ethyl 1,2,3,6,7,8-hexahydroazocine-7-carboxylate (65 mg, 0.35 mmol), 1-(tert-butoxycarbonyl)-piperidine-4-carboxylic acid (91 mg, 0.35 mmol), 1-hydroxybenztriazole (HOBT) (48 mg, 0.35 mmol) and 1-ethyl-3-(3-dimethylaminopropyl)carbodimde hydrochloride (WSC.HCl) (68 mg, 0.35 mmol) in DMF was stirred overnight at room temperature. The mixture was quenched by a saturated aqueous NaHCO$_3$ solution, then extracted with ethyl acetate. The extract was washed with water and brine, dried over Na$_2$SO$_4$, and evaporated in vacuo. The residue was dissolved in THF (3 mL), and 1N aqueous LiOH (0.9 mL) was added thereto. After stiring for an hour, the mixture was acidified to pH 2.5 with 20% aqueous KHSO$_4$ solution, and extracted with ethyl acetate. The extract was dried over Na$_2$SO$_4$, and evaporated in vacuo. The residue was dissolved in DMF (5 mL). To the solution was added β-alanine methyl ester hydrochloride (42 mg, 0.30 mmol), HOBT (41 mg, 0.30 mmol) and WSC (55 mL, 0.30 mmol). After stirring for 2 hours, the mixture was quenched by a saturated aqueous NaHCO$_3$ solution, then extracted with ethyl acetate. The extract was washed with water and brine, dried over Na$_2$SO$_4$, and evaporated in vacuo. The residue was purified by a silica gel column chromatography eluting with a mixture of ethyl acetate and n-hexane (1:10) to give N-{1-[3-[1-(tert-butoxycarbonyl)4-piperidinyl)propionyl]-1,2,3,6,7,8-hexahydroazocine-7-carbonyl}-β-alanine methyl ester (127 mg, 0.27 mmol, 68.3%) as a colourless oil.

$^1$H-NMR (CDCl$_3$, δ): 1.15–1.26 (2H, m), 1.45 (9H, s), 1.55–1.82 (6H, m), 2.26–2.67 (10H, m), 2.88–3.04 (3H, m), 3.46–3.52 (2H, m), 3.69 (3H, s), 3.92–4.10 (3H, m), 5.77–5.80 (2H, m), 6.36–6.70 (1H, m);
MASS (m/z): 380 [M−Boc+1]$^+$.

Preparation 21

To a solution of ethyl N-(tert-butoxycarbonyl)-3-(3-hydroxybutylamino)propionate (1.06 g, 3.66 mmol) in dichloromethane (DCM)(15 mL) was added Dess-Martin periodinate (1.17 g, 4.03 mmol). The mixture was stirred for 2 hours, then, a mixture of a saturated aqueous NaHCO$_3$ solution and Na$_2$S$_2$O$_3$ was added. The organic layer was washed with water and brine, dried over Na$_2$SO$_4$, and evaporated in vacuo. The residue was dissolved in THF (10 mL), then a Wittig reagent, which was prepared from methyltriphenylphosphonium bromide (1.57 g, 4.4 nmmol) and 1N-tert-BuOK solution in THF (4.4 mL), in THF (10 mL) was added to the solution at 0° C. The mixture was stirred for an hour at room temperature, then quenched by a saturated aqueous NH$_4$Cl solution, and extracted with ethyl acetate. The organic layer was washed with water and brine, dried over Na$_2$SO$_4$, and evaporated in vacuo. The residue was purified by a silica gel column chromatography eluting with a mixture of ethyl acetate and n-hexane (1:10) to give ethyl N-(tert-butoxycarbonyl)-3-(4-pentenylamino) propionate (487 gm, 1.71 mmol, 46.6%) as a colourless oil.

IR (film) 2978, 2933, 1735, 1699, 1655, 1558, 1541 cm$^{-1}$;
$^1$H-NMR (CDCl$_3$, δ): 1.26 (3H, t, J=7.1 Hz), 1.46 (9H, s), 1.53–1.68 (2H, m), 1.98–2.09 (2H, m), 2.52–2.59 (2H, m), 3.16–3.23 (2H, m), 3.43–3.50 (2H, m), 4.13 (2H, q, J=7.1 Hz), 4.94–5.07 (2H, m), 5.70–5.91 (1H, m);
MASS (m/z): 186 [M−Boc+1]$^+$.

Preparation 22

To a solution of ethyl N-(tert-butoxycarbonyl)-3-(2-propenylamino)propionate (1.0 g, 3.89 mmol) in methanol (10 mL) was added 1N aqueous LiOH solution (5.0 mL). After stirring overnight, the mixture was acidified to pH 2.5 with 20% aqueous KHSO$_4$ solution, and extracted with ethyl acetate. The extract was dried over Na$_2$SO$_4$, and evaporated in vacuo to give N-(tert-butoxycarbonyl)-3-(2-propenylamino)propionic acid (0.8 g, 3.49 mmol, 89.7%) as a colourless oil.

IR (film) 2977, 1735, 1695, 1671, 1477, 1411 cm$^{-1}$;
$^1$H-NMR (CDCl$_3$, δ): 1.45 (9H, s), 2.58–2.65 (2H, m), 3.44–3.51 (2H, m), 3.83–3.86 (2H, m), 5.09–5.17 (2H, m), 5.68–5.89 (1H, m);
MASS (m/z): 130 [M−Boc+1]$^+$.

Preparation 23

To a solution of N-(tert-butoxycarbonyl)-3-(2-propenylamino)propionic acid (878 mg, 3.83 mmol) in THF (20 mL) was added triethylamine (640 mL, 4.59 mmol) and pivaloyl chloride (519 mL, 4.21 mmol) at 0° C. The mixture was cooled to −78° C. after 30 minutes., then a solution of lithium (R)-4-isopropyl-2-oxazolidinone (4.21 mmol) in THF (15 mL) was added dropwise to the mixture via syringe. The mixture was allowed to warm to 0° C. and stirred for 30 minutes, then a saturated aqueous NH$_4$Cl solution and ethyl acetate was added. The organic layer was separated and washed with water and brine, dried over Na$_2$SO$_4$, and evaporated in vacuo. The residue was purified by a silica gel chromatography eluting with a mixture of ethyl acetate and n-hexane (1:10) to give 1-[N-(tert-butoxycarbonyl)-3-(2-propenylamino)propionyl]-(R)-4-isopropyl-2-oxazolidinone (1.11 g, 3.26 mmol, 85.1%) as a colourless oil.

IR (film) 2972, 1783, 1697, 1463 cm$^{-1}$;
$^1$H-NMR (CDCl$_3$, δ): 0.89 (6H, m), 1.45 (9H, s), 1.65 (2H, br), 2.31–2.41 (1H, m), 3.15–3.22 (2H, m), 3.47–3.51 (2H, m), 4.17–4.38 (3H, m), 5.09–5.30 (2H, m), 5.69–5.86 (1H, m);
MASS (m/z): 241 [M−Boc+1]$^+$.

Preparation 24

To a solution of (−)-1-[1-(tert-butoxycarbonyl)-1H-2,5,6,7-tetrahydroazepine-6(R)-carbonyl]-4(R)-isopropyl-2-oxazolidinone (208 mg, 0.59 mmol) in THF (12 mL) and water (4 mL) was added 30% H$_2$O$_2$ (534 mL, 4.7 mmol) and 1 N aqueous LiOH solution(1.18 mL) at 0° C. for 30 minutes, then a saturate aqueous Na$_2$S$_2$O$_3$: solution was added. The mixture was acidified to pH 2.5 with 20% aqueous KHSO$_4$ solution, and extracted with ethyl acetate. The extract was dried over Na$_2$SO$_4$, and evaporated in vacuo. The residue was dissolved in DMF (5 mL). To the solution was added 2(S)-(benzyloxycarbonylamino)-β-alanine methyl ester hydrochloride (188 mg, 0.65 mmol), 1-hydroxybenztriazole (88 mg 0.65 mmol) and 1-ethyl-3-(3-dimethylaminopropyl)carbodiimide (118 mL, 0.65 mmol). The mixture was stirred overnight, quenched by a saturated aqueous NaHCO$_3$ solution, then extracted with ethyl acetate. The extract was washed with water and brine, dried over Na$_2$SO$_4$, and evaporated in vacuo. The residue was purified by a silica gel column chromatography eluting with a mixture of ethyl acetate and n-hexane (1:5) to give N-[1-(tert-butoxycarbonyl)-1H-2,5,6,7-tetrahydroazepine-6 (R)-carbonyl]-2(S)-(benzloxycarbonylamino)-β-alanine methyl ester (94 mg, 198 mmol, 33.5%) as a colourless oil.

$^1$H-NMR (CDCl$_3$, δ): 0.74–0.97 (1H, m), 1.44 (9H, s), 2.34–2.79 (3H, m), 3.39–3.86 (4H, m), 3.74 (3H, s), 4.07–4.49 (2H, m), 5.11 (2H, s), 5.56–6.07 (3H, m), 7.34 (5H, m), 8.17 (1H, br);

MASS (m/z): 376 [M−Boc+1]⁺.

Preparation 25

To a mixture of benzyl 4-hydroxybenzoate (50 g) and potassium carbonate (33.3 g) in N,N-dimethylformamide (500 ml) was added dropwise tert-butyl bromoacetate (32 ml) at ambient temperature, and the mixture was stirred for 9 hours. The reaction mixture was partitioned between a mixture of ethyl acetate and n-hexane and water. The separated organic layer was washed in turn 20% aqueous sodium carbonate solution and brine, dried over magnesium sulfate and evaporated to give tert-butyl (4-benzyloxycarbonyl)phenoxyacetate (72.3 g. 97.4%) as an oil.

$^1$H-NMR (CDCl$_3$, δ): 1.52 (9H, s), 4.56 (2H, s), 5.33 (2H, s), 6.88–6.95(2H, m), 7.30–7.50 (5H,m), 8.00–8.10 (2H, m);

(+)-APCI/MS (m/z): 287 [M−C(CH$_3$)$_3$+H]⁺.

Preparation 26

Benzyl-(3-methyloxycarbonyl)phenoxyacetate was obtained in a similar manner to Preparation 25.

$^1$H-NMR (CDCl$_3$, δ): 3.90 (3H, s), 4.72 (2H, s), 5.24(2H, s), 7.13 (1H, dd, J=8.3, 2.7 Hz), 7.20–7.45 (6H, m), 7.54 (1H, t, J=2.0 Hz), 7.68 (1H, d, J=7.7 Hz);

(+)-APCI/MS (m/z): 301 [M+H]⁺.

Preparation 27

To a solution of tert-butyl (4-benzyloxycarbonyl) phenoxyacetate (74 g) in ethyl acetate (300 ml) was added 4N-hydrogen chloride in ethyl acetate (540 ml) under nitrogen atmosphere at ambient temperature, and then stirred overnight. After evaporation of the solvent, the residual solid was triturated with ethyl acetate. The insoluble solid was filtered, washed with ethyl acetate and dried to give (4-benzyloxycarbonyl)phenoxyacetic asid (46.68 g, 75.5%) as a white solid.

$^1$H-NMR (CDCl$_3$, δ): 4.74 (2H, s), 5.34 (2H, s), 6.94 (2H, d, J=8.9 Hz), 7.30–7.45 (5H, m), 8.05 (2H, d, J=8.9 Hz);

(+)-APCI/MS (m/z): 287 [M+H]⁺.

Preparation 28

A Mixture of N-isopropyl-(4-benzyloxycarbonyl) phenoxyacetamide (1.5 g) and 10% Pd on carbon (50% wet) in methanol (15 ml) was stirred vigorously under hydrogen atmosphere (1 atm) at room temperature. After 2 hours, the insoluble material was removed off by filtration and the filtrate was concentrated in vacuo. The residue was purified by a silica gel column chromatography eluting with a mixture of methanol and CHCl$_3$ (5:1) to give N-isopropyl-(4-carboxy)phenoxyacetamide (1.03 g, 94.6%) as a white powder.

$^1$H-NMR (DMSO-d$_6$, δ): 1.09 (6H, d, J=6.6 Hz), 3.80–4.05 (1H, m), 4.52 (2H, m), 7.02 (2H, d, J=8.8 Hz), 7.89 (2H, d, J=8.8 Hz), 7.94 (1H, d, J=10.6 Hz);

(+)-APCI/MS (m/z): 238 [M+H]⁺.

Preparation 29

The following compounds (1) to (14) were obtained in a manner similar to Preparation 28.

(1) N-n-butyl-(4-carboxy)phenoxyacetamide.

$^1$H-NMR (DMSO-d$_6$, δ): 0.86 (3H, t, J=7.1 Hz), 1.10–1.55 (4H, m), 3.12 (2H, q, J=6.5 Hz), 4.54 (2H, s), 7.02 (2H, d, J=8.7 Hz), 7.89 (2H, d, J=8.7 Hz), 8.11 (1H, br);

(+)-APCI/MS (m/z): 252 [M+H]⁺.

(2) N,N-Dimethyl-(4-carboxy)phenoxyacetamide $^1$H-NMR (DMSO-d$_6$, δ): 2.84 (3H, s), 2.99 (3H, s), 4.91 (2H, s), 6.98 (2H, d, J=8.8 Hz), 7.91 (2H, d, J=8.8 Hz);

(+)-APCI/MS (m/z): 224 [M+H]⁺.

(3) N-Isobutyl-(4-carboxy)phenoxyacetamide $^1$H-NMR (DMSO-d$_6$, δ): 0.82 (6H, d, J=6.7 Hz), 1.55–1.85 (1H, m), 2.95 (2H, t, J=6.4 Hz), 4.58 (2H, s), 7.03 (2H, d, J=8.8 Hz), 7.89 (2H, d, J=8.8 Hz), 8.12 (1H, br);

(+)-APCI/MS M/Z: 252 [M+H]+

(4) N,N-Diisopropyl-(4-carboxy)phenoxyacetamide $^1$H-NMR (DMSO-d$_6$, δ): 1.23 (6H, d, J=6.6 Hz), 1.41 (6H, d, J=6.7 Hz), 3.30–3.60 (1H, m), 3.90–4.25 (1H, m), 4.71 (2H, s), 7.00 (2H, d, J=8.8 Hz), 8.05 (2H, d, J=8.8 Hz);

(+)-APCI/MS (m/z): 280 [M+H]⁺.

(5) 4-Isoamyloxybenzoic acid $^1$H-NMR (CDCl$_3$, δ): 0.98(6H, d, J=6.4 Hz), 1.65–1.95 (3H, m), 4.06(2H, t, J=6.5 Hz), 6.93(2H, d, J=8.8 Hz), 8.06(2H, d, J=8.7 Hz);

(+)-APCI/MS (m/z): 209 [M+H]⁺.

(6) 4-Cyclopropylmethoxybenzoic acid $^1$H-NMR (CDCl$_3$, δ): 0.37(2H, q, J=5.3 Hz), 0.64(2H, q, J=6.3 Hz), 1.15–1.45(1H, m), 3.87(2H, d, J=6.9 Hz), 6.94 (2H, d, J=8.8 Hz), 8.06(2H, d, J=8.8 Hz);

(+)-APCI/MS (m/z): 193 [M+H]⁺.

(7) 4-Cyclopentoxybenzoic acid $^1$H-NMR (CDCl$_3$, δ): 1.45–2.10(8H, m), 4.75–4.90(1H, m), 6.90(2H, d, J=8.9 Hz), 8.04(2H, d, J=8.8 Hz);

(+)-APCI/MS (m/z): 207 [M+H]⁺.

(8) 4-isopropoxybenzoic acid $^1$H-NMR (CDCl$_3$, δ): 1.37(6H, d, J=6.1 Hz), 4.50–4.75 (1H, m), 6.91(2H, d, J=8.8 Hz), 8.05(2H, d, J=8.7 Hz);

(+)-APCI/MS (m/z): 181 [M+H]⁺.

(9) 4-isohexyloxybenzoic acid $^1$H-NMR (CDCl$_3$, δ): 0.93(6H, d, J=6.5 Hz), 1.35(2H, q, J=7.8 Hz), 1.50–1.70(1H, m), 1.70–1.95(2H, m), 4.01(2H, t, J=6.6 Hz), 6.93(2H, d, J=8.9 Hz), 8.06(2H, d, J=8.8 Hz);

(+)-APCI/MS (m/z): 223 [M+H]⁺.

(10) 4-Neopentyloxybenzoic acid $^1$H-NMR (CDCl$_3$, δ): 1.05 (9H, s), 3.66 (2H, s), 6.94 (2H, d, J=8.9 Hz), 8.06 (2H, d, J=8.8 Hz);

(+)-APCI/MS (m/z): 209 [M+H]⁺.

(11) 3-(Methyloxycarbonyl)phenoxyacetic acid $^1$H-NMR (DMSO-d$_6$, δ): 3.37 (1H, br), 3.85 (3H, s), 4.76 (2H, s), 7.22 (1H, dd, J=7.6, 2.2 Hz), 7.41 (1H, s), 7.47 (1H, d, J=8.0 Hz), 7.57 (1H, d, J=7.7 Hz);

(+)-APCI/MS (m/z): 211 [MH]⁺.

(12) Ethyl-5-(3,4-dimethoxyphenyl)-3-(R)-amino-pentanoate $^1$H-NMR (CDCl$_3$, δ): 1.26 (3H, t, J=7.1 Hz), 2.20–2.80 (4H, m), 3.86 (3H, s), 3.87 (3H, s), 4.15 (2H, q, J=7.1 Hz), 6.65–6.85 (3H, m);

(+)-APCI/MS (m/z): 282 [M+H]⁺.

(13) Ethyl-5-(3,4-dimethoxyphenyl)-3-(S)-amino-pentanoate $^1$H-NMR (CDCl$_3$, δ): 1.26 (3H, t, J=7.1 Hz), 2.20–2.80 (4H, m), 3.10–3.30 (1H, m), 3.86 (3H, s), 3.87 (3H, s), 4.15 (2H, q, J=7.1 Hz), 6.65–6.85 (3H, m);

(+)-APCI/MS (m/z): 282 [M+H]⁺.

(14) Ethyl-3-(4-hydroxyphenyl)-3-(S)-amino-propionate $^1$H-NMR (CDCl$_3$, δ): 1.23(3H, t, J=7.1 Hz), 2.66(2H, d, J=8.0 Hz), 4.14(2H, q, J=7.3 Hz), 4.36(1H, dd, J=7.7, 6.0 Hz), 6.73(2H, d, J=8.6 Hz), 7.18(2H, d, J=8.5 Hz);

(+)-APCI/MS (m/z): 210 [M+H]⁺.

Preparation 30

A mixture of N-isopropyl-(4-carboxy)phenoxyacetamide (0.95 g), 1-hydroxybenzotriazole(0.56 g) and 1-(3-dimethylaminopropyl)-3-ethylcarbodiimide hydrochloride (0.80 g) in N,N-dimethylformamide(10 mL) was stirred at room temperature for 18 hours. The reaction mixture was partitioned between a mixture of ethyl acetate and n-hexane and water. The separated organic layer was washed with water and brine, dried over magnesium sulfate and evaporate to give N-isopropyl-{4-(1-benzotriazoloxy) carbonyl}phenoxyacetamide (1.34 g, 94.4%).

¹H-NMR (DMSO-d₆, δ): 1.11 (6H, d, J=6.5 Hz), 3.80–4.15 (1H, m), 4.67 (2H, s), 7.25 (2H, d, J=8.9 Hz), 7.35–7.80 (4H, m), 8.27 (2H, d, J=8.9 Hz);

(+)–APCI/MS (m/z): 355 [M+H]⁺.

Preparation 31

The following compounds (1) to (17) were obtained in a manner similar to Preparation 30.

(1) N-n-Butyl-{4-(1-benzotriazoloxy)carbonyl}phenoxyacetamide

¹H-NMR (DMSO-d₆, δ): 0.86 (3H, t, J=7.1 Hz), 1.10-1.55 (4H, m), 3.05–3.25 (2H, m), 4.69 (2H, s), 7.25 (2H, d, J=8.9 Hz), 7.30–7.80 (4H, m), 8.11 (1H, br), 8.27 (2H, d, J=8.9 Hz);

(+)–APCI/MS (m/z): 369 [M+H]⁺.

(2) N,N-Dimethyl-{4-(1-benzotriazoloxy)carbonyl}phenoxyacetamide

¹H-NMR (DMSO-d₆, δ): 2.87 (3H, s), 3.02 (3H, m), 5.08 (2H, s), 7.21 (2H, d, J=8.9 Hz), 7.30–7.80 (4H, m), 8.23 (2H, d, J=8.9 Hz);

(+)–APCI/MS (m/z): 341 [M+H]⁺.

(3) N-Isobutyl-{4-(1-benzotriazoloxy)carbonyl}phenoxyacetamide

¹H-NMR DMSO-d₆, δ): 0.85 (6H, d, J=6.6 Hz), 1.55–1.85 (1H, m), 2.98 (2H, t, J=6:2 Hz), 4.72 (2H, s), 7.25 (2H, d, J=8.9 Hz), 7.25–7.75 (4H, m), 8.27 (2H, d, J=8.9 Hz);

(+)–APCI/MS (m/z): 369 [M+H]⁺.

(4) N,N-Diisopropyl-{4-(1-benzotriazoloxy)carbonyl}phenoxyacetamide

¹H-NMR (CDCl₃, δ): 1.26 (6H, d, J=6.5 Hz), 1.43 (6H, d, J=6.7 Hz), 3.35–3.60 (1H, m), 3.90–4.20 (1H, m), 4.78 (2H, s), 7.13 (2H, d, J=9.0 Hz), 7.35–7.65 (3H, m), 8.10 (1H, d, J=8.1 Hz), 8.23 (2H, d, J=8.9 Hz);

(+)–APCI/MS (m/z): 397 [M+H]⁺.

(5) N-Isobutyl-{3-(1-benzotriazoloxy)carbonyl}phenoxyacetaride

¹H-NMR (CDCl₃, δ): 0.94 (6H, d, J=6.7 Hz), 1.70–2.00 (1H, m), 3.21 (2H, t, J=6.5 Hz), 4.61 (2H, s), 6.60 (1H, br), 7.35 (1H, d, J=7.8 Hz), 7.40–7.68 (4H, m), 7.82 (1H, s), 7.98 (1H, d, J=7.8 Hz), 8.12 (1H, d, J=9.1 Hz);

(+)–APCI/MS (m/z): 369 [M+H]⁺.

(6) N-{4-(1-Benzotriazoloxy)carbonyl}phenyl-isocapramide

¹H-NMR (DMSO-d₆, δ): 0.90 (6H, d, J=6.1 Hz), 1.40–1.70 (3H, m), 2.20–2.50 (2H, m), 7.42 (1H, t, J=7.1 Hz), 7.51 (1H, t, J=9.3 Hz), 7.63–7.80 (2H, m), 7.80–8.10 (3H, m), 8.25 (1H, d, J=8.8 Hz), 10.19 (1H, s);

(+)–APCI/MS (m/z): 353 [M+H]⁺

(7) N-{3-(1-Benzotriazoloxy)carbonyl}phenyl-isocapramide

¹H-NMR (DMSO-d₆, δ): 0.90 (6H, d, J=6.1 Hz), 1.40–1.70 (3H, m), 2.33 (2H, t, J=7.4 Hz), 7.30–7.50 (2H, m), 7.50–7.65 (2H, m), 7.73 (1H, d, J=8.3 Hz), 7.83 (1H, d, J=8.1 Hz), 7.99 (2H, d, J=8.3 Hz), 8.23 (1H, s), 10.07 (1H, s);

(+)–APCI/MS (m/z): 353 [M+H]⁺.

(8) N-{4-(1-Benzotriazoloxy)carbonyl}phenyl-isovaleramide

¹H-NMR (DMSO-d₆, δ): 0.97 (6H, d, J=6.3 Hz), 2.00–2.25 (1H, m), 2.25 (2H, d, J=6.9 Hz), 7.30–7.80 (4H, m), 7.80–8.05 (2H, m), 8.25 (2H, d, J=8.8 Hz), 10.47 (1H, s);

(+)–APCI/MS (m/z): 339 [M+H]⁺.

(9) N-{3-(1-Benzotriazoloxy)carbonyl}phenyl-isovalerarmide

¹H-NMR (DMSO-d₆, δ): 0.94 (6H, d, J=6.4 Hz), 2.00–2.35 (3H, m), 7.25–8.30 (8H, m), 10.04 (1H, s);

(+)–APCI/MS (m/z): 339 [M+H]⁺.

(10) N-Isopropyl-(4-benzyloxycarbonyl)phenoxyacetamide

¹H-NMR (CDCl₃, δ): 1.20 (6H, d, J=6.6 Hz), 4.05–4.30 (1H, m), 4.50 (2H, m), 5.35 (2H, s), 6.29 (1H, s, br), 6.95 (2H, d, J=9.0 Hz), 7.25–7.50 (5H, m), 8.06 (2H, d, J=9.0 Hz);

(+)–APCI/MS (m/z): 328 [M+H]⁺.

(11) N,N-Dimethyl-(4-benzyloxycarbonyl)phenoxyacetamide

¹H-NMR (CDCl₃, δ): 2.98 (3H, s), 3.08 (3H, s), 4.74 (2H, s), 5.34 (2H, s), 6.97 (2H, d, J=8.9 Hz), 7.30–7.50 (5H, m), 8.03 (2H, d, J=8.8 Hz);

(+)–APCI/MS (m/z): 314 [M+H]⁺.

(12) N-Isobutyl-(4-benzyloxycarbonyl)phenoxyacetamide

¹H-NMR (CDCl₃, δ): 0.91 (6H, d, J=6.7 Hz), 1.70–1.95 (1H, m), 3.18 (2H, t, J=6.5 Hz), 4.55 (2H, s), 5.34 (2H, s), 6.54 (1H, br), 6.95 (2H, d, J=8.9 Hz) 7.30–7.55 (5H, m), 8.06 (2H, d, J=8.8 Hz);

(+)–APCI/MS (m/z): 342 [M+H]⁺.

(13) N,N-Diisopropyl-(4-benzyloxycarbonyl)phenoxyacetamide

¹H-NMR (CDCl₃, δ): 1.21 (6H, d, J=6.5 Hz), 1.40 (6H, d, J=6.7 Hz), 3.30–3.60 (1H, m), 3.90–4.20 (1H, m), 4.67 (2H, s), 5.33 (2H, s), 6.98 (2H, d, J=6.9 Hz), 7.25–7.50 (5H, m), 8.03 (2H, d, J=6.9 Hz);

(+)–APCI/MS (m/z): 370 [M+H]⁺.

(14) N-Isobutyl-(3-methoxycarbonyl)phenoxyacetamide

¹H-NMR (CDCl₃, δ): 0.92 (6H, d, J=6.7 Hz), 1.70–1.95 (1H, m), 3.19 (2H, t, J=6.5 Hz), 3.93 (3H, s), 4.55 (2H, s), 6.61 (1H, br), 7.13 (1H, dd, J=8.2, 2.6 Hz), 7.40 (1H, t, J=8.0 Hz), 7.60 (1H, t, J=1.9 Hz), 7.72 (1H, d, J=7.7 Hz);

(+)–APCI/MS (m/z): 266 [M+H]⁺.

(15) Ethyl-(4-isocaprylcarbonylamino)benzoate

¹H-NMR (CDCl₃, δ): 0.95 (6H, d, J=6.4 Hz), 1.38 (3H, t, J=7.1 Hz), 1.55–1.73 (3H, m), 2.39 (2H, t, J=4.1 Hz), 4.36 (2H, q, J=7.1 Hz), 7.48 (1H, br), 7.60 (2H, d, J=8.8 Hz), 8.00 (2H, d, J=8.8 Hz);

(+)–APCI/MS (m/z): 264 [M+H]⁺.

(16) Ethyl-(3-isocaprylcarbonylamino)benzoate

¹H-NMR (CDCl₃, δ): 0.93 (6H, d, J=6.3 Hz), 1.39 (3H, t, J=7.1 Hz), 1.52–1.75 (3H, m), 2.38 (2H, m), 4.37 (2H, q, J=7.1 Hz), 7.32–7.52 (2H, m), 7.78 (1H, dt, J=7.8, 1.2 Hz), 7.85–8.05 (2H, d, J=7.7 Hz);

(+)–APCI/MS (m/z): 264 [M+H]⁺.

(17) N-isopropyl-(4-benzyloxycarbonyl)phenoxyacetamide

¹H-NMR (CDCl₃, δ): 0.92 (3H, t, J=7.2 Hz), 1.32 (2H, m), 1.52 (2H, m), 3.35 (2H, q, J=6.6 Hz), 4.53 (2H, s), 5.34 (2H, s), 6.50 (1H, br), 6.95 (2H d, J=9.0 Hz), 7.25–7.55 (5H, m), 8.06 (2H, d, J=9.0 Hz);

(+)–APCI/MS (m/z): 342 [M+H]⁺.

Preparation 32

To a solution of bebzyl-4-hydroxybenzoate(1.50 g), 3-methyl-1-butanol (0.86 ml) and triphenylphosphine(3.45 g) in THF(55 ml) was added dropwise a solution of diethylazodicarboxylate(2.07 ml) in THF (20 ml) at 0° C., then the mixture was stirred for an hour at ambient temperature. The reaction mixture was partitioned between a mixture of ethyl acetate and 20% aqueous sodium carbonate solution. The separated organic layer was washed with brine, dried over magnesium sulfate and concentrated in vacuo. The residue was purified by a silica gel column chromatography eluting with a mixture of ethyl acetate and n-hexane (1:4) to give benzyl-4-isoamyloxybenzoate (1.57 g, 80.1%).

¹H-NMR (CDCl₃, δ): 0.96(6H, d, J=6.4 Hz), 1.65–1.95 (3H, m), 4.03(2H, t, J=6.6 Hz), 5.33(2H, s), 6.90(2H, d, J=8.9 Hz), 7.30–7.55(5H, m), 8.02(2H, d, J=8.9 Hz);

(+)-APCI/MS (m/z): 299 [M+H]⁺.

Preparation 33

The following compounds (1) to (4) were obtained in a manner similar to Preparation 32.

(1) Benzyl 4-cyclopropylmethoxybenzoate
$^1$H-NMR (CDCl$_3$, δ): 0.36 (2H, q, J=5.3 Hz), 0.66 (2H, q, J=6.4 Hz), 1.15–1.45 (1H, m), 3.85 (2H, d, J=6.9 Hz), 5.33 (2H, s), 6.90 (2H, d, J=8.9 Hz), 7.30–7.50 (5H, m), 8.12 (2H, d, J=8.8 Hz);
(+)-APCI/MS (m/z): 283 [M+H]⁺.

(2) Benzyl 4-cyclopentoxybenzoate
$^1$H-NMR (CDCl$_3$, δ): 1.50–2.20 (8H, m), 4.70–4.90 (1H, m), 5.33 (2H, s), 6.87 (2H, d, J=8.9 Hz), 7.25–7.55 (5H, m), 8.00 (2H, d, J=8.8 Hz);
(+)-APCI/MS (m/z): 297 [M+H]⁺.

(3) Benyl 4-isopropoxybenzoate
$^1$H-NMR (CDCl$_3$, δ): 1.35 (6H, d, J=6.1 Hz), 4.50–4.75 (1H, m), 5.33 (2H, s), 6.88 (2H, d, J=8.9 Hz), 7.25–7.50 (5H, m), 8.01 (2H, d, J=8.8 Hz);
(+)-APCI/MS (m/z): 271 [M+H]⁺.

(4) Ethyl 3-(4-isobutyloxyphenyl)-3-(S)-tert-butyloxycarbonylamino-propionate
$^1$H-NMR (CDCl$_3$, δ): 1.18 (3H, t, J=7.1 Hz), 1.42 (9H, s), 1.57 (6H, d, J=5.4 Hz), 2.75–5.90 (2H, m), 3.69 (2H, d, J=6.5 Hz), 3.95–4.65 (4H ,m), 6.84 (2H, d, J=8.7 Hz), 7.24 (2H, d, J=8.7 Hz);
(+)-APCI/MS (m/z): 368 [M+H]⁺.

Preparation 34

To a mixture of KOH (0.74 g) in DMSO(15 ml) were added benzyl 4-hydroxybenzoate(1.5 g) and 1-bromo-4-methylpentane(2.78 ml), then the mixture was refluxed for an hour. Then the reaction mixture was partitioned between a mixture of ethyl acetate and water. The separated organic layer was washed in turn water, 20% aqueous sodium carbonate solution and brine, dried over magnesium sulfate and concentrated in vacuo. The residue was purified by a silica gel column chromatography eluting with a mixture of ethyl acetate and n-hexane (1:30) to give benzyl-4-isohexyloxybenzoate(1.18 g, 57.5%).

$^1$H-NMR (CDCl$_3$, δ): 0.92 (6H, d, J=6.6 Hz), 1.33 (2H, q, J=7.9 Hz), 1.50–1.70 (1H, m), 1.70–1.90 (2H, m), 3.98 (2H, t, J=6.6 Hz), 5.33 (2H, s), 6.90 (2H, d, J=8.8 Hz), 7.30–7.50 (5H, m), 8.021 (2H, d, J=8.8 Hz);
(+)-APCI/MS (m/z): 313 [M+H]⁺.

Preparation 35

Benzyl-4-neopentyloxybenzoate was obtained in a manner similar to Preparation 34.

$^1$H-NMR (CDCl$_3$, δ): 1.04 (9H, s), 3.63 (2H, s), 5.33 (2H, s), 6.90 (2H, d, J=8.8 Hz), 7.30–7.50 (5H, m), 8.02 (2H, d, J=8.8 Hz);
(+)-APCI/MS (m/z): 299 [M+H]⁺.

Preparation 36

To a solution of N-isobutyl-(3-methoxycarbonyl) phenoxyacetamide (0.3 g) in methanol (5 ml) was added 1N-aqueous NaOH solution (3 ml), then the mixture was stirred for 1.5 hours at room temperature. After acidified with 1N-hydrochloric acid, the reaction mixture was partitioned between ethyl acetate and water. The separated organic layer was washed with brine, dried over magnesium sulfate and evaporated to give 3-(N-isobutylaminocarbonylmethoxy)benzoic acid(0.26 g, 91.5%).

$^1$H-NMR (CDCl$_3$, δ): 0.93 (6H, d, J=6.7 Hz), 1.72–1.95 (1H, m), 3.21 (2H, t, J=6.5 Hz), 4.61 (2H, s), 6.68 (1H, br), 7.19 (1H, dd, J=7.9, 2.3 Hz), 7.44 (1H, t, J=8.0 Hz), 7.68 (1H, t, J=2.5 Hz), 7.80 (1H, d, J=7.7 Hz);
(+)-APCI/MS (m/z): 252 [M+H]⁺.

Preparation 37

The following compounds (1) to (4) were obtained in a manner similar to Preparation 36.

(1) 4-(Isocaprylcarbonylanmino)benzoic acid
$^1$H-NMR (DMSO-d$_6$, δ): 0.90 (6H, d, J=6.1 Hz), 1.40–1.70 (3H, m), 2.35 (2H, t, J=7.4 Hz), 7.70 (2H, d, J=8.7 Hz), 7.88 (2H, d, J=8.7 Hz), 10.18 (1H, s), 12.67 (1H, br);
(+)-APCI/MS (m/z): 236 [M+H]⁺.

(2) 3-(Isocaprylcarbonylamino)benzoic acid
$^1$H-NMR (DMSO-d$_6$, δ): 0.90 (6H, d, J=6.1 Hz), 1.40–1.75 (3H, m), 2.32 (2H, t, J=7.4 Hz), 7.41 (1H, t, J=7.9 Hz), 7.60 (1H, d, J=7.8 Hz), 7.82 (1H, J=8.1 Hz), 8.23 (1H, s), 10.06 (1H, s), 12.93 (1H, br);
(+)-APCI/MS (m/z): 236 [M+H]⁺.

(3) 4-(Isovalerylcarbonylamino)benzoic acid
$^1$H-NMR (DMSO-d$_6$, δ): 0.94 (6H, d, J=6.4 Hz), 1.95–2.20 (1H, m), 2.23 (2H, d, J=6.6 Hz), 7.71 (2H, d, J=8.7 Hz), 7.88 (2H, d, J=8.7 Hz), 10.16 (1H, s), 12.68 (1H, br);
(+)-APCI/MS (m/z) 222 [M+H]⁺.

(4) 3-(Isovalerylcarboniminio)benzoic acid
1H-NMR (DMSO-d$_6$, δ): 0.94 (6H, d, J=6.4 Hz), 1.95–2.20 (1H, m), 2.20 (2H, d, J=6.3 Hz), 7.41 (1H, t, J=7.9 Hz), 7.60 (1H, d, J=7.7 Hz), 7.82 (1H, d, J=8.1 Hz), 8.24 (1H, s), 10.03 (1H, s), 12.93 (1H, br);
(+)-APCI/MS (m/z): 222 [M+H]⁺.

Preparation 38

To a solution of ethyl 4-aminobenzoate hydrochloride (2.00 g) in dichloromethane (20 ml) was added pyridine (1.76 ml), and cooled to 0° C. To the mixture was added dropwise isovaleryl chloride(1.33 ml) at 0° C., then the mixture was stirred for 3 hours at 0° C. The reaction mixture was partitioned between a mixture of dichloromethane and water. The separated organic layer was washed in turn with 1N-hydrochloric acid, water, a saturated aqueous NaHCO$_3$ solution and brine, then dried over magnesium sulfate and concentrated in vacuo. The residue was purified by a silica gel column chromatography eluting with a mixture of ethyl acetate and n-hexane (1:4) to give ethyl-(4-isovalerylcarbonylamino)benzoate (2.47 g, 99.9%).

$^1$H-NMR (CDCl$_3$, δ): 1.02 (6H, d, J–6.4 Hz), 1.39 (3H, t, J=7.1 Hz), 2.10–2.40 (3H, m), 4.36 (2H, q, J=7.1 Hz), 7.43 (1H, br), 7.61 (2H, d, J=8.7 Hz), 8.00 (2H, d, J=8.7 Hz);
(+)-APCI/MS (m/z): 250 [M+H]⁺.

Preparation 39

Ethyl (3-isovalerylcarbonylamino)benzoate was obtained in a manner similar to Preparation 38.

$^1$H-NMR (CDCl$_3$, δ): 1.01 (6H, d, J=6.4 Hz), 1.38 (3H, t, J=7.1 Hz), 2.10–2.35 (3H, m), 4.36 (2H, q, J=7.1 Hz), 7.38 (1H, t, J=7.9 Hz), 7.66 (1H, br), 7.96 (1H, d, J=8.1 Hz), 8.15 (1H, d J=8.1 Hz), 8.02 (1H, s);
(+)-APCI/MS (m/z): 250 [M+H]⁺.

Preparation 40

To a solution of oxalyl chloride(0.67 ml) in dichloromethane (80 ml) was added dropwise a solution of DMSO (1.18 ml) in dichloromethane(5 ml) at −78° C. To the mixture was added a solution of 1-(3,4-dimethoxyphenyl) propanol (1.50 g) in dichloromethane(25 ml) after 15 minutes. The mixture was stirred for an hour at −78° C. and for another hour at −45° C., then triethylamine(3.52 ml) was added. After stirring 20 minutes at 0° C., the mixture was quenched by a saturated aqueous NH$_4$Cl solution, and extracted with dichloromethane. The organic layer was dried over MgSO$_4$ and evaporated in vacuo. The residue was purified by a silica gel column chromatography eluting with a mixture of ethyl acetate and n-hexane (1:7 to 1:1) to give 3,4-dimethoxy-hydrocinnamaldehyde (1.05 g, 70.7%).

$^1$H-NMR (CDCl$_3$, δ): 2.77 (2H, t, J=6.8 Hz), 2.91 (2H, t, J=6.9 Hz), 3.86 (3H, s), 3.87 (3H, s), 6.60–6.90 (3H, m), 9.82 (1H, s);

(+)–APCI/MS (m/z): 195 [M+H]$^+$.

Preparation 41

To a solution of sodium hydride (0.22 g) in THF (16 ml) was added triethylphosphonoacetate(1.25 g) at 0° C., after 10 min stirring, a solution of 3,4-dimethoxy-hydrocinnamaldehyde (0.90 g) in THF (9 ml) was added to the mixture. After stirring for 45 minutes at ambient temperature, the mixture was quenched by a saturated aqueous NH$_4$Cl solution, and extracted with ethyl acetate. The organic layer was washed with water and brine, dried over MgSO$_4$ and evaporated in vacuo. The residue was purified by a silica gel column chromatography eluting with a mixture of ethyl acetate and n-hexane (2:3) to give ethyl-5-(3,4-dimethoxyphenyl)-trans-2-pentenoate(1.10 g, 89.8%).

$^1$H-NMR (CDCl$_3$, δ): 1.28 (3H, t, J=7.1 Hz), 2.40–2.60 (2H, m), 2.65–2.80 (2H, m), 3.86 (3H, s), 3.87 (3H, s), 4.18 (2H, q, J=7.1 Hz), 5.84 (1H, d, J=15.7 Hz), 6.69 (1H, s), 6.70–6.90 (2H, m), 7.00 (1H, dt, J=15.7, 6.7 Hz);

(+)–APCI/MS (m/z): 195 [M+H]$^+$.

Preparation 42

Ethyl-3-(4-benzyloxyphenyl)-trans-2-propenoate was obtained in a manner similar to Preparation 41.

$^1$H-NMR (CDCl$_3$, δ): 1.33 (3H, t, J=7.1 Hz), 4.25 (2H, q, J=7.1 Hz), 5.19 (2H, s), 6.31 (1H, d, J=16.0 Hz), 6.97 (2H, d, J=8.8 Hz), 7.30–7.55 (5H, m), 7.47 (2H, d, J=8.8 Hz), 7.64 (1H, d, J=16.0 Hz);

(+)–APCI/MS (m/z): 283 [M+H]$^+$.

Preparation 43

To a solution of R-(+)-N-benzyl-α-methylbenzylamine (1.63 ml) in THF (6.3 ml) was added dropwise 1.54 M solution of n-BuLi in n-hexane (1.97 ml) at 0° C. After stirring for 30 minutes, the mixture was cooled to −78° C., then to the mixture was added a solution of ethyl-5-(3,4-dimethoxyphenyl)-trans-2-pentenoate (0.40 g) in THF (4.0 ml). After stirring for 90 minutes at −78° C., the mixture was quenched by a saturated aqueous NH$_4$Cl solution, and warmed to the room temperature and extracted with ethyl acetate. The organic layer was washed with brine, dried over MgSO$_4$ and evaporated in vacuo. The residue was purified by a silica gel column chromatography eluting with a mixture of ethyl acetate and n-hexane (1:9 to 1:1) to give ethyl-5-(3,4-dimethoxyphenyl)-3-(R)-N-benzyl-α-methylbenzylamino-pentanoate (0.54 g, 75.0%).

$^1$H-NMR (CDCl$_3$, δ): 1.17 (3H, t, J=7.1 Hz), 1.30–1.50 (5H, m), 2.05–2.10 (2H, m), 2.40–2.65 (1H, m), 2.70–3.00 (1H, m), 3.87 (3H, s), 3.88 (3H, s), 3.98 (2H, q, J=7.1 Hz), 6.60–6.85 (3H, m), 7.10–7.55 (10H, m);

(+)–APCI/MS (m/z): 476 [M+H]$^+$.

Preparation 44

The following compounds (1) and (2) were obtained in a manner similar to Preparation 43.

(1) Ethyl 5-(3,4-dimethoxyphenyl)-3-(S)-N-benzyl-α-methylbenzylamino-pentanoate $^1$H-NMR (CDCl$_3$, δ): 1.17 (3H, t, J=7.1 Hz), 1.30–1.50 (5H, m), 2.05–2.10 (2H, m), 2.40–2.65 (1H, m), 2.80–3.10 (1H, m), 3.85 (3H, s), 3.88 (3H, s), 3.98 (2H, q, J=7.1 Hz), 6.60–6.85 (3H, m), 7.10–7.55 (10H, m);

(+)–APCI/MS (m/z): 476 [M+H]$^+$.

(2) Ethyl 3-(4-benzyloxyphenyl)-3-(R)-N-benzyl-α-methylbenzylamino-propionate $^1$H-NMR (CDCl$_3$, δ): 1.04 (3H, t, J=7.1 Hz), 1.20–1.35 (4H, m), 2.40–2.80 (2H, m), 3.68 (2H, d, J=2.86 Hz), 3.92 (2H, q, J=7.0 Hz), 4.30–4.50 (1H, m), 5.05 (2H, s), 6.94 (2H, d, J=8.9 Hz), 7.10–7.55 (17H, m);

(+)–APCI/MS (m/z): 494 [M+H]$^+$.

Preparation 45

To a solution of ethyl 3-(4-hydroxyphenyl)-3-(S)-amino-propionate (0.25 g) in THF (5 ml) was added dropwise a solution of di-tert-butyl dicarbonate (0.34 g) in THF (7 ml) at 0° C. After stirring for 2 hours at ambient temperature, the mixture was partitioned between a mixture of ethyl acetate and water. The separated organic layer was washed with brine, dried over magnesium sulfate and concentrated in vacuo. The residue was purified by a silica gel column chromatography eluting with a mixture of chloroform and methanol (19:1) to give ethyl 3-(4-hydroxyphenyl)-3-(S)-tert-butyloxycarbonylamino-propionate(0.46 g, 124.5%).

$^1$H-NMR (CDCl$_3$, δ): 1.17 (3H, t, J=7.0 Hz), 1.43 (9H, s), 2.70–2.85 (2H, m), 6.70 (2H, d, J=8.6 Hz), 7.10 (2H, d, J=8.4 Hz);

(+)–APCI/MS (m/z): 310 [M+H]$^+$.

Preparation 46

To a solution of ethyl 3-(4-isobutyloxyphenyl)-3-(S)-tert-butyloxycarbonylamino-propionate (0.42 g) in ethyl acetate (5 ml) was added 4N hydrogen chloride in ethyl acetate (5 ml) at 0° C. After stirring for 2.5 hours at ambient temperature, the mixture was partitioned between a mixture of ethyl acetate and a saturated aqueous NaHCO$_3$ solution. The separated organic layer was washed with water and brine, dried over magnesium sulfate and concentrated in vacuo. The residue was purified by a silica gel column chromatography eluting with chloroform and methanol (19:1 to 4:1) to give ethyl 3-(4-isobutyloxyphenyl)-3-(S)-amino-propionate(100 mg, 33.7%).

$^1$H-NMR (CDCl$_3$, δ): 1.02(6H, d, J=6.7 Hz), 1.24(3H, t, J=7.2 Hz), 1.90–2.20(1H, m), 2.63(2H, d, J=6.8 Hz), 3.70 (2H, d, J=6.5 Hz), 4.14(2H, q, J=7.2 Hz), 4.35–4.45(1H, m), 6.86(2H, d, J=8.7 Hz), 7.26(2H, d, J=8.6 Hz);

(+)–APCI/MS (m/z): 266 [M+H]$^+$.

EXAMPLE 1

To a solution of N-{(R)-1-tert-butoxycarbonyl-3-piperidylcarbonyl}-2(S)-benzyloxycarbonylamino-β-alanine methyl ester (1.0 g) in methanol (20 mL) was added 10% palladium on carbon (50% wet, 200 mg). The mixture was stirred vigorously and hydrogen gas was bubbled for 3 hours. The catalyst was removed by filtration, and the filtrate was evaporated in vacuo. The residue was dissolved in tetrahydrofuran (20 mL) and the solution was cooled to 5° C. with ice bath. To the solution, 1 N-aqueous LiOH solution (7.6 mL) was added dropwise at 5° C., then acetic anhydride (0.448 mL) was added dropwise under stirring. After stirring for additional 25 minutes at 5° C., the mixture was washed with diethyl ether and then the pH of the mixture was adjusted to 2.0 with an aqueous 20% KHSO$_4$ solution. The resultant mixture was extracted with a mixture of ethyl acetate-tetrahydrofuran (1:1). The organic layer was washed with brine, dried over Na$_2$SO$_4$ and evaporated in uacuo. The residue was dissolved in ethyl acetate (13 mL) and the solution was cooled to 5° C. with ice bath. After adding dropwise 4 N—HCl in ethyl acetate (5.4 mL) at 5° C., the mixture was stirred at room temperature for an hour. A resulting white solid was collected by filtration and dried in vacuo. To the solution of the solid dissolved in N,N-dimethylformnamide (6.5 mL) was added methanesulfonic acid(MSA) (2.84 g) at 5° C. under nitrogen atmosphere and the mixture was stirred for 2 hours.

To a mixture of 3-(1-tert-butoxycarbonyl-4-piperidyl) acrylic acid (578 mg) and 1-hydroxybenzotriazole (292 mg) in dichloromethane (6.0 mL) was added dropwise 1-ethyl-3-(3-dimethylaminopropyl)carbodiimide (0.394 mL) at 5° C., and the solution was allowed to warm to ambient temperature with stirring for 2 hours. The mixture was poured into water and extracted with dichloromethane. The organic layer was washed with brine, dried over $Na_2SO_4$ and evaporated in vacuo. A solution of the residue dissolved in N,N-dimethylformamide (6.5 mL) was added dropwise under nitrogen atmosphere at 5° C. and then diisopropylethylamine (0.376 mL) was added to the resulting mixture in the previous paragraph. The reaction mixture was stirred overnight at 5° C. The resultant solution was poured into water and the mixture was washed with diethyl ether. After the pH of the separated aqueous layer was adjusted to 2.0 with 20% aqueous $KHSO_4$ solution, the aqueous layer was saturated with NaCl and then extracted with a mixture of ethyl acetate and tetrahydrofuran (1:1). The organic layer was washed with brine, dried over $Na_2SO_4$ and evaporated in vacuo. The residue was chromatographed on silica gel (Wakogel® C-200, 25 mL) eluting with a mixture of chloroform and methanol (from chloroform only to 10:1) to give an amorphous powder.

To an ice-cooled solution of the obtained amorphous powder in ethyl acetate (16 mL) was added dropwise 4 N—HCl in ethyl acetate (3.95 mL) at 5° C. After the mixture was stirred for 3 hours at ambient temperature, a resultant white solid was collected by filtration and dried in vacuo. The dry solid powder was dissolved in water (5.0 mL), and the solution was neutralized to pH 7.0 with an aqueous saturated $NaHCO_3$ solution. The solution was applied to ODS column (Disogel-120SP®, 70 mL) eluting with 3–6% $CH_3CN$/water. The eluent was concentrated in vacuo and lyophilized to give N-[(R)-1-{3-(4-piperidyl)acryloyl}-3-piperidylcarbonyl]-2(S)-acetylamino-β-alanine (418 mg) as a white powder.

IR (KBr): 3419, 3302, 1655, 1599 $cm^{-1}$;

$^1$H-NMR ($D_2O$, δ): 1.48–2.09 (12H, m), 2.45–2.62 (2H, m), 2.97–3.51 (8H, m), 3.63–3.73 (1H, m), 3.95–4.41 (3H, m), 6.43–6.51 (1H,m), 6.60–6.72 (1H, m);

MASS (m/z): 395 ($M^+$+1).

EXAMPLE 2

To an ice-cooled mixture of (R)-1-{3-(1-tert-butoxycarbonyl-4-piperidyl)acryloyl}-3-piperidinecarboxylic acid (454 mg) and N,N-dimethylformamide (0.096 mL) in dichloromethane (9 mL) was added dropwise oxalyl chloride (0.108 mL) under nitrogen atmosphere, and the solution was stirred for 30 minutes at 5° C.

To a solution of 2(S)-tert-butoxycarbonylamino-β-alanine (252 mg) in N,N-dimethylformamide (5.0 mL) was added MSA (2.45 g) under nitrogen atmosphere at 5° C., and the mixture was stirred for 30 minutes. After adding dropwise the resulting mire in the previous paragraph at 5° C. under stirring, the mixture was allowed to warm to ambient temperature and then stirred for 4 hours. The resultant reaction mixture was poured into water and the pH of the solution was adjusted to 8.5 with an aqueous saturated $NaHCO_3$ solution. The aqueous solution was washed with ethyl acetate and the pH of the aqueous solution was adjusted to 2.0 with 20% aqueous $KHSO_4$ solution. The solution was saturated with NaCl and then, extracted with a mixture of ethyl acetate and tetrahydrofuran (1:1). The separated organic layer was washed with brine, dried over $Na_2SO_4$ and evaporated in vacuo. The residue was chromatographed on silica gel (Wakogel® C-200, 20 mL) eluting with a mixture of chloroform and methanol (from chloroform only to 15:1) to give an amorphous powder.

To an ice-cooled solution of the amorphous powder in ethyl acetate (4.0 mL) was added dropwise 4 N—HCl in ethyl acetate (1.72 m/L) at 5° C. The mixture was allowed to warm to ambient temperature and then stirred for 3 hours. A resultant white solid was collected by filtration and dried in vacuo. The dry powder was dissolved in water (5.0 mL), and the solution was neutralized to pH 7.0 with an aqueous saturated $NaHCO_3$ solution. The solution was applied to ODS column (Disogel-120SP®, 50 mL) eluting with 4–6% $CH_3CN$/water. The eluent was concentrated in vacuo and lyophilized to give N-[(R)-1-{3-(4-piperidyl)acryloyl}-3-piperidyl-carbonyl]-2(S)-amino-β-alanine (116 mg) as a white powder.

IR (KBr): 3425, 3311, 1653, 1597, 1562 $cm^{-1}$;

$^1$H-NMR ($D_2O$, δ): 1.51–1.85 (5H, m), 2.02–2.08 (3H, m), 2.47–2.80 (2H, m), 2.92–3.58 (9H, m), 3.95–4.42 (2H, m), 6.48 (1H, d, J=15.6 Hz), 6.61–6.73 (1H, m);

MASS (m/z): 353 ($M^+$+1).

EXAMPLE 3

To an ice-cooled mixture of (R)-1-{3-(1-benzyloxycarbonyl-4-piperidyl)propionyl}-3-piperidinecarboxylic acid (500 mg) and N,N-dimethylformamide (0.096 mL) in dichloromethane (10 mL) was added dropwise oxalyl chloride (0.108 mL) under nitrogen atmosphere, and the solution was stirred for 30 minutes at 5° C.

To a solution of 2(S)-tert-butoxycarbonylamino-β-alanine (252 mg) in N,N-dimethylformamide (5.0 mL) was added MSA (2.45 g) under nitrogen atmosphere at 5° C., and the mixture was stirred for 30 minutes. To the mixture, the resulting mixture in the previous paragraph was added dropwise at 5° C. under stirring. The mixture was allowed to warm to ambient temperature and stirred for 4 hours. The resultant mixture was poured into water and the pH of the solution was adjusted to 8.5 with an aqueous saturated $NaHCO_3$ solution. The solution was washed with ethyl acetate and then the pH of the solution was adjusted to 2.0 with 20% aqueous $KHSO_4$ solution. The solution was saturated with NaCl and then extracted with a mixture of ethyl acetate and tetrahydrofuran (1:1). The separated organic layer was washed with brine, dried over $Na_2SO_4$ and evaporated in vacuo. The residue was chromatographed on silica gel (Wakogel® C-200, 20 mL) eluting with a mixture of chloroform and methanol (from chloroform only to 15:1) to give an amorphous powder.

To a solution of the amorphous powder in methanol (5.0 mL) was added 10% palladium on carbon (50% wet, 50 mg). The mixture was stirred vigorously and hydrogen gas was bubbled for 2.5 hours. The catalyst was removed by filtration, and the filtrate was evaporated in vacuo. The residue was dissolved in water (5.0 mL) and the solution was applied to ODS column (Disogel-120SP®, 60 mL) eluting with 20% $CH_3CN$/water. The eluent was concentrated in vacuo and lyophilized to give N-[(R)-1-{3-(4-piperidyl) propionyl}-3-piperidylcarbonyl]-2(S)-tert-butoxycarbonylamino-β-alanine (182 mg) as a white powder.

IR (KBr): 3425, 1697, 1647, 1624 $cm^{-1}$;

$^1$H-NMR ($D_2O$,δ): 1.44 (9H, s), 1.32–2.01 (11H, m), 2.47–2.54 (3H, m), 2.80–3.04 (3H, m), 3.15–3.46 (4H, m), 3.60–3.69 (1H, m), 3.82–3.96 (1H, m), 4:07–4.34 (2H, m);

MASS (m/z): 455 ($M^+$+1).

EXAMPLE 4

To a mixture of (R)-1-{3-(1-benzyloxycarbonyl-4-piperidyl)propionyl}-3-piperidinecarboxylic acid (515 mg) and 1-hydroxybenzotriazole (173 mg) in dichloromethane (10 mL) was added 1-ethyl-3-(3-dimethylaminopropyl)carbodiimide (0.233 mL) dropwise at 5° C., and the solution was allowed to warm to ambient temperature with stirring for 2 hours. The reaction mixture was poured into water and the resultant was extracted with dichloromethane. The organic layer was washed with brine, dried over $Na_2SO_4$ and evaporated in vacuo. The residue was dissolved in N,N-dimiethylformamide (10 mL).

To a solution of 2(R)-tert-butoxycarbonylamino-β-alanine (260 mg) in N,N-dimethylformamide (3.0 ml,) was added MSA (1.68 g) under nitrogen atmosphere at 5° C., and the mixture was stirred for an hour. To the mixture, the resulting mixture in the previous paragraph was added dropwise under stirring at 5° C. The mixture was allowed to warm to ambient temperature and stirred for 6 hours. The resultant mixture was poured into water and the pH of the solution was adjusted to 8.0 with 1 N aqueous NaOH solution. The solution was washed with ethyl acetate and then, the pH of the solution was adjusted to 2.0 with 20% aqueous $KHSO_4$ solution. The solution was saturated with NaCl and extracted with a mixture of ethyl acetate and tetrahydrofuran (1:1). The separated organic layer was washed with brine three times, dried over $Na_2SO_4$ and evaporated in vacuo. The residue was chromatographed on silica gel (Wakogel® C-200, 40 mL) eluting with a mixture of chloroform and methanol (from chloroform only to 25:1) to give an amorphous powder.

To a solution of the amorphous powder in methanol (15 mL) was added 10% palladium on carbon (50% wet, 150 mg). The mixture was stirred vigorously and hydrogen gas was bubbled for 5 hours. The catalyst was removed by filtration, and the filtrate was evaporated in vacuo. The residue was dissolved in water (15 mL) and the solution was applied to ODS column (Disogel-120SP®, 170 mL) eluting with 20% $CH_3CN$/water. The eluent was concentrated in uacuo and lyophilized to give N-[(R)-1-{3-(4-piperidyl)propionyl}-3-piperidylcarbonyl]-2(R)-tert-butoxycarbonylamino-β-alanine (248 mg) as a white powder.

IR (KBr): 3410, 3311, 1695, 1622 $cm^{-1}$;

$^1$H-NMR ($D_2O$, δ): 1.44 (9H, s), 1.32–2.02 (11H, m), 2.35–2.56 (3H, m), 2.80–3.69 (8H, m), 3.84–4.39 (3H, m);

MASS (m/z): 455 ($M^+$+1);

Anal. Calcd for $C_{22}H_{38}N_4O_6 \cdot 2H_2O$: C, 53.86; H, 8.63; N, 11.42. Found: C, 54.21; H, 8.86; N, 11.53.

EXAMPLE 5

To a solution of N-[(R)-1-{3-(1-tert-butoxycarbonyl-4-piperidyl)-propionyl}-3-piperidylcarbonyl]-2(S)-benzyloxycarbonylamino-β-alanine methyl ester (9.70 g) in methanol (200 mL) was added 10% palladium on carbon (50% wet, 1.94 g). The mixture was stirred vigorously and hydrogen gas was bubbled for 3 hours. The catalyst was removed by filtration, and the filtrate was evaporated in vacuo.

The residue was dissolved in tetrahydrofuran (100 mL) and cooled to 5° C. with ice bath. After adding dropwise 1 N-aqueous LiOH solution (48.3 mL) at 5° C., the mixture was stirred for 30 minutes. The solution was neutralized to pH 7.0 with 20% aqueous $KHSO_4$ solution and concentrated to about 20 mL. The resultant solution was applied to ODS column (Disogel-120SP®, 150 mL) eluting with 50% $CH_3CN$/water. The eluent was concentrated in vacuo and lyophilized to give N-[(R)-1-{3-(1-tert-butoxycarbonyl-4-piperidyl)propionyl}-3-piperidylcarbonyl]-2-(S)-amino-β-alanine (7.08 g) as a white powder.

$^1$H-NMR ($D_2O$, δ): 1.45 (9H, s), 1.01–1.99 (11H, m), 2.41–2.52 (3H, m), 2.73–3.01 (3H, m), 3.14–3.36 (1H, m), 3.57–4.06 (6H, m), 4.20–4.38 (1H, m);

MASS (m/z): 455 ($M^+$+1).

EXAMPLE 6

N-[(R)-1-{3-(1-tert-Butoxycarbonyl-4-piperidyl)propionyl}-3-piperidylcarbonyl]-2(R)-amino-β-alanine was obtained in a manner similar to Example 5.

$^1$H-NMR ($D_2O$, δ): 0.78–0.89 (2H, m), 1.16 (9H, s), 1.22–1.72 (9H, m), 2.17–2.25 (3H, m), 2.44–2.56 (2H, m), 2.63–2.75 (1H, m), 2.83–3.07 (1H, m), 3.24–3.37 (1H, m), 3.48–3.76 (5H, m), 3.94–4.09 (1H, m);

MASS (m/z): 455 ($M^+$+1).

EXAMPLE 7

To an ice-cooled suspension of N-[(R)-1-{3-(1-tert-butoxycarbonyl-4-piperidyl)propionyl}-3-piperidylcarbonyl]-2(S)-amino-β-alanine (300 mg) in acetone (90 mL) was added 4-formyl-2-methyl-1,3,4-triazolin-5-thione (116 mg). The reaction mixture was allowed to warm to ambient temperature and stirred for 26 hours. The resultant solution was evaporated in vacuo and the residue was dissolved in water. The pH of the solution was adjusted to 8.5 with an aqueous saturated $NaHCO_3$ solution and the solution was washed with diethyl ether. After the pH of the aqueous layer was adjusted to 2.0 with 20% aqueous $KHSO_4$ solution, the solution was saturated with NaCl and extracted with a mixture of ethyl acetate and tetrahydrofuran (1:1) twice. The combined organic layer was washed with brine, dried over $Na_2SO_4$, and evaporated in vacuo. The residue was chromatographed on silica gel (Wakogel® C-200, 80 mL) eluting with a mixture of chloroform and methanol (from chloroform only to 15:1) to give an amorphous powder.

To an ice-cooled solution of the amorphous powder in ethyl acetate (10 mL) was added 4 N—HCl in ethyl acetate (1.65 mL) dropwise at 5° C. After allowing to warm to ambient temperature, the mixture was stirred for 1.5 hours. A resultant white solid was collected by filtration and dried in vacuo. The dry powder was dissolved in water (5.0 mL), and the solution was neutralized to pH 7.0 with an aqueous saturated $NaHCO_3$ solution. The solution was applied to ODS column (Disogel-120SP®, 50 mL) eluting with 3–4% $CH_3CN$/water. The eluent was concentrated in vacuo and lyophilized to give N-[(R)-1-{3-(4-piperidyl)propionyl}-3-piperidyl-carbonyl]-2(S)-formylamino-β-alanine (250 mg) as a white powder.

IR (KBr): 3411, 3313, 1666, 1653, 1630, 1618 $cm^{-1}$;

$^1$H-NMR ($D_2O$, δ): 1.33–1.97 (11H, m), 2.43–2.50 (3H, m), 2.74–3.02 (3H, m), 3.11–3.47 (4H, m), 3.62–3.92 (2H, m), 4.09–4.28 (1H, m), 4.39–4.46 (1H, m), 8.08 (1H, s);

MASS (m/z): 383 ($M^+$+1).

EXAMPLE 8

N-[(R)-1-{3-(4-Piperidyl)propionyl}-3-piperidylcarbonyl]-2(R)-formylamino-β-alanine was obtained in a manner similar to Example 7.

IR (KBr): 3425, 3313, 1666, 1653, 1630, 1618 $cm^{-1}$;

¹H-NMR (D₂O, δ): 1.32–2.01 (11H, m), 2.50–2.55 (3H, m), 2.78–3.02 (3H, m), 3.14–3.53 (4H, m), 3.60–3.98 (2H, m), 4.14–4.35 (1H, m), 4.44–4.52 (1H, m), 8.12 (1H, s);

MASS (m/z): 383 (M⁺+1).

EXAMPLE 9

To an ice-cooled solution of N-[(R)-1-{3-(1-tert-butoxycarbonyl-4-piperidyl)propionyl}-3-piperidylcarbonyl]-2(S)-amino-β-alanine (200 mg) in tetrahydrofuran (4.0 mL) was added dropwise 1 N-aqueous NaOH solution (1.45 mL), and then added dropwise n-hexanoic anhydride (0.254 mL) at 5° C. The solution was allowed to warm to ambient temperature and stirred for an hour. The reaction mixture was washed with diethyl ether and the pH of the solution was adjusted to 2.0 with 20% KHSO₄ aqueous solution. The solution was saturated with NaCl and extracted with a mixture of ethyl acetate and tetrahydrofuran (1:1). The organic layer was washed with brine, dried over Na₂SO₄ and evaporated in vacuo.

To a solution of the residue dissolved in ethyl acetate (10 mL) was added dropwise 4 N—HCl in ethyl acetate (2.2 mL) at 5° C. The solution was allowed to warm to ambient temperature and stirred for 2 hours. The resultant white solid was collected by filtration and dried in vacuo. The dry powder was dissolved in water (5.0 mL), and the solution was neutralized to pH 7.0 with an aqueous saturated NaHCO₃ solution. The solution was applied to ODS column (Disogel-120SP®, 50 mL) eluting with 25% CH₃CN/water. The eluent was concentrated in vacuo and lyophilized to give N-[(R)-1-{3-(4-piperidyl)propionyl}-3-piperidylcarbonyl]-2(S)-n-hexanoylamino-β-alanine (184 mg) as a white powder.

IR (KBr): 3431, 3313, 1649 cm⁻¹;

¹H-NMR (D₂O,δ): 0.83–0.90 (3H, m), 1.30–2.02 (19H, m), 2.25–2.54 (5H, m), 2.80–3.05 (3H, m), 3.14–3.50 (4H, m), 3.61–3.71 (1H, m), 3.83–3.97 (1H, m), 4.16–4.43 (2H, m);

MASS (m/z): 467 (M⁺+1).

EXAMPLE 10

N-[(R)-1-{3-(4-Piperidyl)propionyl}-3-piperidylcarbonyl]-2(R)-n-hexanoylamino-β-alanine was obtained in a manner similar to Example 9.

IR (KBr): 3431, 3313, 1666, 1649, 1631, 1622 cm⁻¹;

¹H-NMR (D₂O,δ): 0.83–0.90 (3H, m), 1.29–2.01 (19H, m), 2.25–2.54 (5H, m), 2.79–3.05 (3H, m), 3.10–3.52 (4H, m), 3.58–3.72 (1H, m), 3.87–4.00 (1H, m), 4.16–4.71 (2H, m);

MASS (m/z): 467 (M⁺+1).

EXAMPLE 11

To a solution of N-[(R)-1-{3-(1-tert-butoxycarbonyl-4-piperidyl)-propionyl}-3-piperidylcarbonyl]-2(S)-amino-β-alanine methyl ester (745 mg) in tetrahydrofuran (15 mL) was added dropwise 1 N-aqueous LiOH solution (5.57 mL) at 5° C. After stirring for an hour, the reaction mixture was added dropwise with p-methoxybenzoyl chloride (544 mg) at 5° C. The solution was allowed to warm to ambient temperature and stirred for 2 hours. The mixture was washed with diethyl ether and then, the pH of the solution was adjusted to 1.5 with 20% aqueous KHSO₄ solution. The solution was saturated with NaCl and extracted with a mixture of ethyl-acetate and tetrahydrofuran (2:1) twice. The combined organic layer was washed withbrine, dried over Na₂SO₄ and evaporated in vacuo.

To a solution of the residue dissolved in ethyl acetate (20 mL) was added dropwise 4 N—HCl in ethyl acetate (3.98 mL) at 5° C. The solution was allowed to warm to ambient temperature and stirred for 1.5 hours. The resultant white solid was collected by filtration and dried in vacuo. The dry powder was dissolved in water (15 mL), and the solution was neutralized to pH 7.0 with an aqueous saturated NaHCO₃ solution. The solution was applied to ODS column (Disogel-120SP®, 150 mL) eluting with 30% CH₃CN/water. The eluent was concentrated in vacuo and lyophilized to give N-[(R)-1-{3-(4-piperidyl)propionyl}-3-piperidylcarbonyl]-2(S)-(p-methoxybenzoyl)amino-β-alanine (731 mg) as a white powder.

IR (KBr): 3415, 3307, 1645, 1639, 1622, 1608, 1502 cm⁻¹;

¹H-NMR (D₂O,δ): 1.26–1.97 (11H, m), 2.20–2.27 (1H, m), 2.38–2.46 (2H, m), 2.68–3.01 (3H, m), 3.14–3.26 (1H, m), 3.36–3.43 (2H, m), 3.62–3.81 (3H, m), 3.90 (3H,s), 4.06–4.19 (1H, m), 4.55–4.66 (1H, m), 7.07–7.14 (2H, m), 7.77–7.82 (2H, m);

MASS (m/z): 489 (M⁺+1).

EXAMPLE 12

To a solution of N-[(R)-1-{3-(1-tertbutoxycarbonyl-4-piperidyl)-propionyl}-3-piperidylcarbonyl]-2(S)-amino-β-alanine methyl ester (371 mg) in tetrahydrofuran (7.5 mL) was added dropwise 1 N-aqueous LiOH solution (8.32 mL) at 5° C. and the mixture was stirred for 20 minutes. To the mixture, nicotinoyl chloride hydrochloride (564 mg) was added portionwise at 5° C. The solution was allowed to warm to ambient temperature and stirred for 3 hours. The mixture was cooled with ice bath and was added dropwise with conc. HCl (1.65 mL). The solution was allowed to warm to ambient temperature and stirred for 2 hours. The resultant mixture was neutralized to pH 7.0 with an aqueous saturated NaHCO₃ solution, and then concentrated to about 5 mL.

The solution was applied to ODS column (Disogel-120SP®, 40 mL) eluting with 8–10% CH₃CN/water. The eluent was concentrated in vacuo and lyophilized to give N-[(R)-1-{3-(4-piperidyl)propionyl}-3-piperidylcarbonyl]-2(S)-nicotinoylamino-β-alanine (234 mg) as a white powder.

IR (KBr): 3294, 1649, 1543 cm⁻¹;

¹H-NMR (D₂O,δ): 1.29–1.98 (11H, m), 2.29–2.49 (3H, m), 2.83–3.04 (3H, m), 3.18–3.45 (3H, m), 3.63–3.85 (3H, m), 4.12–4.19 (1H, m), 4.62–4.72 (1H, m), 7.57–7.65 (1H, m), 8.19–8.26 (1H, m), 8.69–8.74 (1H, m), 8.91–8.92 (1H, m);

MASS (m/z): 460 (M⁺+1).

EXAMPLE 13

To an ice-cooled solution of N-[(R)-1-{3-(1-tert-butoxycarbonyl-4-piperidyl)propionyl}-3-piperidylcarbonyl]-2(S)-amino-β-alanine (500 mg) in tetrahydrofuran (10 mL) was added dropwise 1 N-aqueous NaOH solution (27.5 mL), then added portionwise isonicotinoyl chloride hydrochloride (1.76 g) at 5° C. The solution was allowed to warm to ambient temperature and stirred for 2 hours. The mixture was cooled with ice bath and conc. HCl (6.0 mL) was added dropwise to the solution. The solution was allowed to warm to ambient temperature and stirred for 4 hours. The resultant mixture was neutralized to pH 7.0 with an aqueous saturated NaHCO₃ solution, and concentrated to about 10 mL.

The solution was applied to ODS column (Disogel-120SP®, 50 mL) eluting with 8% $CH_3CN$/water. The eluent was concentrated in vacuo and lyophilized to give N-[(R)-1-{3-(4-piperidyl)propionyl}-3-piperidylcarbonyl]-2(S)-isonicotinoylamino-β-alanine (239 mg) as a white powder.

IR (KBr): 3411, 3276, 1653, 1622, 1550 $cm^{-1}$;

$^1$H-NMR ($D_2O$,δ): 1.29–1.98 (11H, m), 2.30–2.49 (3H, m), 2.82–3.04 (3H, m), 3.19–3.45 (3H, m), 3.60–3.85 (3H, m), 4.12–4.18 (1H, m), 4.59–4.71 (1H, m), 7.70–7.77 (2H, m), 8.71–8.74 (2H, m);

MASS (m/z): 460 ($M^+$+1).

EXAMPLE 14

N-[(R)-1-{3-(4-Piperidyl)propionyl}-3-piperidylcarbonyl]-2(R)-isonicotinoylamino-β-alanine was obtained in a manner similar to Example 13.

IR (KBr): 3411, 3275, 1653, 1620, 1552 $cm^{-1}$;

$^1$H-NMR ($D_2O$,δ): 1.29–1.98 (11H, m), 2.34–2.47 (3H, m), 2.86–3.04 (3H, m), 3.08–3.44 (3H, m), 3.58–3.84 (3H, m), 4.10–4.30 (1H, m), 4.61–4.71 (1H, m), 7.75–7.78 (2H, m), 8.70–8.74 (2H, m);

MASS (m/z): 460 ($M^+$+1).

EXAMPLE 15

To an ice-cooled solution of N-[(R)-1-{3-(1-tert-butoxycarbonyl-4-piperidyl)propionyl}-3-piperidylcarbonyl]-2(R)-amino-β-alanine (430 mg) in tetrahydrofuran (8.6 mL) was added dropwise 1 N-aqueous NaOH solution (18.0 mL), then added portionwise nicotinoyl chloride hydrochloride (1.01 g) at 5° C. After stirring for 4 hours, conc. HCl (3.94 mL) was added dropwise to the solution at 5° C. The solution was allowed to warm to ambient temperature and stirred for 4.5 hours. The resultant mixture was neutralized to pH 7.0 with an aqueous saturated $NaHCO_3$ solution, and concentrated to about 10 mL.

The solution was applied to ODS column (Disogel-120SP®, 50 mL) eluting with 8–10% $CH_3CN$/water. The eluent was concentrated in vacuo and lyophilized to give N-[(R)-1-{3-(4-piperidyl)propionyl}-3-piperidylcarbonyl]-2(R)-nicotinoylamino-β-alanine (381 mg) as a white powder.

IR (KBr): 3425, 3286, 1649, 1622 $cm^{-1}$;

$^1$H-NMR ($D_2O$,δ): 1.29–1.98 (11H, m), 2.36–2.48 (3H, m), 2.75–3.09 (3H, m), 3.14–3.42 (3H, m), 3.54–3.88 (3H, m), 4.10–4.30 (1H, m), 4.62–4.71 (1H, m), 7.57–7.65 (1H, m), 8.21–8.26 (1H, m), 8.72–8.73 (1H, m), 8.92 (1H, s);

MASS (m/z): 460 ($M^+$+1).

EXAMPLE 16

To an ice-cooled solution of N-[(R)-1-{3-(1-tert-butoxycarbonyl-4-piperidyl)propionyl}-3-piperidylcarbonyl]-2(S)-amino-β-alanine (200 mg) in tetrahydrofuran (4.0 mL) was added dropwise 1 N-aqueous NaOH solution (0.968 mL), then added dropwise cyclohexanecarbonyl chloride (0.0648 mL) at 5° C. After stirring for 15 minutes at the same temperature, the pH of the solution was adjusted to 8.5 with an aqueous saturated $NaHCO_3$ solution. The mixture was washed with diethyl ether and then, the pH of the solution was adjusted to 2.0 with 20% aqueous $KHSO_4$ solution. The solution was saturated with NaCl and extracted with a mixture of ethyl acetate and tetrahydrofuran (1:1). The separated organic layer was washed with brine, dried over $Na_2SO_4$ and evaporated in vacuo.

To an ice-cooled solution of the residue in ethyl acetate (4.0 mL) was added dropwise 4 N—HCl in ethyl acetate (1.10 mL). The solution was allowed to warm to ambient temperature and stirred for 1.5 hours. The resultant white solid was collected by filtration and dried in vacuo. The dry powder was dissolved in water (10 mL), and the solution was neutralized to pH 7.0 with an aqueous saturated $NaHCO_3$ solution. The solution was applied to ODS column (Disogel-120SP®, 50 mL) eluting with 20% $CH_3CN$/water. The eluent was concentrated in vacuo and lyophilized to give N-[(R)-1-{3-(4-piperidyl)propionyl}-3-piperidylcarbonyl]-2(S)-cyclohexanecarbonylamino-β-alanine (175 mg) as a white powder.

IR (KBr): 3425, 3298, 1643, 1637, 1633 $cm^{-1}$;

$^1$H-NMR ($D_2O$, δ): 1.28–2.01 (21H, m), 2.23–2.54 (4H, m), 2.80–3.05 (3H, m), 3.15–3.51 (4H, m), 3.60–3.71 (1H, m), 3.84–3.93 (1H, m), 4.15–4.33 (1H, m), 4.35–4.41 (1H, m);

MASS (m/z): 465 ($M^+$+1).

EXAMPLE 17

The following compounds described in (1) to (9) were obtained in a manner similar to Example 16.

(1) N-[(R)-1-{3-(4-Piperidyl)propionyl}-3-piperidylcarbonyl]-2(S)-pivaloylamino-β-alanine IR (KBr): 3411, 1631, 1541 $cm^{-1}$;

$^1$H-NMR ($D_2O$,δ): 1.19 (9H, s), 1.31–2.01 (11H, m), 2.46–2.54 (3H, m), 2.80–3.05 (3H, m), 3.16–3.57 (4H, m), 3.66–3.73 (1H, m), 3.85–3.91 (1H, m), 4.13–4.35 (2H, m);

MASS (m/z): 439 ($M^+$+1).

(2) N-[(R)-1-{3-(4-Piperidyl)propionyl}-3-piperidylcarbonyl]-2(S)-isobutylcarbonylarnino-β-alanine IR (KBr): 3384, 1647, 1604 $cm^{-1}$;

$^1$H-NMR ($D_2O$,δ): 0.92–0.96 (6H, m), 1.38–2.02 (12H, m), 2.15–2.19 (2H, m), 2.46–2.54 (3H, m), 2.80–3.04 (3H, m), 3.14–3.52 (4H, m), 3.60–3.72 (1H, m), 3.84–3.93 (1H, m), 4.15–4.36 (1H, m), 4.38–4.44 (1H, m);

MASS (m/z): 439 ($M^+$+1)

(3) N-[(R)-1-{3-(4-Piperidyl)propionyl}-3-piperidylcarbonyl]-2(S)-(2-furoyl)amino-β-alanine IR (KBr): 3419, 1635, 1626, 1612, 1597 $cm^{-1}$;

$^1$H-NMR ($D_2O$,δ): 1.30–1.99 (11H, m), 2.36–2.50 (3H, m), 2.75–3.08 (3H, m), 3.14–3.82 (6H, m), 4.12–4.18 (1H, m), 4.54–4.81 (1H, m), 6.63–6.67 (1H, m), 7.18–7.20 (1H, m), 7.70–7.72 (1H, m);

MASS (m/z): 449 ($M^+$+1);

Anal. Calcd for $C_{22}H_{38}N_4O_6 \cdot 2.5H_2O$: C, 53.54; H, 7.56; N, 11.35. Found: C, 53.70; H, 7.55; N, 11.33.

(4) N-[(R)-1-{3-(4-Piperidyl)propionyl}-3-piperidylcarbonyl]-2(S)-(5-isoxazolyl)carbonylamino-β-alanine IR (KBr): 3396, 1658, 1612 $cm^{-1}$;

$^1$H-NMR ($D_2O$,δ): 1.37–2.00 (11H, m), 2.40–2.50 (3H, m), 2.76–3.03 (3H, m), 3.15–3.32 (1H, m), 3.40–3.85 (5H, m), 4.12–4.22 (1H, m), 4.56–4.64 (1H, m), 7.06 (1H, d, J=2.0 Hz), 8.59 (1H, dd, J=2.0 Hz, 2.9 Hz);

MASS (m/z): 450 ($M^+$+1);

Anal. Calcd for $C_{21}H_{31}N_5O_6 \cdot 2.5H_2O$: C, 51.00; H, 7.34; N, 14.16. Found: C, 51.21; H, 7.36; N, 14.15.

(5) N-[(R)-1-{3-(4-Piperidyl)propionyl}-3-piperidylcarbonyl]-2(R)-pivaloylamino-β-alanine IR (KBr): 3419, 1631, 1541 $cm^{-1}$;

$^1$H-NMR ($D_2O$,δ): 1.19 (9H, s), 1.32–2.02 (1 1H, m), 2.35–2.56 (3H, m), 2.80–3.71 (8H, m), 3.87–3.95 (1H, m), 4.15–4.37 (2H, m);

MASS (m/z): 439 (M⁺+1).

(6) N-[(R)-1-{3-(4-Piperidyl)propionyl}-3-piperidylcarbonyl]-2(R)-isobutylcarbonylamino-β-alanine IR (KBr): 3450, 3313, 1645, 1631 cm⁻¹;

¹H-NMR (D₂O,δ): 0.92–0.96 (6H, m), 1.37–2.06 (12H, m), 2.15–2.19 (2H, m), 2.47–2.54 (3H, m), 2.80–3.05 (3H, m), 3.12–3.70 (5H, m), 3.85–3.97 (1H, m), 4.14–4.44 (2H, m);

MASS (m/z): 439 (M⁺+1)

(7) N-[(R)-1-{3-(4-Piperidyl)propionyl}-3-piperidylcarbonyl]-2(R)-cyclohexanecarbonylamino-β-alanine IR (KBr): 3425, 3313, 1649, 1633, 1622 cm⁻¹;

¹H-NMR (D₂O,δ): 1.27–2.02 (21H, m), 2.21–2.54 (4H, m), 2.80–3.70 (8H, m), 3.85–3.98 (1H, m), 4.17–4.42 (2H, m);

MASS (m/z): 465 (M⁺+1).

(8) N-[(R)-1-{3-(4-Piperidyl)propionyl}-3-piperidylcarbonyl]-2(R)-(2-furoyl)amino-β-alanine IR (KBr): 3419, 1635, 1624, 1614, 1599 cm⁻¹;

¹H-NMR (D₂O,δ): 1.37–1.98 (11H, m), 2.41–2.49 (3H, m), 2.77–3.89 (9H, m), 4.09–4.31 (1H, m), 4.55–4.63 (1H, m), 6.63–6.67 (1H, m), 7.18–7.20 (1H, m), 7.71–7.72 (1H, m);

MASS (m/z): 449 (M⁺+1);

Anal. Calcd for C₂₂H₃₂N₄O₆.2.5H₂O: C, 53.54; H, 7.56; N, 11.35. Found: C, 53.29; H, 7.57; N, 11.28.

(9) N-[(R)-1-{3-(4-Piperidyl)propionyl}-3-piperidylcarbonyl]-2(R)-(5-isoxazolyl)carbonylamino-β-alanine IR (KBr): 3398, 1658, 1612 cm⁻¹;

¹H-NMR (D₂O,δ): 1.35–1.99 (11H, m), 2.43–2.50 (3H, m), 2.76–3.93 (9H, m), 4.12–4.33 (1H, m), 4.59–4.67 (1H, m), 7.07 (1H, d, J=2.0 Hz), 8.60 (1H, dd, J=2.0 Hz, 2.9 Hz);

MASS (m/z): 450 (M⁺+1);

Anal. Calcd for C₂₁H₃₁N₅O₆.2.5H₂O: C, 51.00; H, 7.34; N, 14.16. Found: C, 51.01; H, 7.36; N, 14.11.

(10) N-[(R)-1-{3-(4-Piperidyl)propionyl}-3-piperidylcarbonyl]-2(S)-amino-β-alanine was obtained in a manner similar to the later half of Example 16.

IR (KBr): 3421, 3278, 1631, 1566 cm⁻¹;

¹H-NMR (D₂O,δ): 1.29–2.02 (11H, m), 2.47–2.55 (3H, m), 2.76–3.05 (3H, m), 3.15–3.60 (6H, m), 3.83–4.02 (1H, m), 4.18–4.36 (1H, m);

MASS (m/z): 355 (M⁺+1).

EXAMPLE 18

To a solution of N-[(R)-1-{3-(1-tert-butoxycarbonyl-4-piperidyl)propionyl}-3-piperidylcarbonyl]-2(R)-benzyloxycarbonylamino-β-alanine methyl ester (700 mg) in methanol (14 mL) was added 10% palladium on carbon (50% wet, 140 mg). The mixture was stirred vigorously and hydrogen gas was bubbled for 1.5 hours. The catalyst was removed by filtration, and the filtrate was evaporated in vacuo. To a solution of the residue in tetrahydrofuran (14 mL) was added dropwise 1 N-aqueous LiOH solution (4.06 mL) at 5° C. After stirring for 30 minutes, the mixture was added dropwise with p-methoxybenzoyl chloride (436 mg) at 5° C. The solution was allowed to warm to ambient temperature and stirred for an hour. The mixture was washed with diethyl ether and then, the pH of the solution was adjusted to 2.0 with 20% aqueous KHSO₄ solution. The solution was saturated with NaCl and extracted with a mixture of ethyl acetate and tetrahydrofuran (2:1). The organic layer was washed with brine, dried over Na₂SO₄ and evaporated in vacuo.

To a solution of the residue dissolved in ethyl acetate (14 mL) was added dropwise 4 N—HCl in ethyl acetate (2.90 mL) at 5° C. The solution was allowed to warm to ambient temperature and stirred for 1.5 hours. The resultant white solid was collected by filtration and dried in vacuo. The dry solid was dissolved in water (15 mL), and the solution was neutralized to pH 7.0 with an aqueous saturated NaHCO₃ solution. The solution was applied to ODS column (Disogel-120SP®, 170 mL) eluting with 20% CH₃CN/water. The eluent was concentrated in vacuo and lyophilized to give N-[(R)-1-{3-(4-piperidyl)propionyl}-3-piperidylcarbonyl]-2(R)-(4-methoxybenzoyl)amino-β-alanine (555 mg) as a white powder.

IR (KBr): 3392, 3294, 1647, 1608, 1502 cm⁻¹;

¹H-NMR (D₂O,δ): 1.28–1.97 (11H, m), 2.30–2.44 (3H, m), 2.73–3.47(6H, m), 3.54–3.81 (3H, m), 3.91 (3H, s), 4.08–4.24 (1H, m), 4.59–4.69 (1H, m), 7.08–7.13 (2H, m), 7.77–7.83 (2H, m);

MASS (m/z): 489 (M⁺+1).

EXAMPLE 19

To a stirred solution of N-[(3R)-1-{3-(1-tert-butoxycarbonyl-4-piperidyl)propionyl}-3-piperidylcarbonyl]-2(S)-amino-β-alanine (250 mg) in a mixture of tetrahydrofuran (5 mL) and 1 N-aqueous sodium hydroxide solution (1.16 mL) was added dropwise methyl chloroformate (45 µL) at 4° C. After 15 minutes, the reaction mixture was acidified with 5% aqueous potassium hydrogensulfate solution and extracted with ethyl acetate. The organic layer was washed with brine and dried over sodium sulfate. The organic layer was evaporated and the residue was treated with 4 N-hydrogen chloride in ethyl acetate. The resulting insoluble material was collected by filtration and dried. The dry material was dissolved in water. Thus obtained solution was neutralized with an aqueous saturated sodium hydrogencarbonate solution and lyophilized. The residue was purified by ODS column chromatography (Daisogel-120sp®) eluting with 2, 5 and 8% CH₃CN/H₂O and lyophilized to give N-[(3R)-1-{3-(4-piperidyl)propionyl}-3-piperidylcarbonyl]-2(S)-methoxycarbonylamino-β-alanine (162 mg, 71.4%) as an amorphous powder.

IR (KBr) 3421, 1703, 1610, 1556, 1541 cm⁻¹;

¹H-NMR (D₂O,δ): 1.20–2.05 (11H, m), 2.30–2.60 (3H, m), 2.70–3.50 (7H, m), 3.55–4.00 (2H, m), 3.63 (3H, s), 4.05–4.30 (2H, m);

(+)–APCI/MS (m/z): 413 (M⁺+1);

Anal. Calcd for C₁₉H₃₂N₄O₆.1.7H₂O: C, 51.50; H, 8.05; N, 12.64. Found: C, 51.48; H, 8.30; N, 12.62.

EXAMPLE 20

The following compounds described in (1) to (21) were obtained in a manner similar to Example 19.

(1) N-[(3R)-1-{3-(4-Piperidyl)propionyl}-3-piperidylcarbonyl]-2(R)-methoxycarbonylamino-β-alanine IR (KBr) 3419, 1705, 1610, 1556, 1542 cm⁻¹;

¹H-NMR (D₂O, δ): 1.30–2.10 (11H, m), 2.30–2.60 (3H, m), 2.80–3.10 (3H, m), 3.10–3.50 (4H, m), 3.55–3.75 (1H, m), 3.67 (3H, s), 3.80–4.00 (1H, m), 4.10–4.40 (3H, m);

(+)–APCI/MS (m/z): 413 (M⁺+1);

Anal. Calcd for C₁₉H₃₂N₄O₆.1.7H₂O: C, 51.50; H, 8.05; N, 12.64. Found: C, 51.73; H, 8.48; N, 12.67.

(2) N-[(3R)-1-{3-(4-Piperidyl)propionyl}-3-piperidylcarbonyl]-2(S)-benzyloxycarbonylamino-β-alanine IR (KBr) 3480–3360, 1705, 1614, 1554, 1540 cm$^{-1}$;
$^1$H-NMR (D$_2$O, δ): 1.20–2.10 (11H, m), 2.20–2.55 (3H, m), 2.60–3.50 (7H, m), 3.55–3.90 (2H, m), 4.00–4.30 (2H, m), 5.00–5.30 (2H, m), 7.43 (5H, s);
(+)–APCI/MS (m/z): 489 (M$^+$+1);
Anal. Calcd for C$_{25}$H$_{36}$N$_4$O$_6$·1.5H$_2$O: C, 58.24; H, 7.62; N, 10.87. Found: C, 58.47; H, 8.03; N, 10.86.

(3) N-[(3R)-1-{3-(4-Piperidyl)propionyl}-3-piperidylcarbonyl]-2(R)-benzyloxycarbonylamino-β-alanine IR (KBr) 3481, 1703, 1614, 1556, 1541 cm$^{-1}$;
$^1$H-NMR (D$_2$O, δ): 1.20–2.10 (11H, m), 2.20–2.55 (3H, m), 2.60–3.50 (7H, m), 3.55–3.90 (2H, m), 4.00–4.30 (2H, m), 5.00–5.30 (2H, m), 7.43 (5H, s);
(+)–APCI/MS (m/z): 489 (M$^+$+1);
Anal. Calcd for C$_{25}$H$_{36}$N$_4$O$_6$·1.5H$_2$O: C, 58.24; H, 7.62; N, 10.87. Found: C, 58.25; H, 8.01; N, 10.83.

(4) N-[(3R)-1-{3-(4-Piperidyl)propionyl}-3-piperidylcarbonyl]-2(S)-(N,N-dimethylsulfamoyl)amino-βalanine IR (KBr) 3480–3380, 1616, 1562, 1545 cm$^{-1}$;
$^1$H-NMR (D$_2$O, δ): 1.30–2.10 (11H, m), 2.40–2.65 (3H, m), 2.77 (6H, s), 2.85–3.10 (3H, m), 3.10–3.70 (5H, m), 3.80–4.10 (2H, m), 4.20–4.40 (1H, m);
(+)–APCI/MS (m/z): 462 (M$^+$+1);
Anal. Calcd for C$_{19}$H$_{35}$N$_5$O$_6$S·1.9H$_2$O: C, 46.30; H, 7.89; N, 14.12. Found: C, 46.16; H, 8.17; N, 14.00.

(5) N-[(3R)-1-{3-(4-Piperidyl)propionyl}-3-piperidylcarbonyl]-2(R)-(N,N-dimethylsulfamoyl)amino-β-alanine IR (KBr) 3480–3380, 1618 cm$^{-1}$;
$^1$H-NMR (D$_2$O, δ): 1.30–2.10 (11H, m), 2.30–2.65 (3H, m), 2.70–4.40 (11H, m), 2.77 (6H, s);
(+)–APCI/MS (m/z): 462 (M$^+$+1);
Anal. Calcd for C$_{19}$H$_{35}$N$_5$O$_6$S·1.9H$_2$O: C, 46.30; H, 7.89; N, 14.12. Found: C, 46.06; H, 8.03; N, 13.96.

(6) N-[(3R)-1-{3-(4-Piperidyl)propionyl}-3-piperidylcarbonyl]-2(S)-phenoxycarbonylamino-β-alanine IR (KBr) 3490–3310, 1728, 1612, 1552, 1533 cm$^{-1}$;
$^1$H-NMR (D$_2$O, δ): 1.20–2.10 (11H, m), 2.20–2.60 (3H, m), 2.70–4.00 (9H, m), 4.10–4.50 (2H, m), 7.10–7.55 (5H, m);
(+)–APCI/MS (m/z): 475 (M$^+$+1);
Anal. Calcd for C$_{24}$H$_{34}$N$_4$O$_6$·1.5H$_2$O: C, 57.47; H, 7.43; N, 11.17. Found: C, 57.47; H, 7.72; N, 11.21.

(7) N-[(3R)-1-{3-(4-Piperidyl)propionyl}-3-piperidylcarbonyl]-2(R)-phenoxycarbonylamino-β-alanine IR (KBr) 3490–3310, 1728, 1612, 1554, 1533 cm$^{-1}$;
$^1$H-NMR (D$_2$O, δ): 1.20–2.10 (11H, m), 2.20–2.60 (3H, m), 2.70–4.00 (9H, m), 4.10–4.50 (2H, m), 7.10–7.55 (5H, m);
(+)–APCI/MS (m/z): 475 (M$^+$+1);
Anal. Calcd for C$_{24}$H$_{34}$N$_4$O$_6$·1.5H$_2$O: C, 57.47; H, 7.43; N, 11.17. Found: C, 57.42; H, 7.63; N, 11.10.

(8) N-[(3R)-1-{3-(4-Piperidyl)propionyl}-3-piperidylcarbonyl]-2(S)-allyloxycarbonylamino-β-alanine IR (KBr) 3410, 1707, 1612, 1552, 1533 cm$^{-1}$;
$^1$H-NMR (D$_2$O, δ): 1.20–2.10 (11H, m), 2.30–2.60 (3H, m), 2.75–3.05 (3H, m), 3.10–3.50 (4H, m), 3.60–3.75 (1H, m), 3.80–4.00 (1H, m), 4.05–4.35 (2H, m), 4.45–4.75 (2H, m), 5.20–5.40 (2H, m), 5.85–6.10 (1H, m);
(+)–APCI/MS (m/z): 439 (M$^+$+1);
Anal. Calcd for C$_{21}$H$_{34}$N$_4$O$_6$·1.5H$_2$O: C, 54.18; H, 8.01; N, 12.03. Found: C, 54.50; H, 8.14; N, 12.11.

(9) N-[(3R)-1-{3-(4-Piperidyl)propionyl}-3-piperidylcarbonyl]-2(R)-allyloxycarbonylamino-β-alanine IR (KBr) 3475–3380, 1707, 1614, 1552 cm$^{-1}$;
$^1$H-NMR (D$_2$O, δ): 1.20–2.10 (11H, m), 2.30–2.60 (3H, m), 2.75–3.05 (3H, m), 3.10–3.50 (4H, m), 3.60–3.75 (1H, m), 3.80–4.00 (1H, m), 4.05–4.35 (2H, m), 4.45–4.75 (2H, m), 5.20–5.40 (2H, m), 5.85–6.10 (1H, m);
(+)–APCI/MS (m/z): 439 (M$^+$+1);
Anal. Calcd for C$_{21}$H$_{34}$N$_4$O$_6$·1.5H$_2$O: C, 54.18; H, 8.01; N, 12.03. Found: C, 54.47; H, 8.01; N, 12.12.

(10) N-[(3R)-1-{3-(4-Piperidyl)propionyl}-3-piperidylcarbonyl]-2(S)-(2-methoxyethoxycarbonyl)amino-β-alanine IR (KBr) 3430, 1709, 1612, 1552, 1531 cm$^{-1}$;
$^1$H-NMR (D$_2$O, δ): 1.25–2.10 (11H, m), 2.30–2.60 (3H, m), 2.70–3.10 (3H, m), 3.10–3.50 (4H, m), 3.40 (3H, s), 3.60–3.75 (3H, m), 3.75–4.05 (1H, m), 4.10–4.35 (4H, m);
(+)–APCI/MS (m/z): 457 (M$^+$+1);
Anal. Calcd for C$_{21}$H$_{36}$N$_4$O$_7$·1.2H$_2$O: C, 52.75; H, 8.09; N, 11.72. Found: C, 52.58; H, 8.34; N, 11.61.

(11) N-[(3R)-1-{3-(4-Piperidyl)propionyl}-3-piperidylcarbonyl]-2(R)-(2-methoxyethoxycarbonyl)amino-β-alanine IR (KBr) 3430, 1709, 1612, 1552, 1531 cm$^{-1}$;
$^1$H-NMR (D$_2$O, δ): 1.25–2.10 (11H, m), 2.30–2.60 (3H, m), 2.70–3.10 (3H, m), 3.10–3.50 (4H, m), 3.40 (3H, s), 3.60–3.75 (3H, m), 3.75–4.05 (1H, m), 4.10–4.35 (4H, m);
(+)–APCI/MS (m/z): 457 (M$^+$+1);
Anal. Calcd for C$_{21}$H$_{36}$N$_4$O$_7$·1.2H$_2$O: C, 52.75; H, 8.09; N, 11.72. Found: C, 52.75; H, 8.32; N, 11.67.

(12) N-[(3R)-1-{3-(4-Piperidyl)propionyl}-3-pipendylcarbonyl]-2(S)-isopropyloxycarbonylamino-β-alanine IR (KBr) 3430, 1707, 1695, 1626, 1612, 1552, 1531 cm$^{-1}$;
$^1$H-NMR (D$_2$O, δ): 1.20–2.10 (11H, m), 1.25 (6H, d, J=6.2 Hz), 2.30–2.60 (3H, m), 2.70–3.10 (3H, m), 3.10–3.50 (5H, m), 3.60–3.75 (1H, m), 3.80–4.00 (1H, m), 4.05–4.35 (2H, m);
(+)–APCI/MS (m/z): 441 (M$^+$+1);
Anal. Calcd for C$_{21}$H$_{36}$N$_4$O$_7$·1.3H$_2$O: C, 54.36; H, 8.38; N, 12.07. Found: C, 54.58; H, 8.63; N, 12.03.

(13) N-[(3R)-1-{3-(4-Piperidyl)propionyl}-3-piperidylcarbonyl]-2(R)-isopropyloxycarbonylamino-β-alanine IR (KBr) 3430, 1707, 1695, 1626, 1616, 1552, 1531 cm$^{-1}$;
$^1$H-NMR (D$_2$O, δ): 1.20–2.10 (11H, m), 1.24 (6H, d, J=6.2 Hz), 2.30–2.60 (3H, m), 2.70–3.10 (3H, m), 3.10–3.50 (5H, m), 3.60–3.75 (1H, m), 3.80–4.00 (1H, m), 4.05–4.35 (2H, m);
(+)–APCI/MS (m/z): 441 (M$^+$+1);
Anal. Calcd for C$_{21}$H$_{36}$N$_4$O$_7$·0.9H$_2$O: C, 55.22; H, 8.34; N, 12.27. Found: C, 54.42; H, 8.73; N, 12.29.

(14) N-[(3R)-1-{3-(4-Piperidyl)propionyl}-3-piperidylcarbonyl]-2(S)-propyloxycarbonylamino-β-alanine IR (KBr) 3515–3300, 1707, 1657, 1635, 1626, 1614, 1550, 1531 cm$^{-1}$;
$^1$H-NMR (D$_2$O, δ): 0.92 (3H, t, J=7.4 Hz), 1.25–2.10 (13H, m), 2.30–2.60 (3H, m), 2.80–3.10 (3H, m), 3.15–3.55 (4H, m), 3.60–4.35 (6H, m);
(+)–APCI/MS m/z 441 (M+H)$^+$;
Anal. Calcd for C$_{21}$H$_{36}$N$_4$O$_7$·1.1H$_2$O: C, 54.59; H, 8.36; N, 12.17.
Found: C, 54.71; H, 8.70; N, 12.12.

(15) N-[(3R)-1-{3-(4-Pipeidyl)propionyl}-3-piperidylcarbonyl]-2(R)-propyloxycarbonylamino-β-alanine IR (KBr) 3515–3300, 1707, 1658, 1635, 1626, 1614, 1552, 1531 cm$^{-1}$;

$^1$H-NMR (D$_2$O, δ): 0.92 (3H, t, J=7.4 Hz), 1.25–2.10 (13H, m), 2.30–2.60 (3H, m), 2.80–3.10 (3H, m), 3.15–3.55 (4H, m), 3.60–4.35 (6H, m);

(+)-APCI/MS (m/z): 441 (M$^+$+1);

Anal. Calcd for C$_{21}$H$_{36}$N$_4$O$_7$·1.1H$_2$O: C, 54.59; H, 8.36; N, 12.17; Found: C, 54.79; H, 8.36; N, 12.17.

(16) N-[(3R)-1-{3-(4-Pipendyl)propionyl}-3-piperidylcarbonyl]-2(S)-hexyloxycarbonylamino-β-alanine IR (KBr) 3490–3310, 1709, 1635, 1626, 1614, 1550, 1531 cm$^{-1}$;

$^1$H-NMR (D$_2$O, δ): 0.87 (3H, t, J=6.4 Hz), 1.20–2.05 (19H, m), 2.30–2.55 (3H, m), 2.70–3.00 (3H, m), 3.05–3.45 (4H, m), 3.50–3.70 (1H, m), 3.75–4.30 (5H, m);

(+)-APCI/MS (m/z): 483 (M$^+$+1);

Anal. Calcd for C$_{24}$H$_{42}$N$_4$O$_6$·H$_2$O: C, 57.58; H, 8.86; N, 11.19. Found: C, 55.78; H, 9.18; N, 11.16.

(17) N-[(3R)-1-{3-(4-Piperidyl)propionyl}-3-pipendylcarbonyl]-2(R)-hexyloxycarbonylamino-β-alanine IR (KBr) 3490–3310, 1709, 1635, 1628, 1550, 1531 cm$^{-1}$;

$^1$H-NMR (D$_2$O, δ): 0.87 (3H, t, J=6.4 Hz), 1.20–2.05 (19H, m), 2.30–2.55 (3H, m), 2.70–3.00 (3H, m), 3.05–3.45 (4H, m), 3.50–3.70 (1H, m), 3.75–4.30 (5H, m);

(+)-APCI/MS (m/z): 483 (M$^+$+1);

Anal. Calcd for C$_{24}$H$_{42}$N$_4$O$_6$·1.5H$_2$O: C, 56.56; H, 8.90; N, 10.99. Found: C, 56.67; H, 8.92; N, 10.96.

(18) N-[(3R)-1-{3-(4-Piperidyl)propionyl}-3-piperidylcarbonyl]-2(S)-(2-methylpropyloxycarbonyl)amino-β-alanine IR (KBr) 3555–3300, 1707, 1635, 1626, 1550, 1531 cm$^{-1}$;

$^1$H-NMR (D$_2$O, δ): 0.91 (6H, d, J=6.7 Hz), 1.30–2.10 (12H, m), 2.30–2.60 (3H, m), 2.80–3.05 (3H, m), 3.10–3.50 (4H, m), 3.60–3.75 (3H, m), 3.75–4.00 (3H, m), 4.10–4.35 (2H, m);

(+)-APCI/MS (m/z): 455 (M$^+$+1);

Anal. Calcd for C$_{22}$H$_{38}$N$_4$O$_6$·0.9H$_2$O: C, 56.13; H, 8.52; N, 11.90. Found: C, 56.26; H, 8.91; N, 11.93.

(19) N-[(3R)-1-{3-(4-Piperidyl)propionyl}-3-piperidylcarbonyl]-2(R)-(2-methylpropyloxycarbonyl)amino-β-alanine IR (KBr) 3555–3300, 1709, 1635, 1626, 1550, 1531 cm$^{-1}$;

$^1$H-NMR (D$_2$O, δ): 0.91 (6H, d, J=6.7 Hz), 1.30–2.10 (12H, m), 2.30–2.60 (3H, m), 2.80–3.05 (3H, m), 3.10–3.50 (4H, m), 3.60–3.75 (3H, m), 3.75–4.00 (3H, m), 4.10–4.35 (2H, m);

(+)-APCI/MS (m/z): 455 (M$^+$+1);

Anal. Calcd for C$_{22}$H$_{38}$N$_4$O$_6$·1.1H$_2$O: C, 55.70; H, 8.54; N, 11.81. Found: C, 55.64; H, 8.83; N, 11.78.

(20) N-[(3R)-1-{3-(4-Piperidyl)propionyl}-3-piperidylcarbonyl]-2(S)-ethoxycarbonylamino-β-alanine IR (KBr) 3430, 1705, 1626, 1550, 1533 cm$^{-1}$;

$^1$H-NMR (D$_2$O, δ): 1.24 (3H, t, J=7.1 Hz), 1.30–2.10 (11H, m), 2.30–2.60 (3H, m), 2.80–3.10 (3H, m), 3.10–3.50 (4H, m), 3.60–3.75 (1H, m), 3.80–4.00 (1H, m), 4.00–4.40 (4H, m);

(+)-APCI/MS (m/z): 427 (M$^+$+1);

Anal. Calcd for C$_{20}$H$_{34}$N$_4$O$_6$·1.5H$_2$O: C, 52.97; H, 8.22; N, 12.35. Found: C, 52.88; H, 8.33; N, 12.34.

(21) N-[(3R)-1-{3-(4-Piperidyl)propionyl}-3-piperidylcarbonyl]-2(R)ethoxycarbonylamino-β-alanine IR (KBr) 3490–3340, 1707, 1624, 1612, 1550, 1533 cm$^{-1}$;

$^1$H-NMR (D$_2$O, δ): 1.24 (3H, t, J=7.1 Hz), 1.30–2.10 (11H, m), 2.30–2.60 (3H, m), 2.80–3.10 (3H, m), 3.10–3.50 (4H, m), 3.60–3.75 (1H, m), 3.80–4.00 (1H, m), 4.00–4.40 (4H, m);

(+)-APCI/MS (m/z): 427 (M$^+$+1);

Anal. Calcd for C$_{20}$H$_{34}$N$_4$O$_6$·1.3H$_2$O: C, 53.39; H, 8.20; N, 12.45. Found: C, 53.42; H, 8.40; N, 12.49.

EXAMPLE 21

To a stirred solution of 4-methoxyphenylacetic acid (146 mg) and 1-hydroxybenzotriazole (119 mg) in dichloromethane (3 mL) was added 1-ethyl-3-(3-dimethylaminopropyl)carbodiimide (160 μL) under nitrogen atmosphere at ambient temperature. After stirring for 2 hours, the reaction mixture was partitioned between dichloromethane and an aqueous saturated sodium hydrogencarbonate solution. The separated organic layer was washed in turn with water and brine, dried over magnesium sulfate and concentrated to gave a residue.

To a stirred mixture of N-[(3R)-1-{3-(1-tert-butoxycarbonyl-4-piperidyl)propionyl}-3-piperidylcarbonyl]-2(S)-amino-β-alanine (400 mg) and N-trimethylsilylacetamide (1.12 g) in N,N-dimethylformamide (4 mL) was added a solution of the resulting residue in the previous paragraph in a mixture of N,N-dimethylformamide (2 mL) and diisopropylethylamine (153 μL) under nitrogen atmosphere at 5° C., and then the mixture was stirred for 2.5 hours. The reaction mixture was partitioned between diethyl ether and an aqueous sodium hydrogencarbonate solution. The separated aqueous layer was acidified with 20% aqueous potassium hydrogensulfate solution, added saturated sodium chloride in water and extracted with a mixture of tetrahydrofuran and ethyl acetate. The separated organic layer was washed three times with brine and dried over sodium sulfate. The organic layer was evaporated and the residue was purified by a silica-gel column chromatography (Wakogel® C-200) eluting with CHCl$_3$—MeOH 100:1, 50:1, 40:1, 30:1 and 20:1. The obtained product was dissolved in ethyl acetate (5 mL) and the solution was added with 4 N—HCl in ethyl acetate (960 μL) under nitrogen atmosphere at 5° C. The reaction mixture was allowed to warm to ambient temperature and stirred for 5 hours. Resulting insoluble material was collected by filtration, dried and dissolved in water. Thus obtained solution was neutralized with an aqueous saturated sodium hydrogencarbonate solution and lyophilized. The residue was purified by ODS column chromatography (Daisogel-120sp®) eluting with 5, 10, 15 and 20% CH$_3$CN/H$_2$O and lyophilized to give N-[(3R)-1-{3-(4-piperidyl)propionyl}-3-piperidylcarbonyl]-2(S)-(4-methoxyphenylacetyl)amino-β-alanine (140.9 mg, 27.8%) as an amorphous powder.

IR (KBr) 3420, 1635, 1612, 1512 cm$^{-1}$;

$^1$H-NMR (D$_2$O, δ): 1.20–3.20 (19H, m), 3.30–3.90 (7H, m), 3.80 and 3.83 (3H, 2×s (1:1)), 4.00–4.30 (1H, m), 4.35–4.50 (1H, m), 6.99 (2H, d, J=8.6 Hz), 7.31 (2H, d, J=8.6 Hz);

(+)-APCI/MS (m/z): 503 (M$^+$+1);

Anal. Calcd for C$_{26}$H$_{38}$N$_4$O$_6$·1.6H$_2$O: C, 58.76; H, 7.81; N, 10.54. Found: C, 58.66; H, 7.98; N, 10.49.

EXAMPLE 22

The following compounds described in (1) to (5) were obtained in a manner similar to Example 21.

(1) N-[(3R)-1-{3-(4-Piperidyl)propionyl}-3-piperidylcarbonyl]-2(R)-(4-methoxyphenyl)acetylamino-β-alanine IR (KBr) 3420, 1635, 1612, 1512 cm$^{-1}$;

$^1$H-NMR (D$_2$O, δ): 1.20–3.20 (19H, m), 3.30–4.00 (7H, m), 3.82 and 3.83 (3H, 2×s (1:1)), 4.15–4.30 (1H, m), 4.35–4.50 (1H, m), 6.95–7.05 (2H, m), 7.25–7.35 (2H, m);

(+)-APCI/MS (m/z): 503 (M$^+$+1);

Anal. Calcd for C$_{26}$H$_{38}$N$_4$O$_6$·1.6H$_2$O: C, 58.76; H, 7.81; N, 10.54. Found: C, 58.70; H, 8.09; N, 10.53.

(2) N-[(3R)-1-{3-(4-Pipendyl)propionyl}-3-piperidylcarbonyl]-2(S)-((4-carbamoylmethoxy)benzoyl)amino-β-alanine IR (KBr) 3411, 1606, 1549, 1500 cm$^{-1}$;

$^1$H-NMR (D$_2$O, δ): 1.20–2.05 (11H, m), 2.10–2.55 (3H, m), 2.60–3.90 (9H, m), 4.00–4.25 (1H, m), 4.30–4.80 (3H, m), 7.00–7.20 (2H, m), 7.75–7.95 (2H, m).

(3) N-[(3R)-1-{3-(4-Piperidyl)propionyl}-3-piperidylcarbonyl]-2(R)-((4-carbamoylmethoxy)benzoyl)amino-β-alanine IR (KBr) 3415, 1606, 1550, 1502 cm$^{-1}$;

$^1$H-NMR (D$_2$O, δ): 1.15–2.00 (11H, m), 2.25–2.55 (3H, m), 2.65–3.90 (9H, m), 4.05–4.25 (1H, m), 4.55–4.75 (1H, m), 4.57 (2H, s), 7.00–7.15 (2H, m), 7.75–7.95 (2H, m).

(4) N-[(3R)-1-{3-(4-Piperidyl)propionyl}-3-piperidylcarbonyl]-2(S)-((4-N-methylcarbamoylmethoxy)benzoyl)amino-β-alanine IR (KBr) 3415, 1635, 1606, 1549, 1500 cm$^{-1}$;

$^1$H-NMR (D$_2$O, δ): 1.20–2.05 (11H, m), 2.20–2.55 (3H, m), 2.65–3.05 (3H, m), 2.81 (3H, s), 3.05–3.90 (6H, m), 4.05–4.25 (1H, m), 4.55–4.70 (1H, m), 4.70 (2H, s), 7.05–7.15 (2H, m), 7.80 (2H, d, J=8.8 Hz);

(+)-APCI/MS (m/z): 546 (M$^+$+1);

Anal. Calcd for C$_{27}$H$_{39}$N$_5$O$_7$·3H$_2$O: C, 54.26; H, 7.25; N, 11.72. Found: C, 54.53; H, 7.65; N, 11.78.

(5) N-[(3R)-1-{3-(4-Piperidyl)propionyl}-3-piperidylcarbonyl]-2(R)-((4-N-methylcarbamoylmethoxy)benzoyl)amino-β-alanine IR (KBr) 3410, 1637, 1606, 1549, 1500 cm$^{-1}$;

$^1$H-NMR-(D$_2$O, δ): 1.20–2.05 (11H, m), 2.20–2.55 (3H, m), 2.75–3.90 (9H, m), 2.82 (3H, s), 4.05–4.30 (1H, m), 4.55–4.70 (1H, m), 4.70 (2H, s), 7.05–7.15 (2H, m), 7.81 (2H, d, J=8.8 Hz);

(+)-APCI/MS (m/z): 546 (M$^+$+1);

Anal. Calcd for C$_{27}$H$_{39}$N$_5$O$_7$·3H$_2$O: C, 54.26; H, 7.25; N, 11.72. Found: C, 54.09; H, 7.56; N, 11.69.

EXAMPLE 23

To a solution of 2-(4-methoxyphenyl)propionic acid (159 mg) and N,N-dimethylformamide (68.1 μL) in dichloromethane (5 mL) was added oxalyl chrolide (76.8 μL) under nitrogen atmosphere at 5° C. and the mixture was stirred for 30 minutes.

To a stirred mixture of N-[(3R)-1-{3-(1-tert-butoxycarbonyl-4-piperidyl)propionyl}-3-piperidylcarbonyl]-2(S)-amino-β-alanine (400 mg) and N-trimethylsilylacetamide (1.16 g) in N,N-dimethylformamide (8 mL) was added the resulting solution in the previous paragraph and diisopropylethylamine (153 μL) under nitrogen atmosphere at 5° C., and the mixture was then stirred overnight. The reaction mixture was partitioned between diethyl ether and an aqueous sodium hydrogencarbonate solution. The separated aqueous layer was acidified with 20% aqueous potassium hydrogensulfate solution, added with an aqueous saturated sodium chloride solution and extracted with a mixture of tetrahydrofuran and ethyl acetate. The separated organic layer was washed three times with brine and dried over sodium sulfate. The organic layer was evaporated and the residue was purified by a silica-gel column chromatography (Wakogel® C-200) eluting with CHCl$_3$—MeOH 100:1, 50:1, 40:1, 30:1 and 20:1. The obtained product was dissolved in ethyl acetate (4 mL) and the solution was added 4 N—HCl in ethyl acetate (820 μL) under nitrogen atmosphere at 5° C. The reaction mixture was allowed to warm to ambient temperature and stirred for 5 hours. The resulting insoluble material was collected by filtration, dried and dissolved in water. The solution was neutralized with an aqueous saturated sodium hydrogencarbonate solution, purified by ODS column chromatography (Daisogel-120sp®) eluting with 5, 10, 15 and 20% CH$_3$CN/H$_2$O and lyophilized to give N-[(3R)-1-{3-(4-piperidyl)propionyl}-3-piperidylcarbonyl]-2(S)-(2-(4-methoxyphenyl)propionyl)amino-β-alanine (169 mg, 42.4%) as an amorphous powder.

IR (KBr) 3410, 1635, 1612, 1552, 1514 cm$^{-1}$;

$^1$H-NMR (D$_2$O,δ): 1.20–2.10 (11H, m), 2.15–2.65 (5H, m), 2.70–3.65 (10H, m), 3.81 (3H, s), 3.80–3.95 (1H, m), 4.10–4.45 (2H, m), 6.81 (2H, dd, J=8.7, 2.4 Hz), 7.24 (2H, d, J=8.1 Hz);

(+)-APCI/MS (m/z): 517 (M$^+$+1);

Anal. Calcd for C$_{27}$H$_{40}$N$_4$O$_6$·1.2H$_2$O: C, 60.25; H, 7.94; N, 10.41. Found: C, 60.11; H, 8.24; N, 10.36.

EXAMPLE 24

N-[(3R)-1-{3-(4-Piperidyl)propionyl}-3-piperidylcarbonyl]-2(R)-(2-(4-methoxyphenyl)propionyl)amino-β-alanine was obtained in a manner similar to Example 23.

IR (KBr) 3410, 1633, 1612, 1552, 1513 cm$^{-1}$;

$^1$H-NMR (D$_2$O, δ): 1.20–2.10 (11H, m), 2.15–2.70 (5H, m), 2.70–3.60 (10H, m), 3.75–3.90 (1H, m), 3.80 (3H, s), 4.10–4.45 (2H, m), 6.90–7.00 (2H, m), 7.24 (2H, d, J=8.6 Hz);

(+)-APCI/MS (m/z): 517 (M$^+$+1);

Anal. Calcd for C$_{27}$H$_{40}$N$_4$O$_6$·1.2H$_2$O: C, 60.25; H, 7.94; N, 10.41. Found: C, 60.20; H, 8.18; N, 10.37.

EXAMPLE 25

To a mixture of N-[(3R)-1-{3-(1-tert-butoxycarbonyl-4piperidyl)-propionyl}-3-piperidylcarbonyl]-2(S)-amino-β-alanine (200 mg) and N-trimethylsilylacetamide (595 mg) in N,N-dimethylformamide (2 mL) was added in turn with methoxyoxalyl chloride (81 μL) and diisopropylethylamine (76.6 μL) under nitrogen atmosphere at 5° C., and the mixture was stirred overnight. The reaction mixture was partitioned between diethyl ether and an aqueous sodium hydrogencarbonate solution. The separated aqueous layer was acidified with 20% aqueous potassium hydrogensulfate solution, added saturated sodium chloride in water and extracted with a mixture of tetrahydrofuran and ethyl acetate. The separated organic layer was washed three times with brine and dried over sodium sulfate. The organic layer was evaporated and the residue was treated with 4 N—HCl in ethyl acetate. The resulting insoluble material was collected by filtration, dried and dissolved in water. Thus obtained solution was neutralized with an aqueous saturated sodium hydrogencarbonate solution, purified by ODS column chromatography (Daisogel-120sp®) eluting with 2, 4, 6 and 8 and 10% CH$_3$CN/H$_2$O and lyophilized to give N-[(3R)-1-{3-(4-piperidyl)-propionyl}-3-piperidylcarbonyl]-2(S)-methoxyoxalylamino-β-alanine as an amorphous powder (42.6 mg, 21.9%).

IR (KBr) 3430, 1751, 1693, 1612, 1552, 1533 cm$^{-1}$;

$^1$H-NMR (D$_2$O, δ): 1.30–2.10 (11H, m), 2.30–2.60 (3H, m), 2.80–3.10 (3H, m), 3.15–4.00 (6H, m), 3.93 (3H, s), 4.10–4.50 (2H, m);

(+)-APCI/MS (m/z): 441 (M$^+$+1).

EXAMPLE 26

The following compounds described in (1) to (3) were obtained in a manner similar to Example 25.

(1) N-[(3R)-1-{3-(4-Piperidyl)propionyl}-3-piperidylcarbonyl]-2(R)-methoxyoxalylamino-β-alanine
IR (KBr) 3430, 1751, 1693, 1612, 1552, 1533 cm$^{-1}$;
$^1$H-NMR (D$_2$O, δ): 1.30–2.10 (11H, m), 2.30–2.60 (3H, m), 2.80–4.00 (9H, m), 3.93 (3H, s), 4.10–4.50 (2H, m);
(+)-APCI/MS (m/z): 441 (M$^+$+1).

(2) N-[(3R)-1-{3-(4-Piperidyl)propionyl}-3-piperidylcarbonyl]-2(S)-ethoxyoxalylamino-β-alanine
IR (KBr) 3423, 1745, 1691, 1610, 1552 cm$^{-1}$;
$^1$H-NMR (D$_2$O, δ): 1.36 (3H, t, J=7.1 Hz), 1.30–2.10 (11H, m), 2.30–2.60 (3H, m), 2.80–4.00 (9H, m), 4.10–4.50 (2H, m), 4.39 (2H, q, J=7.1 Hz);
(+)-APCI/MS (m/z): 483 (M$^+$+1).

(3) N-[(3R)-1-{3-(4Piperidyl)propionyl}-3-piperidylcarbonyl]-2(R)-ethoxyoxalylamino-β-alanine
IR (KBr) 3423, 1745, 1691, 1612, 1549 cm$^{-1}$;
$^1$H-NMR (D$_2$O, δ): 1.36 (3H, t, J=7.1 Hz), 1.30–2.10 (11H, m), 2.30–2.60 (3H, m), 2.80–4.00 (9H, m), 4.10–4.50 (2H, m), 4.39 (2H, q, J=7.1 Hz);
(+)-APCI/MS (m/z): 483 (M$^+$+1).

EXAMPLE 27

To a solution of N-[(3R)-1-{3-(1-tert-butoxycarbonyl-4-piperidyl)propionyl}-3-piperidylcarbonyl]-2(S)-amino-β-alanine (250 mg) and N-trimethylsilylacetamide (361 mg) in acetonitrile (5 mL) was added benzotriazol-1-yl 2-(benzyloxycarbonylamino)acetate (180 mg) and the mixture was stirred under nitrogen atmosphere for an hour at 4° C. The reaction mixture was partitioned between ethyl acetate and 20% aqueous potassium hydrogensulfate solution. The separated organic layer was washed in turn with water and brine and dried over magnesium sulfate. The organic layer was evaporated and the residue was treated with 4 N—HCl in ethyl acetate. The resulting insoluble material was collected by filtration, dried and dissolved in water. The solution was neutralized with an aqueous saturated sodium hydrogencarbonate solution, purified by ODS column chromatography (Daisogel-120sp®) eluting with 10, 15 and 20% CH$_3$CN/H$_2$O and lyophilized to give N-[(3R)-1-{3-(4-Piperidyl)propionyl}-3-piperidylcarbonyl]-2(R)-((2-benzyloxycarbonylamino)acetyl)amino-β-alanine (253.5 mg, 84.5%) as an amorphous powder.

IR (KBr) 3495–3275, 1664, 1635, 1625, 1604, 1589, 1570 cm$^{-1}$;
$^1$H-NMR (D$_2$O, δ): 1.20–2.10 (11H, m), 2.20–2.55 (3H, m), 2.60–3.30 (4H, m), 3.35–3.55 (3H, m), 3.60–3.95 (2H, m), 3.87 (2H, s), 4.10–4.45 (2H, m), 5.17 (2H, s), 7.44 (5H, s);
(+)-APCI/MS (m/z): 546 (M$^+$+1);
Anal. Calcd for C$_{27}$H$_{39}$N$_5$O$_7$.1.6H$_2$O: C, 56.45; H, 7.40; N, 12.19. Found: C, 56.18; H, 7.60; N, 12.57.

EXAMPLE 28

The following compounds described in (1) to (5) were obtained in a manner similar to Example 27.

(1) N-[(3R)-1-{3-(4-Piperidyi)propionyl}-3-piperidylcarbonyl]-2(R)-((2-benzyloxycarbonylamino)acetyl)amino-β-alanine
IR (KBr) 3469–3300, 1722, 1709, 1658, 1635, 1626, 1606, 1570, 1550, 1531, 1520 cm$^{-1}$;
$^1$H-NMR (D$_2$O, δ): 1.20–2.10 (11H, m), 2.20–2.55 (3H, m), 2.60–3.30 (4H, m), 3.35–3.55 (3H, m), 3.60–3.95 (2H, m), 3.87 (2H, s), 4.10–4.45 (2H, m), 5.17 (2H, s), 7.44 (5H, s);
(+)-APCI/MS (m/z): 546 (M$^+$+1);
Anal. Calcd for C$_{27}$H$_{39}$N$_5$O$_7$.2.2H$_2$O: C, 55.41; H. 7.47; N, 11.97. Found: C, 55.41, H, 7.55; N, 12.30.

(2) N-[(3R)-1-{3-(4-Piperidyl)propionyl}-3-piperidylcarbonyl]-2(S)-((3-benzyloxycarbonylamino)propionyl)amino-β-alanine
IR (KBr) 3470–3300, 1722, 1709, 1658, 1635, 1626, 1606, 1570, 1550, 1531, 1520 cm$^{-1}$;
$^1$H-NMR (D$_2$O, δ): 1.25–2.05 (11H, m), 2.20–2.55 (5H, m), 2.60–3.90 (11H, m), 4.10–4.30 (1H, m), 4.30–4.40 (1H, m), 5.10 (2H, s), 7.41 (5H, s);
(+)-APCI/MS (m/z): 560 (M$^+$+1);
Anal. Calcd for C$_{28}$H$_{41}$N$_5$O$_7$.1.7H$_2$O: C, 56.97; H, 7.58; N, 11.86. Found: C, 56.96; H, 7.70; N, 11.81.

(3) N-[(3R)-1-{3-(4-Piperidyl)propionyl}-3-piperidylcarbonyl]-2(R-((3-benzyloxycarbonylamino)propionyl)amino-β-alanine
IR (KBr) 3300, 1716, 1711, 1658, 1635, 1626, 1612, 1570, 1549, 1531 cm$^{-1}$;
$^1$H-NMR (D$_2$O, δ): 1.25–2.05 (11H, m), 2.20–2.55 (5H, m), 2.60–3.90 (11H, m), 4.10–4.40 (2H, m), 5.11 (2H, s), 7.42 (5H, s);
(+)-APCI/MS (m/z): 560 (M$^+$+1);
Anal. Calcd for C$_{28}$H$_{41}$N$_5$O$_7$.1.6H$_2$O: C, 57.15; H, 7.57; N, 11.90. Found: C, 57.06; H, 7.57; N, 11.90.

(4) N-[(3R)-1-{3-(4-Piperidyl)propionyl}-3-piperidylcarbonyl]-2(S)-((2-amino-2-methyl)propionyl)amino-β-alanine hydrochloride
IR (KBr) 3515–3405, 1665, 1658, 1606, 1550, 1531 cm$^{-1}$;
$^1$H-NMR (D$_2$O, δ): 1.30–2.10 (11H, m), 1.60 (3H, s), 1.65 (3H, s), 2.30–2.60 (3H, m), 2.80–4.40 (11H, m);
(+)-APCI/MS (m/z): 440 (M$^+$+1);
Anal. Calcd for C$_{21}$H$_{38}$ClN$_5$O$_5$.2.8H$_2$O: C, 47.91; H, 8.35; N, 13.30. Found: C, 47.96; H, 8.41; N, 13.35.

(5) N-[(3R)-1-{3-(4-Piperidyl)propionyl}-3-piperidylcarbonyl]-2(R)-((2-amino-2-methyl)propionyl)amino-β-alanine hydrochloride
IR (KBr) 3515–3405, 1664, 1604, 1550, 1531 cm$^{-1}$;
$^1$H-NMR (D$_2$O, δ): 1.30–2.10 (17H, m), 2.30–2.60 (3H, m), 2.75–4.45 (11H, m);
(+)-APCI/MS (m/z): 440 (M$^+$+1);
Anal. Calcd for C$_{21}$H$_{38}$ClN$_5$O$_5$.2.5H$_2$O: C, 48.41; H, 8.32; N, 13.44. Found: C, 48.33; H, 8.59; N, 13.44.

EXAMPLE 29

To a solution of N-[(3R)-1-{3-(1-tert-butoxycarbonyl-4-piperidyl)propionyl}-3-piperidylcarbonyl]-(2S)-amino-β-alanine (2 g) and N-trimethylsilylacetamide (2.88 g) in acetonitrile (50 mL) was added benzotriazol-1-yl 2-(benzyloxycarbonylamino)acetate (1.44 g) and the mixture was stirred under nitrogen atmosphere for 3 hours at 4° C. The reaction mixture was partitioned between ethyl acetate and 20% aqueous potassium hydrogensulfate solution. The separated organic layer was washed in turn with water and brine, dried over magnesium sulfate and evaporated. The residue was dissolved in methanol (50 mL) andthe solution was added with 10% palladium on carbon (50% wet, 450 mg) and hydrogenated at atmospheric pressure of hydrogen. The catalyst was removed by filtration and the filtrate was evaporated. The residue was purified by ODS column chromatography (Daisogel-120sp®) eluting with 20 and 50% CH$_3$CN/H$_2$O and lyophilized to give N-[(3R)-1-

{3-(1-tert-butoxycarbonyl-4-piperdyl)propionyl}-3-piperidylcarbonyl]-(2S)-(2-aminoacetyl)amino-β-alanine (1.98 g, 88%) as an amorphous powder.

IR (KBr) 3460–3270, 1689, 1664, 1635, 1626, 1606 cm$^{-1}$;

$^1$H-NMR (D$_2$O, δ): 0.95–2.10 (11H, m), 1.44 (9H, s), 2.30–2.60 (3H, m), 2.65–2.95 (3H, m), 3.05–3.55 (2H, m), 3.60–4.45 (8H, m);

(+)–APCI/MS (m/z): 512 (M$^+$+1);

Anal. Calcd for C$_{24}$H$_{41}$N$_5$O$_7$·H$_2$O: C, 54.43; H, 8.18; N, 13.22. Found: C, 54.52; H, 8.39; N, 12.97.

EXAMPLE 30

The following compounds described in (1) to (3) were obtained in a manner similar to Example 29.

(1) N-[(3R)-1-{3-(1-tert-Butoxycarbonyl-4-piperidyl)propionyl}-3-piperidylcarbonyl]-(2R)-(2-aminoacetyl)amino-β-alanine IR (KBr) 3490–3270, 1689, 1664, 1635, 1626, 1616 cm$^{-1}$;

$^1$H-NMR (D$_2$O, δ): 0.95–2.10 (11H, m), 1.44 (9H, s), 2.30–2.60 (3H, m), 2.65–2.95 (3H, m), 3.05–3.55 (2H, m), 3.65–4.45 (8H, m);

(+)–APCI/MS (m/z): 512 (M$^+$+1);

Anal. Calcd for C$_{24}$H$_{41}$N$_5$O$_7$·H$_2$O: C, 54.43; H, 8.18; N, 13.22. Found: C, 54.43; H, 8.44; N, 12.96.

(2) N-[(3R)-1-{3-(1-tert-Butoxycarbonyl-4-piperidyl)propionyl}-3-piperidylcarbonyl]-(2S)-(3-aminopropionyl)amino-β-alanine IR (KBr) 3300, 1691, 1647, 1570, 1552 cm$^{-1}$;

$^1$H-NMR (D$_2$O, δ): 1.00–2.10 (11H, m), 1.45 (9H, s), 2.30–3.00 (8H, m), 3.10–4.10 (8H, m), 4.10–4.45 (2H, m);

(+)–APCI/MS (m/z): 526 (M$^+$+1);

Anal. Calcd for C$_{25}$H$_{43}$N$_5$O$_7$·1.3H$_2$O: C, 54.69; H, 8.37; N, 12.75. Found: C, 54.74; H, 8.37; N, 12.69.

(3) N-[(3R)-1-{3-(1-tert-Butoxycarbonyl-4-piperidyl)propionyl}-3-piperidylcarbonyl]-(2R)-(3-aminopropionyl)amino-β-alanine IR (KBr) 3298, 1689, 1647, 1570, 1552 cm$^{-1}$;

$^1$H-NMR (D$_2$O, δ): 1.00–2.10 (11H, m), 1.45 (9H, s), 2.30–2.95 (8H, m), 3.10–4.45 (10H, m);

(+)–APCI/MS (m/z): 526 (M$^+$+1);

Anal. Calcd for C$_{25}$H$_{43}$N$_5$O$_7$·1.3H$_2$O: C, 54.69; H, 8.37; N, 12.75. Found: C, 55.00; H, 8.67; N, 12.75.

EXAMPLE 31

To a solution of N-[(3R)-1-{3-(1-tert-butoxycarbonyl-4-piperidyl)propionyl}-3-piperidylcarbonyl]-(2S)-(2-aminoacetyl)amino-β-alanine (280 mg) in ethyl acetate (10 mL) was added 4 N—HCl in ethyl acetate (1.4 mL) and the solution was stirred under nitrogen atmosphere for 3 hours at ambient temperature. The resulting insoluble material was removed by filtration, dried and dissolved in water. The solution was neutralized with an aqueous saturated sodium hydrogencarbonate solution, purified by ODS column chromatography (Daisogel-120sp®) eluting with H$_2$O, 5 and 10% CH$_3$CN/H$_2$O and lyophilized to give N-[(3R)-1-{3-(4-piperidyl)propionyl}-3-piperidylcarbonyl]-(2S)-(2-aminoacetyl)amino-β-alanine (220 mg, 97.8%) as an amorphous powder.

IR (KBr) 3430, 1658, 1635, 1624, 1606, 1570, 1552, 1533 cm$^{-1}$;

$^1$H-NMR (D$_2$O, δ): 1.30–2.10 ((11H, m), 2.30–2.60 (3H, m), 2.70–4.00 (11H, m), 4.10–4.50 (2H, m);

(+)–APCI/MS (m/z): 412 (M$^+$+1);

Anal. Calcd for C$_{19}$H$_{33}$N$_5$O$_5$·3.2H$_2$O: C, 48.64; H, 8.46; N, 14.93. Found: C, 48.66; H, 8.16; N, 14.84.

EXAMPLE 32

The following compounds described in (1) to (3) were obtained in a manner similar to Example 31.

(1) N-[(3R)-1-{3-(4-Piperidyl)propionyl)-3-piperidylcarbonyl]-(2R)-(2-aminoacetyl)amino-β-alanine IR (KBr) 3515–3300, 1664, 1658, 1635, 1626, 1604, 1570, 1552 cm$^{-1}$;

$^1$H-NMR (D$_2$O, δ): 1.30–2.10 (11H, m), 2.30–2.60 (3H, m), 2.70–4.00 (11H, m), 4.10–4.50 (2H, m);

(+)–APCI/MS (m/z): 412 (M$^+$+1);

Anal. Calcd for C$_{19}$H$_{33}$N$_5$O$_5$·3.2H$_2$O: C, 48.64; H, 8.46; N, 14.93. Found: C, 48.46; H, 8.19; N, 14.73.

(2) N-[(3R)-1-{3-(4-Piperidyl)propionyl}-3-piperidylcarbonyl]-(2S)-(3-aminopropionyl)amino-β-alanine IR (KBr) 3515–3300, 1664, 1658, 1635, 1626, 1604, 1589, 1570, 1552 cm$^{-1}$;

$^1$H-NMR (D$_2$O, δ): 1.25–2.10 (11H, m), 2.35–2.75 (5H, m), 2.80–3.10 (3H, m), 3.10–3.55 (6H, m), 3.60–4.00 (2H, m), 4.10–4.45 (2H, m);

(+)–APCI/MS (m/z): 426 (M$^+$+1);

Anal. Calcd for C$_{20}$H$_{35}$N$_5$O$_5$·3.8H$_2$O: C, 48.63; H, 8.69; N, 14.18. Found: C, 48.50; H, 8.30; N, 13.98.

(3) N-[(3R)-1-{3-(4-Piperidyl)propionyl}-3-piperidylcarbonyl]-(2R)-(3-aminopropionyl)amino-β-alanine IR (KBr) 3515–3300, 1658, 1635, 1626, 1604, 1570, 1552 cm$^{-1}$;

$^1$H-NMR (D$_2$O, δ): 1.25–2.10 (11H, m), 2.35–2.75 (5H, m), 2.80–3.10 (3H, m), 3.10–3.55 (6H, m), 3.60–4.00 (2H, m), 4.10–4.45 (2H, m);

(+)–APCI/MS (m/z): 426 (M$^+$+1);

Anal. Calcd for C$_{20}$H$_{35}$N$_5$O$_5$3.8H$_2$O: C, 48.63; H, 8.69; N, 14.18. Found: C, 48.43; H, 8.35; N, 13.96.

EXAMPLE 33

To a stirred solution of N-[(3R)-1-{3-(1-tert-butoxycarbonyl-4-piperidyl)propionyl}-3-piperidylcarbonyl]-2(S)-(2-aminoacetyl)amino-β-alanine (280 mg) in a mixture of tetrahydrofuran (5 mL) and 1 N-aqueous sodium hydroxide solution (1.9 mL) was added acetic anhydride (114 μL) at 4° C. After stirring for 2 hours, the reaction mixture was acidified with 5% aqueous potassium hydrogensulfate solution and extracted with ethyl acetate. The organic layer was washed with brine and dried over magnesium sulfate. The organic layer was evaporated and the residue was treated with 4 N—HCl in ethyl acetate. The resulting insoluble material was collected by filtration, dried and dissolved in water. The solution was neutralized with an aqueous saturated sodium hydrogencarbonate solution, purified by ODS column chromatography (Daisogel-120sp®) eluting with 2, 5 and 8% CH$_3$CN/H$_2$O and lyophilized to give N-[(3R)-1-{3-(4-piperidyl)propionyl}-3-piperidylcarbonyl]-2(S)-((2-acetylamino)acetyl)amino-β-alanine (143.6 mg, 57.9%) as an amorphous powder.

IR (KBr) 3515–3275, 1664, 1635, 1626, 1604, 1589, 1570 cm$^{-1}$;

$^1$H-NMR (D$_2$O, δ): 1.30–2.10 (11H, m), 2.09 (3H, s), 2.35–2.60 (3H, m), 2.75–3.05 (3H, m), 3.10–3.55 (4H, m), 3.65–3.75 (1H, m), 3.80–4.00 (1H, m), 3.93 (2H, s), 4.15–4.45 (2H, m);

(+)-APCI/MS (m/z): 454 (M$^+$+1);

Anal. Calcd for $C_{21}H_{35}N_5O_6 \cdot 2.3H_2O$: C, 50.96; H, 8.06; N, 14.15. Found: C, 51.00; H, 8.28; N, 14.08.

EXAMPLE 34

The following compounds described in (1) to (3) were obtained in a manner similar to Example 33.

(1) N-[(3R)-1-{3-(4-Piperidyl)propionyl}-3-piperidylcarbonyl]-2(R)-((2-acetylamino)acetyl)amino-β-alanine IR (KBr) 3515–3275, 1664, 1635, 1626, 1604, 1570 cm$^{-1}$;

$^1$H-NMR (D$_2$O, δ): 1.30–2.10 (11H, m), 2.09 (3H, s), 2.30–2.60 (3H, m), 2.75–3.05 (3H, m), 3.10–3.55 (4H, m), 3.60–3.75 (1H, m), 3.80–4.05 (1H, m), 3.93 (2H, s), 4.15–4.45 (2H, m);

(+)-APCI/MS (m/z): 454 (M$^+$+1);

Anal. Calcd for $C_{21}H_{35}N_5O_6 \cdot 2.3H_2O$: C, 50.96; H, 8.06; N, 14.15. Found: C, 51.21; H, 8.33; N, 14.16.

(2) N-[(3R)-1-{3-(4-Piperidyl)propionyl}-3-piperidylcarbonyl]-2(S)-((3-acetylamino)propionyl)amino-β-alanine IR (KBr) 3500–3300, 1664, 1635, 1626, 1604, 1570 cm$^{-1}$;

$^1$H-NMR (D$_2$O, δ): 1.30–2.10 (11H, m), 1.98 (3H, s), 2.35–2.60 (5H, m), 2.75–3.05 (3H, m), 3.10–3.50 (6H, m), 3.60–4.00 (2H, m), 4.10–4.45 (2H, m);

(+)-APCI/MS (m/z): 468 (M$^+$+1);

Anal. Calcd for $C_{22}H_{37}N_5O_6 \cdot 2.5H_2O$: C, 51.55; H, 8.26; N, 13.66. Found: C, 51.42, H, 8.52; N, 13.58.

(3) N-[(3R)-1-{3-(4-Piperidyl)propionyl}-3-piperidylcarbonyl]-2(R)-((3-acetylamnino)propionyl)amino-β-alanine IR (KBr) 3500–3300, 1658, 1635, 1627, 1606, 1570 cm$^{-1}$;

$^1$H-NMR (D$_2$O, δ): 1.25–2.05 (11H, m), 1.98 (3H, s), 2.30–2.60 (5H, m), 2.75–3.05 (3H, m), 3.10–3.55 (6H, m), 3.60–3.75 (1H, m), 3.80–3.40 (1H, m), 4.10–4.45 (2H, m);

(+)-APCI/MS (m/z): 468 (M$^+$+1);

Anal. Calcd for $C_{22}H_{37}N_5O_6 \cdot 2.4H_2O$: C, 51.73; H, 8.25; N, 13.71. Found: C, 51.96; H, 8.60; N, 13.73.

EXAMPLE 35

To a stirred solution of N-[(3R)-1-{3-(1-tert-butoxycarbonyl-4-piperidyl)propionyl}-3-piperidylcarbonyl]-2(S)-(2-aminoacetyl)amino-β-alanine (600 mg) and N-trimethylsilylacetoamide (770 mg) in acetonitrile (10 mL) was added terephtalic acid monomethyl ester chloride (233 mg) at 4° C. After stirring for 3 hours, the reaction mixture was acidified with 5% aqueous potassium hydrogensulfate solution and extracted with ethyl acetate. The organic layer was washed with brine and dried over magnesium sulfate. The organic layer was evaporated and the residue was treated with 4 N—HCl in ethyl acetate. The resulting insoluble material was collected by filtration, dried and dissolved in water. The solution was neutralized with an aqueous saturated sodium hydrogencarbonate solution, purified by ODS column chromatography (Daisogel-120sp®) eluting with 5, 10, 15 and 20% CH$_3$CN/H$_2$O and lyophilized to give N-[(3R)-1-{3-(4-piperidyl)propionyl}-3-piperidylcarbonyl]-2(S)-(2-((4-methoxycarbonylbenzoyl)amino)acetyl)amino-β-alanine (500.5 mg, 74.6%) as an amorphous powder.

IR (KBr) 3555–3280, 1720, 1655, 1639, 1625, 1552, 1500 cm$^{-1}$;

$^1$H-NMR (D$_2$O, δ): 1.20–2.05 (11H, m), 2.20–2.50 (3H, m), 2.50–2.70 (3H, m), 2.85–3.10 (3H, m), 3.35–3.55 (3H, m), 3.60–3.85 (2H, m), 3.97 (3H, s), 4.05–4.25 (1H, m), 4.16 (2H, s), 4.35–4.45 (1H, m), 7.97 (2H, d, J=8.2 Hz), 8.10–8.20 (2H, m);

(+)-APCI/MS (m/z): 547 (M$^+$+1).

EXAMPLE 36

The following compounds described in (1) to (3) were obtained in a manner similar to Example 35.

(1) N-[(3R)-1-{3-(4-Piperidyl)propionyl}-3-piperidylcarbonyl]-2(R)-(2-((4-methoxycarbonylbenzoyl)amino)acetyl)amino-β-alanine IR (KBr) 3555–3280, 1724, 1647, 1549, 1500 cm$^{-1}$;

$^1$H-NMR (D$_2$O, δ): 1.20–2.05 (11H, m), 2.20–2.70 (4H, m), 2.75–3.10 (3H, m), 3.30–3.55 (3H, m), 3.60–3.90 (2H, m), 3.97 (3H, s), 4.05–4.30 (1H, m), 4.15 (2H, s), 4.35–4.45 (1H, m), 7.90–8.05 (2H, m), 8.10–8.20 (2H, m);

(+)-APCI/MS (m/z): 547 (M$^+$+1).

(2) N-[(3R)-1-{3-(4-Piperidyl)propionyl}-3-piperidylcarbonyl]-2(S)-(3-((4-methoxycarbonylbenzoyl)amino)propionyl)amino-β-alanine IR (KBr) 3575–3270, 1724, 1643, 1549, 1500 cm$^{-1}$;

$^1$H-NMR (D$_2$O, δ): 1.20–2.05 (11H, m), 2.10–2.45 (3H, m), 2.50–2.80 (3H, m), 2.85–3.10 (3H, m), 3.30–3.50 (3H, m), 3.60–3.90 (4H, m), 3.96 (3H, s), 4.05–4.20 (1H, m), 4.30–4.45 (1H, m), 7.85 (2H, dd, J=8.5, 2.4 Hz), 8.10 (2H, dd, J=8.5, 2.1 Hz);

(+)-APCI/MS (m/z): 588 (M$^+$+1).

(3) N-[(3R)-1-{3-(4-Piperidyl)propionyl}-3-piperidylcarbonyl]-2(R)-(3-((4-methoxycarbonylbenzoyl)amino)propionyl)amino-β-alanine IR (KBr) 3575–3290, 1724, 1641, 1566, 1550, 1500 cm$^{-1}$;

$^1$H-NMR (D$_2$O, δ): 1.20–2.05 (11H, m), 2.10–2.45 (3H, m), 2.50–2.80 (3H, m), 2.85–3.10 (3H, m), 3.30–3.50 (3H, m), 3.60–3.90 (4H, m), 3.96 (3H, s), 4.05–4.25 (1H, m), 4.30–4.45 (1H, m), 7.80–7.90 (2H, m), 8.11 (2H, dd, J=8.5, 2.2 Hz);

(+)-APCI/MS (m/z): 588 (M$^+$+1).

EXAMPLE 37

To a solution of N-[(3R)-1-{3-(4-piperidyl)propionyl)3-piperidylcarbonyl]-2(S)-(2-((4-methoxycarbonylbenzoyl)amino)acetyl)-amino-β-alanine (340 mg) in tetrahydrofuran (10 mL) was added 1 N-aqueous sodium hydroxide solution (2.1 mL) at 4° C. After stirring for an hour, the reaction mixture was acidified with 20% aqueous potassium hydrogensulfate solution and extracted with ethyl acetate. The organic layer was washed with brine and dried over magnesium sulfate. The organic layer was evaporated and the residue was dissolved in water. Thus obtained solution was neutralized with an aqueous saturated sodium hydrogencarbonate solution, purified by ODS column chromatography (Daisogel-120sp®) eluting with 2, 4, 6, 8, 10 and 15% CH$_3$CN/H$_2$O and lyophilized to give N-[(3R)-1-{3-(4-piperidyl)propionyl}-3-piperidylcarbonyl]-2(S)-(2-((4-carboxybenzoyl)amino)acetyl)amino-β-alanine (305 mg, 92.4%) as an amorphous powder.

IR (KBr) 3570–3200, 1644, 1546, 1500 cm$^{-1}$;

$^1$H-NMR (D$_2$O, δ): 1.20–2.00 (11H, m), 2.15–2.45 (3H, m), 2.50–2.70 (1H, m), 2.80–3.05 (3H, m), 3.30–3.60 (3H, m), 3.60–3.80 (2H, m), 4.05–4.25 (1H, m), 4.13 (2H, s), 4.40–4.45 (1H, m), 7.90–8.10 (4H, m);

(+)-APCI/MS (m/z): 560 (M$^+$+1);

Anal. Calcd for $C_{27}H_{37}N_5O_8 \cdot 2.8H_2O$: C, 53.16; H, 7.04; N, 11.48. Found: C, 53.11; H, 6.94; N, 11.40.

EXAMPLE 38

The following compounds described in (1) to (3) were obtained in a manner similar to Example 37.

(1) N-(3R)-1-{3-(4-Piperidyl)propionyl}-3-piperidylcarbonyl]-2(R)-(2-((4-carboxybenzoyl)amino)acetyl)amino-β-alanine IR (KBr) 3570–3200, 1645, 1546, 1500 cm$^{-1}$;

$^1$H-NMR (D$_2$O, δ): 1.20–2.00 (11H, m), 2.15–2.45 (3H, m), 2.50–2.70 (1H, m), 2.80–3.05 (3H, m), 3.30–3.60 (3H, m), 3.60–3.80 (2H, m), 4.05–4.25 (1H, m), 4.13 (2H, s), 4.40–4.45 (1H, m), 7.90–8.10 (4H, m);

(+)-APCI/MS (m/z): 560 (M$^+$+1);

Anal. Calcd for $C_{27}H_{37}N_5O_8 \cdot 2.8H_2O$: C, 53.16; H, 7.04; N, 11.48. Found: C, 53.11; H, 6.89; N, 11.40.

(2) N-[(3R)-1-{3-(4-Piperidyl)propionyl}-3-piperidylcarbonyl]-2(S)-(3-((4-carboxybenzoyl)amino)propionyl)amino-β-alanine IR (KBr) 3510–3230, 1708, 1641, 1549 cm$^{-1}$;

$^1$H-NMR (D$_2$O, δ): 1.10–2.45 (14H, m), 2.50–2.80 (3H, m), 2.85–3.15 (3H, m), 3.30–3.55 (3H, m), 3.60–3.85 (4H, m), 4.00–4.15 (1H, m), 4.10–4.50 (1H, m), 7.75–7.85 (2H, m), 7.95–8.05 (2H, m);

(+)-APCI/MS (m/z): 574 (M$^+$+1);

Anal. Calcd for $C_{28}H_{39}N_5O_8 \cdot 2.7H_2O$: C, 54.04; H, 7.19; N, 11.25. Found: C, 54.17; H, 7.09; N, 11.21.

(3) N-[(3R)-1-{3-(4-Piperidyl)propionyl}-3-piperidylcarbonyl]-2(R)-(3-((4-carboxybenzoyl)amino)propionyl)amino-β-alanine IR (KBr) 3510–3230, 1709, 1641, 1549 cm$^{-1}$;

$^1$H-NMR (D$_2$O, δ): 1.10–2.45 (14H, m), 2.50–2.80 (3H, m), 2.85–3.20 (3H, m), 3.30–3.55 (3H, m), 3.60–3.85 (4H, m), 4.00–4.20 (1H, m), 4.40–4.55 (1H, m), 7.75–7.85 (2H, m), 7.95–8.05 (2H, m);

(+)-APCI/MS (m/z): 574 (M$^+$+1);

Anal. Calcd for $C_{28}H_{39}N_5O_8 \cdot 2.7H_2O$: C, 54.04; H, 7.19; N, 11.25. Found: C, 53.71; H, 7.07; N, 11.25.

EXAMPLE 39

A mixture of N-[(3R)-1-{3-(1-tert-butoxycarbonyl-4-piperidyl)propionyl}-3-piperidylcarbonyl]-2(S)-amino-β-alanine (230 mg, 0.51 mmol) and N-(trimethylsilyl)acetamide (0.9 g) in CH$_3$CN (7 mL) was stirred for 30 minuets at 40° C. After stirring for additional 30 minutes at room temperature, the solution of isobutoxybenzoyl chloride, which was prepared by chlorination of isobutoxybenzoic acid (116 mg, 0.60 mmol) with dimethylformamide (46 μl, 0.60 mmol) and oxaryl chloride (52 μl, 0.60 mmol) in dichloromethane (2 mL) at 5° C., was added to the reaction mixture. After stirring for an hour, the reaction was quenched with water. The mixture was acidified to pH 2 with 20% aqueous NaHSO$_4$ solution and extracted with Ethyl acetate. The organic layer was dried over Na$_2$SO$_4$ and evaporated in vacuo. The oily residue was dissolved in Ethyl acetate (10 mL) and the solution was treated with 4 N—HCl solution in Ethyl acetate. After stirring for 2 hours, the solvent was removed by decantation. The residue was dissolved in water. The solution was neutralized to pH 6.5 with an aqueous saturated NaHCO$_3$ solution, and purified by ODS-chromatography (Disogel SP120®) eluting with 10% CH$_3$CN/water. The collected eluent was concentrated in vacuo and lyophilized to afford N-[(3R)-1-{3-(4-piperidyl)propionyl}-3-piperidylcarbonyl]-2(S)-(4-isobutoxyoxybenzoyl)amino-β-alanine (175 mg, 54.9%) as a white amorphous powder.

IR (KBr):3448, 1631, 1606, 1548, 1502 cm$^{-1}$;

$^1$H-NMR (D$_2$O,δ):1.00 (6H, d, J=6.7 Hz), 1.30–2.44(15H, m), 2.69–3.43(6H, m), 3.58–3.78(3H, m), 3.91(2H, d, J=6.7 Hz), 4.05–4.19(1H, m), 7.06–7.13(2H, m), 7.76–7.82(2H, m);

(+)-APCI/MS (m/z): 531 (M$^+$+1).

EXAMPLE 40

N-[(3R)-1-{3-(4-piperidyl)propionyl}-3-piperidylcarbonyl]-2(R)-(4-isobutoxybenzoyl)amino-β-alanine was in a manner similar to Example 39

IR (KBr):3421, 1633, 1608, 1550, 1502 cm$^{-1}$;

$^1$H-NMR (D$_2$O,δ):1.01 (6H, d, J=6.7 Hz), 1.03–2.43(15H, m), 2.73–3.40(4H, m), 3.53–3.81(5H, m), 3.92(2H, d, J=6.7 Hz), 4.09–4.21(1H, m), 7.10(2H, d, J=8.6 Hz), 7.80(2H, d, J=8.6 Hz);

(+)-APCI/MS (m/z): 531(M$^+$+1).

EXAMPLE 41

To a solution of ethyl N-{1-[3-[1-(tert-butoxycarbonyl)4-piperidinyl)propionyl]-2H-1,3,4,7-terahydroazepine-3-carbonyl}-β-alanine methyl ester (0.23 g, 0.60 mmol) in THF (5 mL) was added 1 N aqueous LiOH solution (1.8 mL). After stirring for an hour, the mixture was acidified to pH 2.5 with 20% aqueous KHSO$_4$ solution, and extracted with ethyl acetate. The extract was dried over Na$_2$SO$_4$ and evaporated in vacuo. The residue was dissolved in ethyl acetate (6 mL). To the solution was added 4N hydrogen chloride in ethyl acetate (3 mL). After the mixture was stirred for an hour, the solvent was removed by decantation. The residue was dried in vacuo and dissolved in water. The solution was neutralized with a saturated aqueous NaHCO$_3$ solution, then purified by Daisogel SP-120® (Daiso) reversed phase gel chromatography eluting with a mixture of CH$_3$CN and water (1:10). The fractions contained a product was concentrated in vacuo and freeze-dried to give N-{1-[3-(4-piperidinyl)propionyl]-1H-2,5,6,7-terahydroazepine-3-carbonyl}-β-alanine (130 mg, 0.37 mmol, 61.7%) as a white powder.

IR (film) 1630, 1567, 1465, 1402 cm$^{-1}$;

$^1$H-NMR (CDCl$_3$, δ): 1.36–1.61 (5H, m), 1.94–2.01 (2H, m), 2.36–2.54 (6H, m), 2.91–3.04 (3H, m), 3.37–3.47 (4H, m), 3.79–3.88 (2H, m), 4.02–4.23 (2H, m), 5.64–5.72 (1H, m), 5.72–5.93 (2H, m);

MASS (m/z): 352 [M+1]$^+$.

EXAMPLE 42

N-{1-[3-(4-Piperidinyl)propionyl-1,2,3,6,7,8-hexahydroazocine-7-carbonyl}-β-alanine was obtained in a manner similar to Example 41.

$^1$H-NMR (CDCl$_3$, δ): 1.36–1.62 (5H, m), 1.93–2.00 (2H, m), 2.24–2.46 (8H, m), 2.92–3.46 (9H, m), 3.79–4.23 (2H, m), 5.71–5.90 (2H, m);

MASS (m/z): 366 [M+1]$^+$.

EXAMPLE 43

A mixture of N-{1-[3-(4-piperidinyl)propionyl]-2H-1,3,4,7-terahydroazepine-3-carbonyl}-β-alanine (70 mg, 199 mmol) and PtO$_2$ (10 mg) in methanol (5 mL) was hydrogenated under hydrogen gas atmosphere (1 atm) for 8 hours. The catalyst was removed by filtration, then the filtrate was evaporated in vacuo. The residue was purified by Daisogel SP-120® (Daiso) reversed phase chromatography eluting with a mixture of $CH_3CN$ and water (1:10). The fractions containing a product were concentrated in vacuo and freeze-dried to give N-{1-[3-(4-piperidinyl)propionyl]-1H-2,3,4,5,6,7-hexahydroazepine-3-carbonyl}-β-alanine (61 mg, 172 mmol, 86.4%) as a white powder.

$^1$H-NMR ($CDCl_3$, δ): 1.37–2.01 (13H, m), 2.36–2.64 (5H, m), 2.93–3.05 (2H, m), 3.21–3.94 (8H, m);

MASS (m/z) 354 $[M+1]^+$.

EXAMPLE 44

N-{1-[3-(4-Piperidinyl)propionyl-1,2,3,4,5,6,7,8-octahydroazocine-7-carbonyl}-β-alanine was obtained in a manner similar to Example 43.

$^1$H-NMR ($CDCl_3$, δ): 1.38–2.05 (15H, m), 2.36–2.50 (4H, m), 2.92–3.05 (3H, m), 3.29–3.47 (6H, m), 3.71–3.83 (2H, m);

MASS (m/z): 368 $[M+1]^+$.

EXAMPLE 45

To a mixture of N-[1-(tert-butoxycarbonyl)-1H-2,5,6,7-tetrahydroazepine-6(R)-carbonyl]-2(S)-(benzyloxycarbonylamino)-β-alanine methyl ester (90 mg, 0.19 mmol) was added 4N-hydrogen chloride in ethyl acetate solution (1 mL). After the mixture was stirred for an hour, the solvent was removed by decantation. The residue was dried in vacuo and dissolved in DMF (2 mL). To the solution were added 1-(tert-butoxycarbonyl)-piperidine-4-carboxylic acid (54 mg, 0.21 mmol), 1-hydroxybenztriazole (HOBT) (28 mg, 0.21 mmol) and 1-ethyl-3-(3-dimethylaminopropyl)carbodiimide (WSC) (100 mL, 0.55 mmol). After stirring overnight, the mixture was quenched by a saturated aqueous $NaHCO_3$ solution, then extracted with ethyl acetate. The extract was washed with water and brine, dried over $Na_2SO_4$ and evaporated in vacuo. The residue (71 mg) and Pd on Carbon (20 mg, 50% wet) were dissolved in methanol (10 mL). The mixture was hydrogenated with 1 atm of hydrogen atmosphere. After string for 3 hours, 1N LiOH solution (0.5 mL) was added to the mixture at 0° C. Acetic anhydride (28 mL, 0.3 mmol) was added successively after 30 minutes. The mixture was acidified to pH 2.5 with 20% aqueous $KHSO_4$ solution, and extracted with ethyl acetate. The extract was dried over $Na_2SO_4$ and evaporated in vacuo. The residue was dissolved in ethyl acetate (2 mL), then 4N hydrogen chloride solution in ethyl acetate (1 mL) was added. After the mixture was stirred for an hour, the solvent was removed by decantation. The residue was dried in vacuo, and dissolved in water. The solution was neutralized with a saturated aqueous $NaHCO_3$ solution, then purified by Daisogel SP-120® (Daiso) reversed phase gel chromatography eluting with a mixture of $CH_3CN$ and water (1:10). The fractions containing a product were concentrated in vacuo and freeze-dried to give N-[1-[3-(4-piperidinyl)propionyl]-1H-2,3,4,5,6,7-hexahydroazepine-7(R)-carbonyl]-2(S)-(acetylamino)-β-alanine (28 mg, 68 mmol, 36.1%) as a white powder.

IR (KBr) 3122, 1623, 1550, 1436 $cm^{-1}$;

$^1$H-NMR ($CDCl_3$, δ): 1.32–1.94 (13H, m), 2.03 (3H, s), 2.45–2.65 (3H, m), 2.92–2.99 (2H, m), 3.30–3.72 (8H, m), 4.34–4.41 (1H, m);

MASS (m/z): 411 $[M+1]^+$.

EXAMPLE 46

To a solution of N-[(R)-1-{3-(1-tert-butoxycarbonyl-4-piperidyl)propionyl}-3-piperidylcarbonyl]-2(S)-amino-β-alanine (382 mg, 0.84 mmol) in acetoiltrile (5 mL) was added monosilylacetamide (1.1 g, 84 mmol), then the mixture was warmed up to 40° C. After stiing for 30 minutes, the reaction mixture was cooled under ice water bath, then benzyloxyacetyl chloride (133 mL) was added. After stirring for 30 minutes at room temperature, the mixture was acidified with 20% aqueous $KHSO_4$ solution, extracted with ethyl acetate and dried over sodium sulfate. After evaporation of the solvent, the residue was treated with 4N-hydrochloric acid in ethyl acetate. Insoluble material was collected by filtration, dried and dissolved in water. The solution was neutralized with a saturated aqueous $NaHCO_3$ solution, purified by an ODS column chromatography using Daisogel-120sp (10% $CH_3CN/H_2O$) and freeze-dried to give N-[3(R)-1-{3-(4-piperidyl)propionyl}-3-piperidylcarbonyl]-2(S)-(benzyloxyacetyl)amino-β-alanine (370 mg, 87.6%) as a white powder.

$^1$H-NMR ($D_2O$, δ): 1.35–1.98 (11H, m), 2.37–2.72 (3H, m), 2.78–3.12 (4H, m), 3.38–3.78 (5H, m), 4.07–4.17 (3H, m), 4.35–4.39 (1H, m), 4.59–4.67 (2H, m), 7.43–7.49 (5H, m);

MASS (m/z): 503 $[M+H]^+$.

EXAMPLE 47

The following compounds (1) to (22) were obtained in a manner similar to example 46.

(1) N-[3(R)-1-{3-(4-Piperidyl)propionyl}-3-piperidylcarbonyl]-2(R)-(benzyloxyacetyl)amino-β-alanine $^1$H-NMR ($D_2O$, δ): 1.31–1.95 (11H, m), 2.24–2.46 (3H, m), 2.60–3.11 (4H, m), 3.33–3.50 (3H, m), 3.62–3.83 (2H, m), 4.07 (2H, s), 4.13–4.26 (1H, m), 4.32–4.37 (1H, m), 4.56–4.69 (2H, m), 7.39–7.43 (5H, m);

MASS (m/z): 503 $[M+H]^+$.

(2) N-[3(R)-1-{3-(4-Piperidyl)propionyl}-3-piperidylcarbonyl]-2(S)-(4-cyanobenzoyl]amino-β-alanine IR (KBr) 1641, 1629, 1610, 1535 $cm^{-1}$.

$^1$H-NMR ($D_2O$, δ): 1.37–1.98 (11H, m), 2.28–2.48 (3H, m), 2.79–3.24 (4H, m), 3.29–3.45 (2H, m), 3.60–3.83 (3H, m), 4.12–4.18 (1H, m), 4.58–4.67 (1H, m), 7.88–7.96 (4H, m);

MASS (m/z): 484 $[M+H]^+$.

(3) N-[3(R)-1-{3-(4-Piperidyl)propionyl}-3-piperidylcarbony]-2(R)-(4-cyanobenzoyl)amino-β-alanine IR (KBr) 1641, 1629, 1610, 1533 $cm^{-1}$;

$^1$H-NMR ($D_2O$, δ): 1.41–1.98 (11H, m), 2.38–2.46 (3H, m), 2.79–3.32 (4H, m), 3.38–3.43 (2H, m), 3.56–3.80 (3H, m), 4.09–4.27 (1H, m), 4.61–4.69 (1H, m), 7.92–7.93 (4H, m);

MASS (m/z): 484 $[M+H]^+$.

(4) N-[3(R)-1-{3-(4-Piperidyl)propionyl}-3-piperidylcarbonyl]-2(S)-(4-nitrobenzoyl)amino-β-alanine IR (KBr) 1660, 1639, 1627, 1600, 1567, 1550, 1531 $cm^{-1}$;

$^1$H-NMR ($D_2O$, δ): 1.36–1.98 (11H, m), 2.30–2.48 (3H, m), 2.79–3.02 (3H, m), 3.16–3.44 (3H, m), 3.57–3.84 (3H, m), 4.12–4.18 (1H, m), 4.59–4.68 (1H, m), 7.98 (2H, d, J=8.8 Hz), 8.37 (2H, dd, J=2.8, 8.8 Hz);

MASS (m/z): 504 $[M+H]^+$.

(5) N-[3(R)-1-{3-(4-Piperidyl)propionyl}-3-piperidylcarbonyl]-2(R)-(4-nitrobenzoyl)amino-β-alanine IR (KBr) 1660, 1639, 1627, 1600, 1567, 1550, 1529 $cm^{-1}$;

$^1$H-NMR ($D_2O$, δ): 1.34–1.98 (11H, m), 2.30–2.47 (3H, m), 2.84–3.43 (6H, m), 3.62–3.83 (3H, m), 4.08–4.23 (1H, m), 4.62–4.70 (1H, m), 7.99 (2H, d, J=8.8 Hz), 8.37 (2H, d, J=8.8 Hz);

MASS (m/z): 504 [M+H]⁺.

(6) N-[3(R)-1-{3-(4-Piperidyl)propionyl}-3-piperidylcarbonyl]-2(S)-(3-methoxybenzoyl)amino-β-alanine ¹H-NMR (D₂O, δ): 1.26–1.95 (11H, m), 2.19–2.44 (3H, m), 2.69–3.00 (3H, m), 3.08–3.42 (3H, m), 3.51–3.81 (3H, m), 3.88 (3H, s), 4.08–4.23 (1H, m), 4.59–4.69 (1H, m), 7.18–7.52 (4H, m);

MASS (m/z): 489 [M+H]⁺.

(7) N-[3(R)-1-{3-(4-Piperidyl)propionyl}-3-piperidylcarbonyl]-2(R)-(3-methoxybenzoyl)amino-β-alanine ¹H-NMR (D₂O, δ): 1.26–1.96 (11H, m), 2.29–2.44 (3H, m), 2.78–3.45 (6H, m), 3.53–3.83 (3H, m), 3.86 (3H, s), 4.10–4.18 (1H, m), 4.60–4.72 (1H, m), 7.19–7.53 (4H, m);

MASS (m/z): 489 [M+H]⁺.

(8) N-[3(R)-1-{3-(4-Piperidyl)propionyl}-3-piperidylcarbonyl]-2(S)-(2-methoxybenzoyl)amino-β-alanine ¹H-NMR (D₂O, δ): 1.39–1.96 (11H, m), 2.24–2.41 (3H, m), 2.85–3.38 (6H, m), 3.52–3.82 (3H, m), 3.89 (3H, s), 4.01–4.10 (1H, m), 4.57–4.63 (1H, m), 7.11–7.23 (2H, m), 7.56–7.64 (1H, m), 7.89–7.93 (1H, m);

MASS (m/z): 489 [M+H]⁺.

(9) N-[3(R)-1-{3-(4-Piperidyl)propionyl}-3-piperidylcarbonyl]-2(R)-(2-methoxybenzoyl)amino-β-alanine ¹H-NMR (D₂O, δ): 1.34–1.97 (11H, m), 2.38–2.46 (3H, m), 2.74–3.65 (7H, m), 3.77–3.83 (2H, m), 4.00 (3H, s), 4.01–4.29 (1H, m), 4.57–4.67 (1H, m), 7.10–7.23 (2H, m), 7.56–7.63 (1H, m), 7.85–7.93 (1H, m);

MASS (m/z): 489 [M+H]⁺.

(10) N-[3(R)-1-{3-(4-Piperidyl)propionyl}-3-piperidylcarbonyl]-2(S)-(n-butoxycarbonyl)amino-β-alanine IR (KBr) 3446, 2958, 1700, 1616, 1548, 1469, 1446 cm⁻¹;

¹H-NMR (D₂O, δ): 0.90 (3H, t, J=7.4 Hz), 1.34–2.01 (15H, m), 2.47–2.54 (3H, m), 2.91–3.05 (3H, m), 3.39–3.64 (4H, m), 4.06–4.30 (6H, m);

MASS (m/z): 455 [M+H]⁺.

(11) N-[3(R)-1-{3-(4-Piperidyl)propionyl}-3-piperidylcarbonyl]-2(R)-(n-butoxycarbonyl)amino-β-alanine IR (KBr) 3413, 2958, 1702, 1619, 1545, 1469, 1446 cm⁻¹;

¹H-NMR (D₂O, δ): 0.95 (3H, t, J=7.4 Hz), 1.31–2.01 (15H, m), 2.47–2.54 (3H, m), 2.91–3.05 (3H, m), 3.39–3.46 (4H, m), 4.05–4.20 (6H, m);

MASS (m/z): 455 [M+H]⁺.

(12) N-(3(R)-1-{3-(4-Piperidyl)propionyl}-3-piperidylcarbonyl]-2(S)-(ethoxycarbonylacetyl)amino-β-alanine ¹H-NMR (D₂O, δ): 1.27 (3H, t, J=7.1 Hz), 1.43–2.01 (11H, m), 2.51–2.54 (3H, m), 2.83–3.03 (3H, m), 3.23–3.50 (4H, m), 3.66–3.89 (2H, m), 4.16–4.27 (3H, m), 4.38–4.45 (1H, m);

MASS (m/z): 469 [M+H]⁺.

(13) N-[3(R)-1-{3-(4-Piperidyl)propionyl}-3-piperidylcarbonyl]-2(R)-(ethoxycarbonylacetyl)amino-β-alanine IR (KBr) 3421, 1648, 1602, 1552, 1442 cm⁻¹;

¹H-NMR (D₂O, δ): 1.27 (3H, t, J=7.1 Hz), 1.43–2.02 (11H, m), 2.47–2.54 (3H, m), 2.83–3.03 (3H, m), 3.18–3.91 (6H, m), 4.16–4.27 (3H, m), 4.38–4.46 (1H, m);

MASS (m/z): 469 [M+H]⁺.

(14) N-[3(R)-1-{3-(4-Piperidyl)propionyl}-3-piperidylcarbonyl]-2(S)-(acetoxyacetyl)amino-β-alanine IR (KBr) 3407, 1745, 1616, 1550, 1465 cm⁻¹;

¹H-NMR (D₂O, δ): 1.36–2.01 (11H, m), 2.22 (3H, s), 2.47–2.54 (3H, m), 2.85–3.05 (3H, m), 3.21–3.53 (4H, m), 3.65–3.89 (2H, m), 4.23–4.30 (1H, m), 4.40–4.46 (1H, m), 4.65 (2H, s);

MASS (m/z): 455 [M+H]⁺.

(15) N-[3(R)-1-{3-(4-Piperidyl)propionyl}-3-piperidylcarbonyl]-2(R)-(acetoxyacetyl)amino-β-alanine IR (KBr) 3421, 1745, 1647, 1614, 1550, 1465 cm⁻¹;

¹H-NMR (D₂O, δ): 1.32–1.97 (11H, m), 2.18 (3H, s), 2.43–2.50 (3H, m), 2.79–3.01 (3H, m), 3.14–3.70 (4H, m), 3.87–4.26 (2H, m), 4.38–4.41 (2H, m), 4.62 (2H, s);

MASS (m/z): 455 [M+H]⁺.

(16) N-[3(R)-1-{3-(4-Piperidyl)propionyl}-3-piperidylcarbonyl]-2(S)-(methoxyacetyl)amino-β-alanine IR (KBr) 3442, 1648, 1616, 1548, 1465 cm⁻¹;

¹H-NMR (D₂O, δ): 1.37–1.97 (11H, m), 2.46–2.54 (3H, m), 2.89–3.04 (3H, m), 3.20–3.53 (4H, m), 3.46 (3H, s), 3.71–3.88 (2H, m), 4.01 (2H, s), 4.14–4.30 (1H, m), 4.38–4.44 (1H, m);

MASS (m/z): 427 [M+H]⁺.

(17) N-[3(R)-1-{3-(4-Piperidyl)propionyl}-3-piperidylcarbonyl]-2(R)-(methoxyacetyl)amino-β-alanine ¹H-NMR (D₂O, δ): 1.37–2.01 (11H, m), 2.47–2.54 (3H, m), 2.89–3.32 (4H, m), 3.39–3.56 (3H, m), 3.46 (3H, s), 3.64–3.77 (1H, m), 3.90–4.01 (1H, m), 4.16 (2H, s) 4.22–4.45 (2H, m);

MASS (m/z): 427 [M+H]⁺.

(18) N-[3(R)-1-{3-(4-Piperidyl)propionyl}-3-piperidylcarbonyl]-2(S)-[N-(isobutyloxycarbonyl)-β-alaninyl]amino-β-alanine ¹H-NMR (D₂O, δ): 0.90 (6H, d, J=6.8 Hz), 1.37–2.01 (12H, m), 2.40–2.53 (5H, m), 2.78–3.05 (3H, m), 3.14–3.50 (6H, m), 3.62–3.85 (4H, m), 4.17–4.41 (2H, m);

MASS (m/z): 526 [M+H]⁺.

(19) N-[3(R)-1-{3-(4-Piperidyl)propionyl}-3-piperidylcarbonyl]-2(R)-[N-(isobutyloxycarbonyl)-β-alaninyl]amino-β-alanine ¹H-NMR (D₂O, δ): 0.90 (6H, d, J=6.8 Hz), 1.37–2.01 (12H, m), 2.47–2.53 (5H, m), 2.84–3.05 (3H, m), 3.12–3.45 (6H, m), 3.61–3.91 (4H, m), 4.17–4.42 (2H, m);

MASS (m/z): 526 [M+H]⁺.

(21) N-[3(R)-1-{3-(4-Piperidyl)propionyl}-3-piperidylcarbonyl]-2(S)-[N-(isobutyloxycarbonyl) glycinyl]amino-β-alanine ¹H-NMR (D₂O, δ): 0.91 (6H, d, J=6.7 Hz), 1.43–1.73 (12H, m), 2.47–2.54 (3H, m), 2.88–3.04 (3H, m), 3.21–3.46 (4H, m), 3.66–3.76 (1H, m), 3.86–3.90 (5H, m), 4.26–4.38 (2H, m);

MASS (m/z): 512 [M+H]⁺.

(22) N-[3(R)-1-{3-(4-Piperidyl)propionyl}-3-piperidylcarbonyl]-2(R)-[N-(isobutyloxycarbonyl) glycinyl]amino-β-alanine ¹H-NMR (D₂O, δ): 0.92 (6H, d, J=6.7 Hz), 1.43–1.73 (12H, m), 2.47–2.54 (3H, m), 2.83–3.05 (3H, m), 3.17–3.53 (4H, m), 3.65–3.73 (1H, m), 3.86–3.91 (5H, m), 4.10–4.38 (2H, m);

MASS (m/z): 512 [M+H]⁺.

EXAMPLE 48

To a solution of N-[(R)-1-{3-(1-tert-butoxycarbonyl-4-piperidyl)propionyl}-3-piperidylcarbonyl]-2(S)-amino-β-alanine (244 mg, 0.49 mmol) in DMF (2.5 mL) was added monosilylacetamide (0.65 g, 4.9 mmol) at 5° C. After stirring for 30 minutes, a solution of 1-(4-methoxycarbonyl)

benzoyloxybenztriazole (0.55 mmol) in DMF (1.0 mL) was added thereto. After stirring for 1.5 hour, the mixture was acidified with 20% aqueous $KHSO_4$ solution, extracted with ethyl acetate, and dried over sodium sulfate. After evaporation of the solvent, the residue was treated with 4N hydrochloric acid in ethyl acetate. The insoluble material was collected by filtration, dried and dissolved in water. The solution was neutralized with a saturated aqueous $NaHCO_3$ solution, purified by an ODS column chromatography using Daisogel-120sp (10% $CH_3CN/H_2O$) and freeze-dried to give N-[(R)-1-{3-(4-piperidyl)propionyl}-3-piperidylcarbonyl]-2(S)-(4-methoxycarbonylbenzoyl)amino-β-alanine (120 mg, 47.4%) as a white powder.

$^1$H-NMR ($D_2O$, δ): 1.33–1.96 (11H, m), 2.26–2.46 (3H, m), 2.86–2.99 (3H, m), 3.15–3.44 (3H, m), 3.64–3.76 (3H, m), 3.96 (3H, s), 4.11–4.15 (1H, m), 4.61–4.66 (1H, m), 7.86–7.90 (2H, m), 8.09–8.15 (2H, m);
MASS (m/z): 517 [M+1]$^+$.

EXAMPLE 49

The following compounds (1) to (41) were obtained in a manner similar to example 48.

(1) N-[(R)-1-{3-(4-Piperidyl)propionyl}-3-piperidylcarbonyl]-2(R)-(4-methoxycarbonylbenzoyl)amino-β-alanine
$^1$H-NMR ($D_2O$, δ): 1.27–1.89 (11H, m), 2.34–2.45 (3H, m), 2.90–3.40 (6H, m), 3.65–3.84 (3H, m), 3.96 (3H, s), 4.05–4.25 (1H, m), 4.64–4.69 (1H, m), 7.89 (2H, d, J=8.4 Hz), 8.14 (2H, dd, J=1.7, 8.4 Hz).
MASS (m/z): 517 [M+1]$^+$.

(2) N-[(R)-1-{3-(4-Piperidyl)propionyl}-3-piperidylcarbonyl]-2(S)-(1,2,3-thiadiazole-5-carbonyl)amino-β-alanine
IR (KBr) 1660, 1639, 1627, 1610, 1550, 1533 cm$^{-1}$;
$^1$H-NMR ($D_2O$, δ): 1.41–1.99 (11H, m), 2.41–2.46 (3H, m), 2.84–3.46 (6H, m), 3.57–3.91 (3H, m), 4.08–4.20 (1H, m), 4.64–4.69 (1H, m), 9.53 (1H, s);
MASS (m/z): 467 [M+1]$^+$.

(3) N-[(R)-1-{3-(4-Piperidyl)propionyl}-3-piperidylcarbonyl]-2(R)-(1,2,3-thiadiazole-5-carbonyl)amino-β-alanine
IR (KBr) 1660, 1639, 1627, 1610, 1550, 1533 cm$^{-1}$;
$^1$H-NMR ($D_2O$, δ): 1.36–1.99 (11H, m), 2.41–2.49 (3H, m), 2.81–3.46 (6H, m), 3.57–3.94 (3H, m), 4.05–4.25 (1H, m), 4.68–4.70 (1H, m), 9.54 (1H, s);
MASS (m/z): 467 [M+1]$^+$.

(4) N-[(R)-1-{3-(4-Piperidyl)propionyl}-3-piperidylcarbonyl]-2(S)-[4-(N-isopentylcarboxamide)benzoyl]amino-β-alanine
$^1$H-NMR ($D_2O$, δ): 0.93 (6H, d, J=6.4 Hz), 1.41–1.99 (14H, m), 2.24–2.46 (3H, m), 2.84–2.96 (3H, m), 3.10–3.46 (5H, m), 3.65–3.74 (3H, m), 4.10–4.15 (1H, m), 4.62–4.66 (1H, m), 7.81–7.91 (4H, m);
MASS (m/z): 572 [M+1]$^+$.

(5) N-[(R)-1-{3-(4-Piperidyl)propionyl}-3-piperidylcarbonyl]-2(R)-[4-(N-isopentylcarboxamide)benzoyl]amino-β-alanine
$^1$H-NMR ($D_2O$, δ): 0.93 (6H, d, J=6.4 Hz), 1.25–1.88 (14H, m), 2.30–2.41 (3H, m), 2.74–3.00 (3H, m), 3.10–3.46 (5H, m), 3.65–3.83 (3H, m), 4.05–4.22 (1H, m), 4.64–4.70 (1H, m), 7.81–7.92 (4H, m);
MASS (m/z): 572 [M+1]$^+$.

(6) N-[(R)-1-{3-(4-Piperidyl)propionyl}-3-piperidylcarbonyl]-2(S)-[4-(N-isobutylcarboxamide)benzoyl]amino-β-alanine
IR (KBr) 3417, 1635, 1549, 1494, 1483 cm$^{-1}$;
$^1$H-NMR ($D_2O$, δ): 0.95 (6H, d, J=6.7 Hz), 1.39–1.95 (12H, m), 2.24–2.41 (3H, m), 2.77–2.92 (3H, m), 3.16–3.42 (5H, m), 3.65–3.81 (3H, m), 4.11–4.17 (1H, m), 4.61–4.69 (1H, m), 7.86–7.88 (4H, m);
MASS (m/z): 558 [M+1]$^+$.

(7) N-[(R)-1-{3-(4-Piperidyl)propionyl}-3-piperidylcarbonyl]-2(R)-[4-(N-isobutylcarboxamide)benzoyl]amino-β-alanine
IR (KBr) 3411, 1637, 1549, 1494, 1469 cm$^{-1}$;
$^1$H-NMR ($D_2O$, δ): 0.95 (6H, d, J=6.7 Hz), 1.32–1.95 (12H, m), 2.31–2.39 (3H, m), 2.83–3.00 (3H, m), 3.21–3.38 (5H, m), 3.54–3.82 (3H, m), 4.08–4.23 (1H, m), 4.61–4.72 (1H, m), 7.87–7.92 (4H, m);
MASS (m/z): 558 [M+1]$^+$.

(8) N-[(R)-1-{3-(4-Piperidyl)propionyl}-3-piperidylcarbonyl]-2(S)-[4-(N-n-butylcarboxamide)benzoyl]amino-β-alanine
$^1$H-NMR ($D_2O$, δ): 0.93 (3H, t, J=7.3 Hz), 1.25–1.97 (15H, m), 2.20–2.46 (3H, m), 2.72–3.00 (3H, m), 3.11–3.44 (5H, m), 3.57–3.80 (3H, m), 4.11–4.17 (1H, m), 4.58–4.69 (1H, m), 7.81–7.91 (4H, m);
MASS (m/z): 558 [M+1]$^+$.

(9) N-[(R)-1-{3-(4-Piperidyl)propionyl}-3-piperidylcarbonyl]-2(R)-[4-(N-n-butylcarboxamide)benzoyl]amino-β-alanine
$^1$H-NMR ($D_2O$, δ): 0.93 (3H, t, J=7.3 Hz), 1.25–1.96 (15H, m), 2.27–2.42 (3H, m), 2.74–3.01 (3H, m), 3.17–3.44 (5H, m), 3.54–3.85 (3H, m), 4.08–4.23 (1H, m), 4.61–4.72 (1H, m), 7.82–7.92 (4H, m);
MASS (m/z): 558 [M+1]$^+$.

(10) N-[(R)-1-{3-(4Piperidyl)propionyl}-3-piperidylcarbonyl]-2(S)-(4-isobutyloxycarbonylaminobenzoyl)amino-β-alanine
$^1$H-NMR (DMSO-$d_6$, δ): 0.93 (6H, t, J=6.7 Hz), 1.18–1.99 (12H, m), 2.30–2.80 (3H, m), 2.99–3.91 (13H, m), 4.21–4.27 (2H, m), 7.51–7.87 (6H, m), 9.90 (1H, br);
MASS (m/z): 574 [M+1]$^+$.

(11) N-[(R)-1-{3-(4-Piperidyl)propionyl}-3-piperidylcarbonyl]-2(R)-(4-isobutyloxycarbonylaminobenzoyl)amino-β-alanine
IR (KBr) 3419, 1722, 1631, 1608, 1531, 1473 cm$^{-1}$;
$^1$H-NMR ($D_2O$, δ): 0.84 (6H, d, J=6.7 Hz), 1.27–1.94 (12H, m), 2.16–2.26 (3H, m), 2.72–3.29 (6H, m), 3.41–3.66 (3H, m), 3.86 (2H, d, J=6.5 Hz), 4.01–4.08 (1H, m), 4.52–4.60 (1H, m), 7.40 (2H, dd, J=2.2, 8.6 Hz), 7.69 (2H, d, J=8.6 Hz);
MASS (m/z): 574 [M+1]$^+$.

(12) N-[(R)-1-{3-(4-Piperidyl)propionyl}-3-piperidylcarbonyl]-2(S)-(3-isobutyloxycarbonylaminobenzoyl)amino-β-alanine
$^1$H-NMR ($D_2O$, δ): 0.93 (6H, d, J=6.7 Hz), 1.23–1.98 (12H, m), 2.17–2.42 (3H, m), 2.86–3.38 (6H, m), 3.61–3.78 (3H, m), 3.94 (2H, d, J=6.6 Hz), 4.08–4.18 (1H, m), 4.60–4.65 (1H, m), 7.42–7.75 (4H, m);
MASS (m/z): 574 [M+1]$^+$.

(13) N-[(R)-1-{3-(4-Piperidyl)propionyl}-3-piperidylcarbonyl]-2(R)-(3-isobutyloxycarbonylaminobenzoyl)amino-β-alanine
$^1$H-NMR ($D_2O$, δ): 0.94 (6H, d, J=6.7 Hz), 1.24–2.00 (12H, m), 2.25–2.41 (3H, m), 2.85–3.45 (6H, m), 3.50–3.80 (3H, m), 3.95 (2H, d, J=6.6 Hz), 4.10–4.22 (1H, m), 4.64–4.75 (1H, m), 7.44–7.79 (4H, m);
MASS (m/z): 574 [M+1]$^+$.

(14) N-[(R)-1-{3-(4-Piperidyl)propionyl}-3-piperidylcarbonyl]-2(S)-(4-acetylaminobenzoyl)amino-β-alanine
IR (KBr) 3413, 1639, 1629, 1600, 1533, 1500 cm$^{-1}$;

¹H-NMR (D₂O, δ): 1.25–1.96 (11H, m), 2.19 (3H, s), 2.23–2.45 (3H, m), 2.70–3.26 (4H, m), 3.35–3.41 (2H, m), 3.57–3.81 (3H, m), 4.09–4.19 (1H, m), 4.56–4.71 (1H, m), 7.56–7.63 (2H, m), 7.77–7.83 (2H, m);
MASS (m/z): 516 [M+]⁺.

(15) N-[(R)-1-{3-(4-Piperidyl)propionyl}-3-piperidylcarbonyl]-2(R)-(4-acetylaminobenzoyl)amino-β-alanine
IR (KBr) 3413, 1639, 1629, 1600, 1533, 1500 cm⁻¹;
¹H-NMR (D₂O, δ): 1.26–1.96 (11H, m), 2.20 (3H, s), 2.28–2.43 (3H, m), 2.78–3.44 (6H, m), 3.56–3.83 (3H, m), 4.09–4.16 (1H, m), 4.59–4.70 (1H, m), 7.59 (2H, dd, J=3.2, 8.6 Hz), 7.80 (2H, d, J=8.6 Hz);
MASS (m/z): 516 [M+1]⁺.

(16) N-[(R)-1-{3-(4-Piperidyl)propionyl}-3-piperidylcarbonyl]-2(S)-(4-benzyloxybenzoyl)amino-β-alanine
¹H-NMR (D₂O, δ): 1.27–2.30 (14H, m), 2.44–3.03 (4H, m), 3.30–3.80 (5H, m), 4.05–4.11 (1H, m), 4.53–4.63 (1H, m), 4.67–5.01 (2H, m), 6.83–6.95 (2H, m), 7.11–7.23 (5H, m), 7.66–7.79 (2H, m);
MASS (m/z): 565 [M+1]⁺.

(17) N-[(R)-1-{3-(4-Piperidyl)propionyl}-3-piperidylcarbonyl]-2(R)-(4-benzyloxybenzoyl)amino-β-alanine
¹H-NMR (D₂O, δ): 1.34–1.93 (11H, m), 2.18–3.04 (7H, m), 3.30–3.70 (5H, m), 4.00–4.10 (1H, m), 4.18–4.24 (1H, m), 4.54–4.71 (2H, m), 6.83–6.90 (2H, m), 7.15–7.21 (5H, m), 7.66–7.78 (2H, m);
MASS (m/z): 565 [M+1]⁺.

(18) N-[(R)-1-{3-(4-Piperidyl)propionyl}-3-piperidylcarbonyl]-2(S)-(4-methoxycarbonylmethyloxy)amino-β-alanine
¹H-NMR (D₂O, δ): 1.41–1.97 (11H, m), 2.23–2.42 (3H, m), 2.74–3.42 (6H, m), 3.63–3.74 (3H, m), 3.82 (3H, s), 4.05–4.20 (1H, m), 4.59–4.63 (1H, m), 4.89 (2H, m), 7.08 (2H, dd, J=3.2, 8.8 Hz), 7.79 (2H, d, J=8.8 Hz);
MASS (m/z): 547 [M+1]⁺.

(19) N-[(R)-1-{3-(4-Piperidyl)propionyl}-3-piperidylcarbonyl]-2(R)-(4-methoxycarbonylmethyloxy)amino-β-alanine
¹H-NMR (D₂O, δ): 1.28–1.97 (11H, m), 2.35–2.45 (3H, m), 2.74–3.45 (6H, m), 3.53–3.78 (3H, m), 3.84 (3H, s), 4.09–4.26 (1H, m), 4.59–4.71 (1H, m), 4.81 (2H, s), 7.10 (2H, dd, J=1.4, 8.8 Hz), 7.79 (2H, d, J=8.8 Hz);
MASS (m/z): 547 [M+1]⁺.

(20) N-[3(R)-1-{3-(4-Piperidyl)propionyl}-3-piperidylcarbonyl]-2(S)-(n-amiloxycarbonyl)amino-β-alanine
¹H-NMR (D₂O, δ): 0.75–1.00 (3H, m), 1.20–2.10 (17H, m), 2.30–2.65 (3H, m), 2.75–3.10 (3H, m), 3.10–3.55 (4H, m), 3.66 (1H, dd, J=13.9, 4.3 Hz), 3.75–4.40 (5H, m);
(+)-APCI/MS (m/z): 469 [M+H]⁺.

(21) N-[3(R)-1-{3-(4-Piperidyl)propionyl}-3-piperidylcarbonyl]-2(R)-(n-amiloxycarbonyl)amino-β-alanine
¹H-NMR (D₂O, δ): 0.89 (3H, t, J=6.9Hz), 1.15–2.10 (17H, m), 2.30–2.65 (3H, m), 2.75–3.10 (3H, m), 3.10–3.55 (4H, m), 3.55–3.80 (1H, m), 3.80–4.50 (5H, m).
(+)-APCI/MS (m/z): 469 [M+H]⁺.

(22) N-[3(R)-1-{3-(4-Piperidyl)propionyl}-3-piperidylcarbonyl]-2(S)-{4-(N-isopropylacetamidoxy)}phenylcarbonylamino-β-alanine
¹H-NMR (D₂O, δ): 1.15 (6H, d, J=6.6Hz), 1.20–2.05 (11H, m), 2.10–2.55 (3H,m), 2.60–3.25 (4H, m), 3.25–3.50 (2H, m), 3.50–3.90 (3H, m), 3.90–4.30 (2H, m), 4.50–4.75 (3H, m), 7.09 (2H, d, J=8.9 Hz), 7.80 (2H, d, J=8.8 Hz);
(+)-APCI/MS (m/z): 574 [M+H]⁺.

(23) N-[3(R)-1-{3-(4-Piperidyl)propionyl}-3-piperidylcarbonyl]-2(R)-{4-(N-isopropylacetamidoxy)}phenylcarbonylamino-β-alanine
¹H-NMR (D₂O, δ): 1.16 (6H, d, J=6.6 Hz), 1.20–2.05 (11H, m), 2.25–2.55 (3H, m), 2.70–3.90 (9H, m), 3.90–4.30 (2H, m), 4.50–4.70 (3H, m), 7.09 (2H, d, J=8.7 Hz), 7.81 (2H, d, J=8.8 Hz);
(+)-APCI/MS (m/z): 574 [M+H]⁺.

(24) N-[3(R)-1-{3-(4-Piperidyl)propionyl}-3-piperidylcarbonyl]-2(S)-[{4-(n-butylacetamidoxy)phenyl}carbonyl]amino-β-alanine
¹H-NMR (D₂O, δ): 0.85 (3H, t, J=7.2 Hz), 1.10–2.10 (15H, m), 2.15–2.60 (3H, m), 2.65–3.05 (4H, m), 3.05–3.30 (3H, m), 3.30–3.50 (2H, m), 3.50–3.90 (3H, m), 4.00–4.30 (1H, m), 4.50–4.75 (3H, m), 7.09 (2H, dd, J=8.9, 3.1 Hz), 7.80 (2H, d, J=7.6 Hz);
(+)-APCI/MS (m/z): 588 [M+H]⁺.

(25) N-[3(R)-1-}3-(4-Piperidyl)propionyl}-3-piperidylcarbonyl]-2(R)-[{4-(n-butylacetamidoxy)phenyl}carbonyl]amino-β-alanine
¹H-NMR (D₂O, δ): 0.85 (3H, t, J=7.2 Hz), 1.10–2.10 (15H, m), 2.20–2.60 (3H, m), 2.70–3.50 (8H, m), 3.50–3.90 (3H, m), 4.00–4.35 (1H, m), 4.55–4.75 (3H, m), 7.09 (2H, d, J=8.7 Hz), 7.80 (2H, d, J=8.8 Hz);
(+)-APCI/MS (m/z): 588 [M+H]⁺;

(26) N-[3(R)-1-{3-(4-Piperidyl)propionyl}-3-piperidylcarbonyl]-2(S)-[{4-(N,N-dimethylacetamidoxy)phenyl}carbonyl]amino-β-alanine
¹H-NMR (D₂O, δ): 1.15–2.10 (11H, m), 2.20–2.50 (3H, m), 2.65–3.05 (3H, m), 2.98 (3H, s), 3.10–3.50 (3H, m), 3.50–3.90 (3H, m), 4.05–4.30 (1H, m), 4.50–4.70 (1H, m), 4.98 (2H, s), 7.08 (2H, dd, J=8.8, 3.3 Hz), 7.79 (2H, d, J=7.4 Hz);
(+)-APCI/MS (m/z): 560 [M+H]⁺.

(27) N-[3(R)-1-{3-(4-Piperidyl)propionyl}-3-piperidylcarbonyl]-2(R)-[{4-(N,N-dimethylacetamidoxy)phenyl}carbonyl]amino-β-alanine
¹H-NMR (D₂O, δ): 1.15–2.05 (11H, m), 2.25–2.55 (3H, m), 2.70–3.50 (6H, m), 2.99 (3H, s), 3.10 (3H, s), 3.50–3.95 (3H, m), 4.05–4.35 (1H, m), 4.55–4.75 (1H, m), 4.97 (2H, s), 7.07 (2H, d, J=7.4 Hz), 7.80 (2H, d, J=8.8 Hz);
(+)-APCI/MS (m/z): 560 [M+H]⁺.

(28) N-[3(R)-1-{3-(4-Piperidyl)propionyl}-3-piperidylcarbonyl]-2(S)-[{4-(N-isobutylacetamidoxy)phenyl}carbonyl]amino-β-alanine
¹H-NMR (D₂O, δ): 0.81 (6H, d, J=6.7 Hz), 1.15–2.05 (12H, m), 2.10–2.55 (3H, m), 2.60–3.25 (6H, m), 3.30–3.50 (2H, m), 3.55–3.85 (3H, m), 4.00–4.25 (1H, m), 4.50–4.70 (1H, m), 4.71 (2H, s), 7.10 (2H, dd, J=8.9, 2.9 Hz), 7.81 (2H, d, J=7.3 Hz);
(+)-APCI/MS (m/z): 588 [M+H]⁺.

(29) N-[3(R)1-{3-(4-Piperidyl)propionyl}-3-piperidylcarbonyl]-2(R)-[{4-(N-isobutyiacetamidoxy)phenyl}carbonyl]amino-β-alanine
¹H-NMR (D₂O, δ): 0.83 (6H, d, J=6.7 Hz), 1.20–2.10 (12H, m), 2.25–2.55 (3H, m), 2.65–3.50 (8H, m), 3.50–3.90 (3H, m), 4.05–4.35 (1H, m), 4.55–4.70 (1H, m), 4.71 (2H, s), 7.10 (2H, d, J=8.2 Hz), 7.81 (2H, d, J=8.8 Hz);
(+)-APCI/MS (m/z): 588 [M+H]⁺.

(30) N-[3(R)-1-{3-(4-Piperidyl)propionyl}-3-piperidylcarbonyl]-2(S)-[{4-(N,N-diisopropylacetamnidoxy)phenyl}carbonyl]amino-β-alanine
¹H-NMR (D₂O, δ): 1.10–2.05 (22H, m), 2.15–2.55 (3H, m), 2.55–3.25 (5H, m), 3.25–3.50 (2H, m), 3.50–3.90 (4H, m), 3.90–4.25 (2H, m), 4.50–4.75 (1H, m), 4.90–5.10 (2H, m), 7.05 (2H, dd, J=8.9, 3.1 Hz), 7.79 (2H, d, J=8.8 Hz);
(+)-APCI/MS (m/z): 616 [M+H]⁺.

(31) N-[3(R)-1-{3-(4-Piperidyl)propionyl}-3-piperidylcarbonyl]-2(R)-[{4-(N,N-diisopropylacetarmidoxy)phenyl}carbonyl]amino-β-alanine ¹H-NMR (D₂O, δ): 1.10–2.10 (22H, m), 2.25–2.60 (3H, m), 3.65–3.55 (6H, m), 3.55–4.35 (6H, m), 4.55–4.75 (1H, m), 4.90–5.10 (2H, m), 7.05 (2H, d, J=6.9 Hz), 7.80 (2H, d, J=8.8 Hz);

(+)-APCI/MS (m/z): 616 [M+H]⁺.

(32) N-[3(R)-1-{3-(4-Piperidyl)propionyl}-3-pipenidylcarbonyl]-2(S)-[{3-(N-isobutylacetamidoxy)phenyl}carbonyl]amino-β-alanine ¹H-NMR (D₂O, δ): 0.82 (6H, d, J=6.7 Hz), 1.10–2.10 (12H, m), 2.20–2.60 (3H, m), 2.65–3.30 (7H, m), 3.30–3.50 (2H, m), 3.60–3.95 (3H, m), 4.05–4.30 (1H, m), 4.55–4.75 (3H, m), 7.15–7.60 (4H, m);

(+)-APCI/MS (m/z): 588 [M+H]⁺.

(33) N-[3(R)-1-{3-(4-Piperidyl)propionyl}-3-piperidylcarbonyl]-2(R)-[{4-(N-isobutylacetamidoxy)phenyl}carbonyl]amino-β-alanine ¹H-NMR (D₂O, δ): 0.83 (6H, d, J=6.7 Hz), 1.15–2.05 (12H, m), 2.10–2.60 (3H, m), 2.65–3.90 (12H, m), 4.05–4.35 (1H, m), 4.55–4.80 (3H, m), 7.15–7.65 (4H, m);

(+)-APCI/MS (m/z): 588 [M+H]⁺.

(34) N-[3(R)-1-{3-(4-Piperidyl)propionyl}-3-piperidylcarbonyl]-2(S)-[{4-(isocaprylcarbonylamino)phenyl}carbonyl]amino-β-alanine ¹H-NMR (D₂O, δ): 0.91(6H, d, J=6.0 Hz), 1.08–2.08 (15H, m), 2.08–2.28(1H, m), 2.28–2.55 (4H, m), 2.60–3.05 (3H, m), 3.05–3.30 (1H, m), 3.30–3.50 (2H, m), 3.50–3.88 (3H, m), 4.05–4.25 (1H, m), 4.50–4.75(1H, m), 7.60 (2H, dd, J=8.5, 6.7 Hz), 7.80 (2H, dd, J=8.7, 2.2 Hz);

(+)-APCI/MS (m/z): 572 [M+H]⁺.

(35) N-[3(R)-1-{3-(4-Piperidyl)propionyl}-3-piperidylcarbonyl]-2(R)-[{4-(isocaprylcarbonylamino)phenyl}carbonyl]amino-β-alanine ¹H-NMR (D₂O, δ): 0.92 (6H, d, J=5.9 Hz), 1.10–2.00 (15H, m), 2.15–2.55 (5H, m), 2.65–3.90 (9H, m), 4.05–4.30 (1H, m), 4.55–4.75 (1H, m), 7.60 (2H, dd, J=8.6, 3.8 Hz), 7.81 (2H, d, J=8.6 Hz);

(+)-APCI/MS (m/z): 572 [M+H]⁺.

(36) N-[3(R)-1-{3-(4-Piperidyl)propionyl}-3-piperidylcarbonyl]-2(S)-[{3-(isocaprylcarbonylanmino)phenyl}carbonyl]amino-β-alanine ¹H-NMR (D₂O, δ): 0.92 (6H, d, J=5.1 Hz), 1.10–2.10 (14H, m), 2.10–2.30 (1H, m), 2.30–2.55 (4H, m), 2.55–3.50 (6H, m), 3.50–3.90 (3H, m), 4.05–4.30 (1H, m), 4.50–4.75 (1H, m), 7.45–7.75 (3H, m), 7.79 (1H, d, J=6.8 Hz);

(+)-APCI/MS (m/z): 572 [M+H]⁺.

(37) N-[3(R)-1-{3-(4-Piperidyl)propionyl}-3-piperidylcarbonyl]-2(R)-[{3-(isocaprylcarbonylamino)phenyl}carbonyl]amino-β-alanine ¹H-NMR (D₂O, δ): 0.92 (6H, d, J=5.9 Hz), 1.10–2.05 (14H, m), 2.20–2.55 (5H, m), 2.65–3.90 (8H, m), 4.05–4.35 (1H, m), 4.55–4.75 (1H, m), 7.45–7.90 (4H, m);

(+)-APCI/MS (m/z): 572 [M+H]⁺.

(38) N-[3(R)-1-{3-(4-Piperidyl)propionyl}-3-piperidylcarbonyl]-2(S)-[{4-(isovalerylcarbonylamino)phenyl}carbonyl]amino-β-alanine ¹H-NMR (D₂O, δ): 0.99 (6H, d, J=6.5 Hz), 1.15–2.55 (17H, m), 2.65–3.30 (4H, m), 3.30–3.50 (2H, m), 3.55–3.90 (3H, m), 4.05–4.30 (1H, m), 4.30–4.75 (1H, m), 7.50–7.70 (2H, m), 7.80 (1H, dd, J=8.8, 2.4 Hz);

(+)-APCI/MS (m/z): 558 [M+H]⁺.

(39) N-[3(R)-1-{3-(4-Piperidyl)propionyl}-3-piperidylcarbonyl]-2(R)-[{4-(isovalerylcarbonylarino)phenyl}carbonyl]amino-β-alanine ¹H-NMR (D₂O, δ): 0.99 (6H, d, J=6.5 Hz), 1.15–2.05 (11H, m), 2.05–2.25 (1H, m), 2.25–2.60 (5H, m), 2.70–3.50 (6H, m), 3.50–3.90 (3H, m), 4.05–4.30 (1H, m), 4.50–4.75 (1H, m), 7.60 (2H, dd, J=8.7, 2.7 Hz) 7.81 (2H, d J=8.7 Hz);

(+)-APCI/MS (m/z): 558 [M+H]⁺.

(40) N-[3(R)-1-{3-(4-Piperidyl)propionyl}-3-piperidylcarbonyl]-2(S)-[{3-(isovalerylcarbonylamino)phenyl}carbonyl]amino-β-alanine ¹H-NMR (D₂O, δ): 1.00 (6H, d, J=6.5 Hz), 1.15–2.60 (17H, m), 2.60–3.10 (3H, m), 3.10–3.50 (3H, m), 3.55–3.95 (3H, m), 4.05–4.30 (1H, m), 4.50–4.75 (1H, m), 7.45–7.90 (4H, m);

(+)-APCI/MS (m/z): 558 [M+H]⁺.

(41) N-[3(R)-1-{3-(4-Piperidyl)propionyl}-3-piperidylcarbonyl]-2(R)-[{3-(isovalerylcarbonylamino)phenyl}carbonyl]amino-β-alanine ¹H-NMR (D₂O, δ): 1.00 (6H, d, J=6.5 Hz), 1.15–2.25 (12H, m), 2.25–2.60 (5H, m), 2.70–3.90 (9H, m), 4.10–4.35 (1H, m), 4.55–4.805 (1H, m);

(+)-APCI/MS (m/z): 558 [M+H]⁺.

EXAMPLE 50

A mixture of N-[(R)-1-{3-(4-piperidyl)propionyl}-3-piperidylcarbonyl]-2(S)-(4-benzyloxybenzoyl)amino-β-alanine (190 mg, 0.34 mmol) and 10% Pd—C (50% wet) (60 mg) in methanol (7 mL) was hydrogenated at 1 atm of hydrogen. After 5 hours, the catalyst was removed by filtration, then the filtrate was evaporated in vacuo. The residue was purified by an ODS column chromatography using Daisogel-120SP (10% CH₃CN/water)and freeze-dried to give N-[(R)-1-{3-(4-piperidyl)propionyl}-3-piperidylcarbonyl]-2(S)-(4-hydroxybenzoyl)amino-β-alanine (153 mg, 0.32 mmol, 94.1%) as a white powder IR (KBr) 3400, 1627, 1608, 1550, 1500 cm⁻¹;

¹H-NMR (D₂O, δ): 1.38–1.90 (11H, m), 2.20–2.41 (3H, m), 2.74–3.03 (3H, m), 3.14–3.25 (1H, m), 3.36–3.43 (2H, m), 3.65–3.75 (4H, m), 4.05–4.20 (1H, m), 4.56–4.66 (1H, m), 7.00 (2H, dd, J=1.5, 8.7 Hz), 7.73 (2H, d, J=2.1, 8.7 Hz);

MASS (m/z): 475 [M+1]⁺.

EXAMPLE 51

The following compounds (1) to (3) were obtained in a manner similar to example 50.

(1) N-[(R)-1-{3-(4-Piperidyl)propionyl}-3-piperidylcarbonyl]-2(S)-(3-hydroxybenzoyl)amino-β-alanine ¹H-NMR (D₂O, δ): 1.38–1.91 (11H, m), 2.22–2.46 (3H, m), 2.69–3.36 (6H, m), 3.69–3.83 (3H, m), 4.07–4.21 (1H, m), 4.55–4.67 (1H, m), 7.09–7.65 (4H, m);

MASS (m/z): 475 [M+1]⁺.

(2) N-[(R)-1-{3-(4-Piperidyl)propionyl}-3-piperidylcarbonyl]-2(S)-(hydroxyacetyl)amino-β-alanine IR (KBr) 3409, 1658, 1612, 1550, 1531, 1467, 1444 cm⁻¹;

¹H-NMR (D₂O, δ): 1.36–2.01 (11H, m), 2.46–2.54 (3H, m), 2.84–3.54 (6H, m), 3.69–3.88 (3H, m), 4.09 (3H, s), 4.23–4.29 (1H, m), 4.38–4.44 (1H, m);

MASS (m/z): 413 [M+1]⁺.

(3) N-[(R)-1-{3-(4-Piperidyl)propionyl}-3-piperidylcarbonyl]-2(R)-(hydroxyacetyl)amino-β-alanine IR (KBr) 3411, 1659, 1635, 1625, 1614, 1548, 1531, 1467, 1444 cm⁻¹;

¹H-NMR (D₂O, δ): 1.43–2.01 (11H, m), 2.46–2.54 (3H, m), 2.84–3.46 (6H, m), 3.65–3.91 (3H, m), 4.09 (2H, s), 4.08–4.17 (1H, m), 4.38–4.43 (1H, m);

MASS (m/z): 413 [M+1]⁺.

EXAMPLE 52

To a solution of (3-isobutyloxy) benzoic acid (107 mg, 0.55 mmol) in dichloromethane (2 mL) were added DMF (42 mL, 0.55 mmol) and oxalyl chloride (48 mL, 0.55 mmol) successively at 5° C. After 20 minutes, the mixture was added to a mixture of N-[(R)-1-{3-(1-tert-butoxycarbonyl-4-piperidyl)propionyl}-3-piperidylcarbonyl]-2(S)-amino-β-alanine (208 mg, 0.46 mmol) in $CH_3CN$ (7 mL), monosilylacetamide (1.0 g) and N-methylmorpholine (61 mL, 0.55 mmol) was added via syringe at 5° C. After stirring an hour, the mixture was acidified with 20% aqueous $KHSO_4$ solution, extracted with ethyl acetate and dried over sodium sulfate. After evaporation of the solvent, the residue was treated with 4N hydrochloric acid in ethyl acetate. The insoluble material was collected by filtration, dried and dissolved in water. The solution was neutralized with a saturated aqueous $NaHCO_3$ solution, purified by an ODS column chromatography using Daisogel-120sp (10% $CH_3CN$/water) and freeze-dried to give N-[(R)-1-{3-(4-piperidyl)propionyl}-3-piperidylcarbonyl]-2(S)-(3-isobutyloxybenzoyl)amino-β-alanine (192 mg, 65.8%) as a white powder.

IR (KBr) 3419, 1637, 1633, 1606, 1542, 1473, 1442 $cm^{-1}$;
$^1$H-NMR ($D_2O$, δ): 1.00 (6H, d, J=6.7 Hz), 1.37–2.20 (14H, m), 2.39–2.42 (2H, m), 2.65–3.19 (4H, m), 3.24–3.41 (2H, m), 3.59–3.78 (3H, m), 3.87 (2H, d, J=6.6 Hz), 4.13–4.25 (1H, m), 4.55–4.66 (1H, m), 7.15–7.51 (4H, m);
MASS (m/z): 531 [M+1]$^+$.

EXAMPLE 53

The following compounds (1) and (2) were obtained in a manner similar to example 52.

(1) N-[(R)-1-{3-(4-Piperidyl)propionyl}-3-piperidylcarbonyl]-2(R)-(3-isobutyloxybenzoyl)amino-β-alanine
IR (KBr) 3421, 1639, 1633, 1606, 1542, 1473, 1442 $cm^{-1}$;
$^1$H-NMR ($D_2O$, δ): 1.00 (6H, d, J=6.7 Hz), 1.38–2.13 (14H, m), 2.31–2.43 (2H, m), 2.70–3.84 (9H, m), 3.88 (2H, d, J=6.7 Hz), 4.13–4.26 (1H, m), 4.59–4.68 (1H, m), 7.19–7.51 (4H, m);
MASS (m/z): 531 [M+1]$^+$.

(2) N-[(R)-1-{3-(4-Piperidyl)propionyl}-3-piperidylcarbonyl]-2(S)-(3-benzyloxybenzoyl)amino-β-alanine
$^1$H-NMR ($D_2O$, δ): 1.24–2.65 (16H, m), 2.76–3.03 (3H, m), 3.28–3.49 (2H, m), 3.56–3.75 (3H, m), 4.05–4.15 (1H, m), 4.56–4.63 (1H, m), 4.98–5.08 (2H, m), 7.02–7.45 (9H, m);
MASS (m/z): 565 [M+1]$^+$.

EXAMPLE 54

The mixture of N-[(R)-1-{3-(1-tert-butoxycarbonyl-4-piperidyl)propionyl}-3-piperidylcarbonyl]-2(S)-(4-methoxycarbonylbenzoyl)amino-β-alanine (55 mg, 0.106 mmol) in water (0.5 mL), monosilylacetamide (1.0 g) and N-methylmorpholine (61 mL, 0.55 mmol) was added 1N LiOH solution (0.37 mL) at 5° C. After stirring for 40 minutes, the mixture was neutralized with 20% aqueous $KHSO_4$ solution, then purified by an ODS column chromatography using Daisogel-120sp (10% $CH_3CN$/water) and freeze-dried to give N-[(R)-1-{3-(4-piperidyl)propionyl}-3-piperidylcarbonyl]-2(S)-(4-carboxybenzoyl)amino-β-alanine (40 mg, 75.1%) as a white powder.

IR (KBr) 3419, 1639, 1627, 1596, 1550, 1481, 1444 $cm^{-1}$;
$^1$H-NMR ($D_2O$, δ): 1.23–2.00 (11H, m), 2.11–2.18 (1H, m), 2.38–3.42 (2H, m), 2.68–3.43 (6H, m), 3.58–3.87 (3H, m), 3.99–4.20 (1H, m), 4.55–4.66 (1H, m), 7.80–8.00 (4H, m);
MASS (m/z): 503 [M+1]$^+$.

EXAMPLE 55

The following compounds (1) to (5) were obtained in a manner similar to Example 54.

(1) N-1(R)-1-{3-(4-Piperidyl)propionyl}-3-piperidylcarbonyl]-2(R)-(4-carboxybenzoyl)amino-β-alanine
IR (KBr) 3409, 1640, 1596, 1550, 1477, 1444 $cm^{-1}$;
$^1$H-NMR ($D_2O$, δ): 1.23–1.92 (11H, m), 2.18–2.43 (3H, m), 2.77–2.99 (3H, m), 3.12–4.20 (7H, m), 4.65–4.77 (1H, m), 7.83–8.00 (4H, m);
MASS (m/z): 503 [M+1]$^+$.

(2) N-[(R)-1-{3-(4-Piperidyl)propionyl}-3-piperidylcarbonyl]-2(S)-(4-carboxymethyloxy)amino-β-alanine
IR (KBr) 3421, 1606, 1550, 1500 $cm^{-1}$;
$^1$H-NMR ($D_2O$, δ): 1.38–1.84 (11H, m), 2.30–2.42 (3H, m), 2.74–3.39 (6H, m), 3.64–3.76 (3H, m), 4.02–4.21 (1H, m), 4.56 (2H, s), 4.59–4.64 (1H, m), 7.05 (2H, dd, J=3.7, 8.8 Hz), 7.79 (2H, dd, J=2.3, 8.8 Hz);
MASS (m/z): 533 [M+1]$^+$.

(3) N-[(R)-1-{3-(4-Piperidyl)propionyl}-3-piperidylcarbonyl]-2(R)-(4-carboxymethyloxy)amino-β-alanine
IR (KBr) 3421, 1606, 1550, 1500 $cm^{-1}$;
$^1$H-NMR ($D_2O$, δ): 1.41–1.96 (11H, m), 2.30–2.45 (3H, m), 2.88–3.80 (9H, m), 4.12–4;19 (1H, m), 4.57 (2H, s), 4.62–4.71 (1H, m), 7.05 (2H, dd, J=2.0, 8.8 Hz), 7.79 (2H, d, J=8.8 Hz);
MASS (m/z): 533 [M+1]$^+$.

(4) N-[(R)-1-{3-(4-Piperidyl)propionyl}-3-piperidylcarbonyl]-2(S)-(carboxyacetyl)amino-β-alanine
IR (KBr) 3421, 1606, 1550, 1500 $cm^{-1}$;
$^1$H-NMR ($D_2O$, δ): 1.44–1.95 (11H, m), 2.47–2.55 (3H, m), 2.91–3.52 (9H, m), 3.66–3.88 (2H, m), 4.18–4.24 (1H, m), 4.37–4.43 (1H, m);
MASS (m/z): 441 [M+1]$^+$.

(5) N-[(R)-1-{3-(4-Piperidyl)propionyl}-3-piperidylcarbonyl]-2(R)-(carboxyacetyl)amino-β-alanine
IR (KBr) 3421, 1650, 1602, 1550, 1479 $cm^{-1}$;
$^1$H-NMR ($D_2O$, δ): 1.43–2.01 (11H, m), 2.47–2.55 (3H, m), 2.81–3.53 (9H, m), 3.63–3.98 (2H, m), 4.18–4.26 (1H, m), 4.37–4.46 (1H, m);
MASS (m/z): 441 [M+1]$^+$.

EXAMPLE 56

To a solution of N-[(R)-1-{3-(1-tertbutoxycarbonyl-4-piperidyl)propionyl}-3-piperidylcarbonyl]-2(S)-amino-β-alanine (207 mg, 0.45 mmol) in acetonitrile (7 mL) was added monosilylacetamide (0.8 g), then the mixture was stirred for 30 minutes at 45° C. After the mixture was allowed to cool to room temperature, N-methylmorpholine (50 mL, 0.45 mmol) and a solution of cyclopropylmethyl chloroformate (1 mmol) in dichloromethane (2 mL), which was prepared from cyclopropanemethanol, triphosgene and pyridine, was added successively via syringe. After stirring for 2 hours, the mixture was acidified with 20% aqueous $KHSO_4$ solution, extracted with ethyl acetate and dried over sodium sulfate. After evaporation of the solvent, the residue was treated with 4N hydrochloric acid in ethyl acetate. The insoluble material was collected by filtration, dried and dissolved in water. The solution was neutralized with a saturated aqueous NaHCO₃ solution, purified by an ODS column chromatography using Daisogel-120SP (10% CH₃CN/water) and freeze-dried to give N-[(R)-1-{3-(4-piperidyl)propionyl}-3-piperidylcarbonyl]-2(S)-(cyclopropylmethyloxycarbonyl)amino-β-alanine (120 mg, 47.4%) as a white powder.

¹H-NMR (D₂O, δ): 0.30–0.32 (2H, m), 0.54–0.58 (2H, m), 1.43–2.02 (12H, m), 2.45–2.55 (3H, m), 2.91–3.04 (3H, m), 3.15–3.47 (4H, m), 3.62–3.69 (1H, m), 3.89–3.95 (3H, m), 4.05–4.35 (2H, m);

MASS (m/z): 453 [M+1]⁺.

EXAMPLE 57

The following compounds (1) to (3) were obtained in a manner similar to Example 56.

(1) N-[(R)-1-{3-(4-Piperidyl)propionyl}-3-piperidylcarbonyl]-2(R)-(cyclopropylmethyloxycarbonyl)amino-β-alanine IR (KBr) 1695, 1660, 1617, 1544, 1471 cm⁻¹;

¹H-NMR (D₂O, δ): 0.28–0.31 (2H, m), 0.55–0.59 (2H, m), 1.14–2.02 (12H, m), 2.45–2.55 (3H, m), 2.92–3.04 (3H, m), 3.27–3.47 (4H, m), 3.60–3.72 (1H, m), 3.80–3.95 (3H, m), 4.16–4.35 (2H, m);

MASS (m/z): 453 [M+1]⁺.

(2) N-[(R)-1-{3-(4-Piperidyl)propionyl}-3-piperidylcarbonyl]-2(S)-(isopentyloxycarbonyl)amino-β-alanine ¹H-NMR (D₂O, δ): 0.90 (6H, d, J-6.4 Hz), 1.36–2.02 (14H, m), 2.46–2.54 (3H, m), 2.92–3.04 (3H, m), 3.15–3.46 (4H, m), 3.61–3.70 (1H, m), 3.82–3.89 (1H, m), 4.13–4.31 (4H, m);

MASS (m/z): 469 [M+1]⁺.

(3) N-[(R)-1-{3-(4-Piperidyl)propionyl}-3-piperidylcarbonyl]-2(R)-(isopentyloxycarbonyl)amino-β-alanine ¹H-NMR (D₂O, δ): 0.90 (6H, d, J=6.4 Hz), 1.37–2.02 (14H, m), 2.51–2.54 (3H, m), 2.87–3.04 (3H, m), 3.19–3.70 (5H, m), 3.83–4.34 (5H, m);

MASS (m/z): 469 [M+1]⁺.

EXAMPLE 58

To a solution of N-[3(R)-1-{3-(1-tert-butoxycarbonyl-4-piperidyl)propionyl}-3-piperidylcarbonyl]-2(S)-amino-β-alanine (250 mg, 0.55 mmol) in acetonitrile (8 mL) was added monosilylacetamide (1.0 g), then the mixture was stirred for 20 minutes at 45° C. After the mixture was allowed to cool to 0° C., N-methylmorpholine (73 mL, 0.66 mmol) and a solution of 4-methoxycyclohexanecarbonyl chloride (0.66 mmol) in dichloromethane (2 mL), which was prepared from 4-methoxycyclohexanecarboxylic acid, oxalyl chloride and N,N-dimethylformamide, were added successively via syringe. After stirring at ambient temperature for 4 hours, the mixture was extracted with ethyl acetate and dried over sodium sulfate. After evaporation of the solvent, the residue was treated with 4N hydrochloric acid in ethyl acetate. The insoluble material was collected by filtration, dried and dissolved in water. The solution was neutralized with a saturated aqueous NaHCO₃ solution, purified by an ODS column chromatography using Daisogel-120SP (10% CH₃CN/water) and freeze-dried to give N-[3(R)-1-{3-(4-piperidyl)propionyl}-3-piperidylcarbonyl]-2(S)-(4-methoxycyclohexanecarbonyl)amino-β-alanine (244.4 mg, 89.8%) as a white powder.

¹H-NMR (D₂O, δ): 1.05–2.60 (23H, m), 2.75–3.10 (3H, m), 3.10–3.55 (7H, m), 3.55–3.75 (2H; m), 3.75–4.00 (1H, m), 4.10–4.50 (2H, m);

(+)–APCI/MS (m/z): 495 [M+H]⁺.

EXAMPLE 59

The following compounds (1) to (13) were obtained in a manner similar to Example 58.

(1) N-[3(R)-1-{3-(4-Piperidyl)propionyl}-3-piperidylcarbonyl]-2(R)-(4-methoxycyclohexanecarbonyl)amino-β-alanine ¹H-NMR (D₂O, δ): 1.05–2.60 (23H, m), 2.75–3.75 (12H, m), 3.75–4.55 (3H, m);

(+)–APCI/MS (m/z) 495 [M+H]⁺.

(2) N-[3(R)-1-{3-(4-Piperidyl)propionyl}-3-piperidylcarbonyl]-2(S)-{(4-isoamyloxyphenyl)carbonyl}amino-β-alanine ¹H-NMR (D₂O, δ): 0.90 (6H, d, J=6.3 Hz), 1.10–2.05 (14H, m), 2.05–3.20 (7H, m), 3.20–3.50 (2H, m), 3.50–3.85 (3H, m), 3.85–4.30 (3H, m), 4.45–4.75 (1H, m), 6.85–7.10 (2H, m), 7.79 (2H, d, J=8.6 Hz);

(+)–APCI/MS (m/z): 545 [M+H]⁺.

(3) N-[3(R)-1-{3-(4-Piperidyl)propionyl}-3-piperidylcarbonyl]-2(R)-{(4-isoamyloxyphenyl)carbonyl}amino-β-alanine ¹H-NMR (D₂O, δ): 0.91 (6H, d, J=6.3 Hz), 1.10–2.00 (14H, m), 2.10–2.50 (3H, m), 2.50–3.25 (4H, m), 3.25–3.50 (2H, m), 3.50–3.90 (3H, m), 3.90–4.35 (3H, m), 4.50–4.70 (1H, m), 6.97 (2H, d, J=6.5 Hz), 7.80 (2H, d, J=8.6 Hz);

(+)–APCI/MS (m/z): 545 [M+H]⁺.

(4) N-[3(R)-1-{3-(4-Piperidyl)propionyl}-3-piperidylcarbonyl]-2(S)-{(4-cyclopropylmethoxyphenyl)carbonyl}amino-β-alanine ¹H-NMR (D₂O, δ): 0.36 (2H, q, J=5.7 Hz), 0.65 (2H, q, J=7.2 Hz), 1.10–2.05 (12H, m), 2.10–2.55 (3H, m), 2.60–3.50 (6H, m), 3.55–4.30 (6H, m), 4.50–4.70 (1H, m), 7.07 (2H, dd, J=8.8, 3.6 Hz), 8.78 (2H, d, J=8.8 Hz);

(+)–APCI/MS (m/z): 529 [M+H]⁺.

(5) N-[3(R)-1-{3-(4-Piperidyl)propionyl}-3-piperidylcarbonyl]-2(R)-{(4-cyclopropylmethoxyphenyl)carbonyl}amino-β-alanine ¹H-NMR (D₂O, δ): 0.37 (2H, q, J=6.0 Hz), 0.66 (2H, q, J=7.9 Hz), 1.10–2.05 (12H, m), 2.20–2.55 (3H, m), 2.65–4.30 (12H, m), 4.50–4.75 (1H, m), 7.07 (2H, d, J=8.8 Hz), 7.79 (2H, d, J=8.8 Hz);

(+)–APCI/MS (m/z): 529 [M+H]⁺.

(6) N-[3(R)-1-{3-(4-Piperidyl)propionyl}-3-piperidylcarbonyl]-2(S)-{(4-cyclopentoxyphenyl)carbonyl}amino-β-alanine ¹H-NMR (D₂O, δ): 1.10–2.55 (22H, m), 2.55–3.25 (4H, m), 3.25–3.50 (2H, m), 3.50–3.90 (3H, m), 4.00–4.30 (1H, m), 4.50–4.70 (1H, m), 4.80–5.00 (1H, m), 7.02 (2H, dd, J=8.8, 5.0 Hz), 7.78 (2H, d, J=8.8 Hz);

(+)–APCI/MS (m/z): 543 [M+H]⁺.

(7) N-[3(R)-1-{3-(4-Piperidyl)propionyl}-3-piperidylcarbonyl]-2(R)-{(4-cyclopentoxyphenyl)carbonyl}amino-β-alanine ¹H-NMR (D₂O, δ): 1.10–2.10 (18H, m), 2.20–2.55 (3H, m), 2.60–3.50 (6H, m), 3.50–3.90 (3H, m), 4.00–4.30 (1H, m), 4.50–4.70 (1H, m), 4.85–5.00 (1H, m), 7.03 (2H, d, J=9.1 Hz), 7.79 (2H, d, J=8.8 Hz);

(+)–APCI/MS (m/z): 543 [M+H]⁺.

(8) N-[3(R)-1-{3-(4-Piperidyl)propionyl}-3-piperidylcarbonyl]-2(S)-{(4-isopropoxyphenyl)carbonyl}amino-β-alanine ¹H-NMR (D₂O, δ): 1.15–2.05 (10H, m), 1.35 (6H, d, J=6.1 Hz), 2.10–2.55 (3H, m), 2.65–3.50 (6H, m), 3.50–3.90

(3H, m), 4.00–4.35 (1H, m), 4.50–4.70 (1H, m), 7.08 (2H, dd, J=8.9, 2.9 Hz), 7.78 (2H, d, J=8.8 Hz);

(+)-APCI/MS (m/z): 517 [M+H]$^+$.

(9) N-[3(R)-1-{3-(4-Piperidyl)propionyl}-3-piperidylcarbonyl]-2(R)-{(4-isopropoxyphenyl)carbonyl}amino-β-alanine $^1$H-NMR (D$_2$O, δ): 1.10–2.05 (10H, m), 1.35 (6H, d, J=6.1 Hz), 2.05–2.55 (3H, m), 2.65–3.90 (9H, m), 4.00–4.30 (1H, m), 4.55–4.75 (1H, m), 7.08 (2H, d, J=8.8 Hz), 7.79 (2H, d, J=8.8 Hz);

(+)-APCI/MS (m/z): 517 [M+H]$^+$.

(10) N-[3(R)-1-{3-(4-Piperidyl)propionyl}-3-piperidylcarbonyl]-2(S)-{(4-isohexyloxyphenyl)carbonyl}amino-β-alanine $^1$H-NMR (D$_2$O, δ): 0.87 (6H, d, J=6.3 Hz), 1.05–1.95 (16H, m), 2.05–3.15 (7H, m), 3.15–4.25 (8H, m), 4.40–4.70 (1H, m), 6.84 (2H, d, J=7.4 Hz), 7.81 (2H, d, J=7.4 Hz);

(+)-APCI/MS (m/z): 559 [M+H]$^+$.

(11) N-[3(R)-1-{3-(4-Piperidyl)propionyl}-3-piperidylcarbonyl]-2(R)-{(4-isohexyloxyphenyl)carbonyl}amino-β-alanine $^1$H-NMR (D$_2$O, δ): 0.87 (6H, d, J=6.4 Hz), 1.10–2.00 (16H, m), 2.00–3.15 (7H, m), 3.15–4.30 (7H, m), 4.40–4.70 (1H, m), 6.85 (2H, d, J=7.3 Hz), 7.81 (2H, d, J=7.3 Hz);

(+)-APCI/MS (m/z): 558 [M+H]$^+$.

(12) N-[3(R)-1-{3-(4-Piperidyl)propionyl}-3-piperidylcarbonyl]-2(S)-{(4-neopentyloxyphenyl)carbonyl}amino-β-alanine $^1$H-NMR (D$_2$O, δ): 0.97 (9H, s), 1.15–2.00 (11H, m), 2.00–3.20 (7H, m), 3.20–3.45 (2H, m), 3.45–3.90 (5H, m), 4.05–4.30 (1H, m), 4.50–4.70 (1H, m), 6.97 (2H, d, J=8.4 Hz), 7.80 (2H, d, J=7.8 Hz);

(+)-APCI/MS (m/z): 545 [M+H]$^+$.

(13) N-[3(R)-1-{3-(4-Piperidyl)propionyl}-3-piperidylcarbonyl]-2(R)-{(4-neopentyloxyphenyl)carbonyl}amino-β-alanine $^1$H-NMR (D$_2$O, δ): 0.97 (9H, s), 1.10–2.05 (11H, m), 2.05–2.50 (3H, m), 2.50–3.20 (4H, m), 3.20–3.50 (2H, m), 3.50–3.85 (5H, m), 4.00–4.25 (1H, m), 4.45–4.65 (1H, m), 6.93 (2H, d, J=8.5 Hz), 7.80 (2H, d, J=7.3 Hz);

(+)-APCI/MS (m/z): 545 [M+H]$^+$.

EXAMPLE 60

A mixture of (R)-1-{3-(1-tert-butoxycarbonyl-4-piperidyl)-propionyl}-3-piperidinecarboxylic acid (0.26 g), ethyl-5-(3,4-dimethoxyphenyl)-3-(R)-amino-pentanoate (0.11 g), 1-(3-dimethylaminopropyl)-3-ethylcarbodiimide hydrochloride (0.07 g) and 1-hydroxybenzotriazole (0.05 g) in DMF (5 ml) was stirred at room temperature for 3 hours. The reaction mixture was partitioned between a mixture of ethyl acetate and n-hexane and water. The separated organic layer was washed with water and brine, dried over magnesium sulfate and evaporate. To the solution of the residue in methanol (3 ml) was added 1N aqueous LiOH solution (0.9 ml), and the mixture was stirred for 2 hours at room temperature. The mixture was extracted with diethyl ether. The aqueous layer was acidified with an aqueous KHSO$_4$ solution to pH 2.0 and extracted again with ethyl acetate. The organic layer was dried over sodium sulfate and evaporated to give a residue, which was treated with 4N hydrochloric acid in ethyl acetate. The insoluble material was collected by filtration, dried and dissolved in water. The solution was neutralized with a saturated aqueous NaHCO$_3$ solution, purified by an ODS column chromatography using Daisogel-120SP (10% CH$_3$CN/water) and freeze-dried to give N-[3(R)-1-{3-(4-piperidyl)propionyl}-3-piperidylcarbonyl]-3(R)-(3,4-dimethoxyphenyl)ethyl-β-alanine (125.1 mg, 70.4%).

$^1$H-NMR (D$_2$O, δ): 1.20–2.05 (13H, m), 2.30–2.50 (4H, m), 2.50–2.70 (2H, m), 2.70–3.15 (3H, m), 3.15–3.50 (3H, m), 3.83 (3H, s), 3.85 (3H, s), 4.0–4.25 (2H, m), 6.75–7.05 (3H, m);

(+)-APCI/MS (m/z): 504 [M+H]$^+$.

EXAMPLE 61

The following compounds (1) to (2) were obtained in a manner similar to Example 60.

(1) N-[3(R)-1-{3-(4-Piperidyl)propionyl}-3-piperidylcarbonyl]-3(S)-4-hydroxyphenyl-β-alanine $^1$H-NMR (D$_2$O, δ): 1.20–2.05 (10H, m), 2.30–2.70 (4H, m), 2.80–3.55 (5H, m), 3.65–4.35 (2H, m), 5.10 (1H, t, J=3.6 Hz), 6.87 (2H, d, J=8.6 Hz), 7.24 (2H, dd, J=8.6, 3.2 HZz);

(+)-APCI/MS (m/z): 432 [M+H]$^+$.

(2) N-[3(R)-1-{3-(4-Piperidyl)propionyl}-3-piperidylcarbonyl]-3(S)-4-hydroxyphenyl-β-alanine $^1$H-NMR (D$_2$O, δ): 1.20–2.10 (13H, m), 2.10–2.75 (6H, m), 2.75–3.65 (11H, m), 3.70–4.55 (4H, m), 5.05–5.20 (1H, m), 6.87 (2H, d, J=8.5 Hz), 7.24 (2H, dd, J=8.6, 3.2 Hz);

(+)-APCI/MS (m/z): 488 [M+H]$^+$.

What is claimed is:

1. A β-alanine compound of the formula (I):

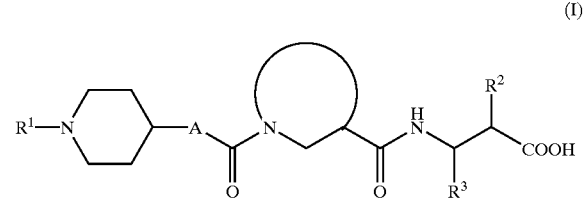

wherein R$^1$ is a hydrogen atom, A is a lower alkylene group, R$^2$ is an amino group which is substituted with an aroyl group substituted with lower alkylcarbamoyl, R$^3$ is hydrogen atom and the moiety represented by the formula:

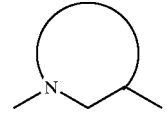

is piperidine-1,3-diyl.

2. The compound of claim 1, wherein A is ethylene group and R$^2$ is an amino group which is substituted with a benzoyl group substituted with lower alkylcarbamoyl.

3. A composition comprising a therapeutically effective amount of a compound of claim 1 and a carrier.

4. A composition comprising a therapeutically effective amount of a compound of claim 2 and a carrier.

5. A method for treating a disease caused by thrombus formation, comprising administering to a patient in need thereof the compound of claim 1 in an amount sufficient to treat the disease.

6. A method for treating a disease caused by thrombus formation, comprising administering to a patient in need thereof the compound of claim 2 in an amount sufficient to treat the disease.

* * * * *

UNITED STATES PATENT AND TRADEMARK OFFICE
CERTIFICATE OF CORRECTION

PATENT NO. : 6,812,235 B2
DATED : November 2, 2004
INVENTOR(S) : Ohkubo et al.

It is certified that error appears in the above-identified patent and that said Letters Patent is hereby corrected as shown below:

<u>Title page, Item [54] and Column 1, line 1,</u>
Title, should read -- BETA-ALANINE DERIVATIVES AND THEIR USE AS RECEPTOR ANTAGONISTS --

Signed and Sealed this

Fifteenth Day of February, 2005

JON W. DUDAS
*Director of the United States Patent and Trademark Office*